(12) United States Patent
Michaeli et al.

(10) Patent No.: US 8,663,102 B2
(45) Date of Patent: Mar. 4, 2014

(54) SURGICAL RETRACTOR

(75) Inventors: David Michaeli, Ashkelon (IL); Michael Michaeli, Rishon Lezion (IL)

(73) Assignee: Meni-Med Ltd., Moshav Mashen (IL)

( * ) Notice: Subject to any disclaimer, the term of this patent is extended or adjusted under 35 U.S.C. 154(b) by 434 days.

(21) Appl. No.: 12/980,395

(22) Filed: Dec. 29, 2010

(65) Prior Publication Data

US 2011/0208008 A1 Aug. 25, 2011

Related U.S. Application Data

(63) Continuation-in-part of application No. 12/880,162, filed on Sep. 13, 2010, now Pat. No. 8,454,504, which is a continuation-in-part of application No. 12/814,492, filed on Jun. 14, 2010, now Pat. No. 8,409,089.

(60) Provisional application No. 61/307,469, filed on Feb. 24, 2010.

(51) Int. Cl.
*A61B 1/32* (2006.01)

(52) U.S. Cl.
USPC .......................... 600/222; 600/225; 600/233

(58) Field of Classification Search
USPC .......... 600/210, 215, 222, 225, 228, 231, 233
See application file for complete search history.

(56) References Cited

U.S. PATENT DOCUMENTS

| 6,210,325 B1 | 4/2001 | Bartie | |
|---|---|---|---|
| 2007/0038216 A1* | 2/2007 | Hamada | 606/53 |
| 2008/0319268 A1 | 12/2008 | Michaeli | |

FOREIGN PATENT DOCUMENTS

WO 0103586 1/2001

* cited by examiner

*Primary Examiner* — Sameh Boles
(74) *Attorney, Agent, or Firm* — Mark M. Friedman

(57) ABSTRACT

A surgical retractor and a method of minimally invasive surgery, wherein the surgical retractor includes ribs and a mechanism for transferring of linear and rotational movements of the ribs and wherein each rib can be easily replaced without use of any additional tools. According to embodiments of the present invention, specific parts composing the surgical retractor are made of materials transparent to Röntgen rays (x-rays).

9 Claims, 41 Drawing Sheets

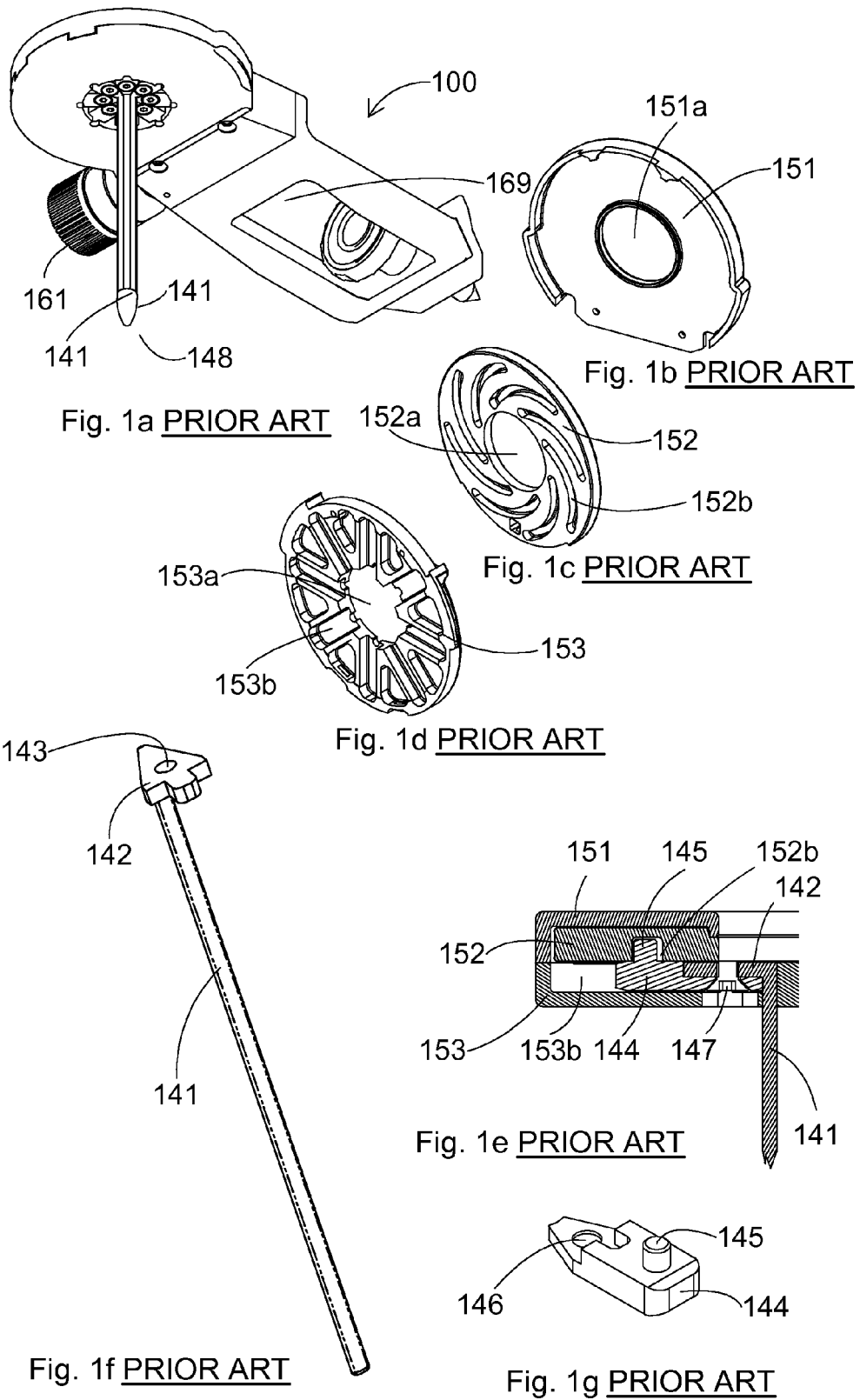

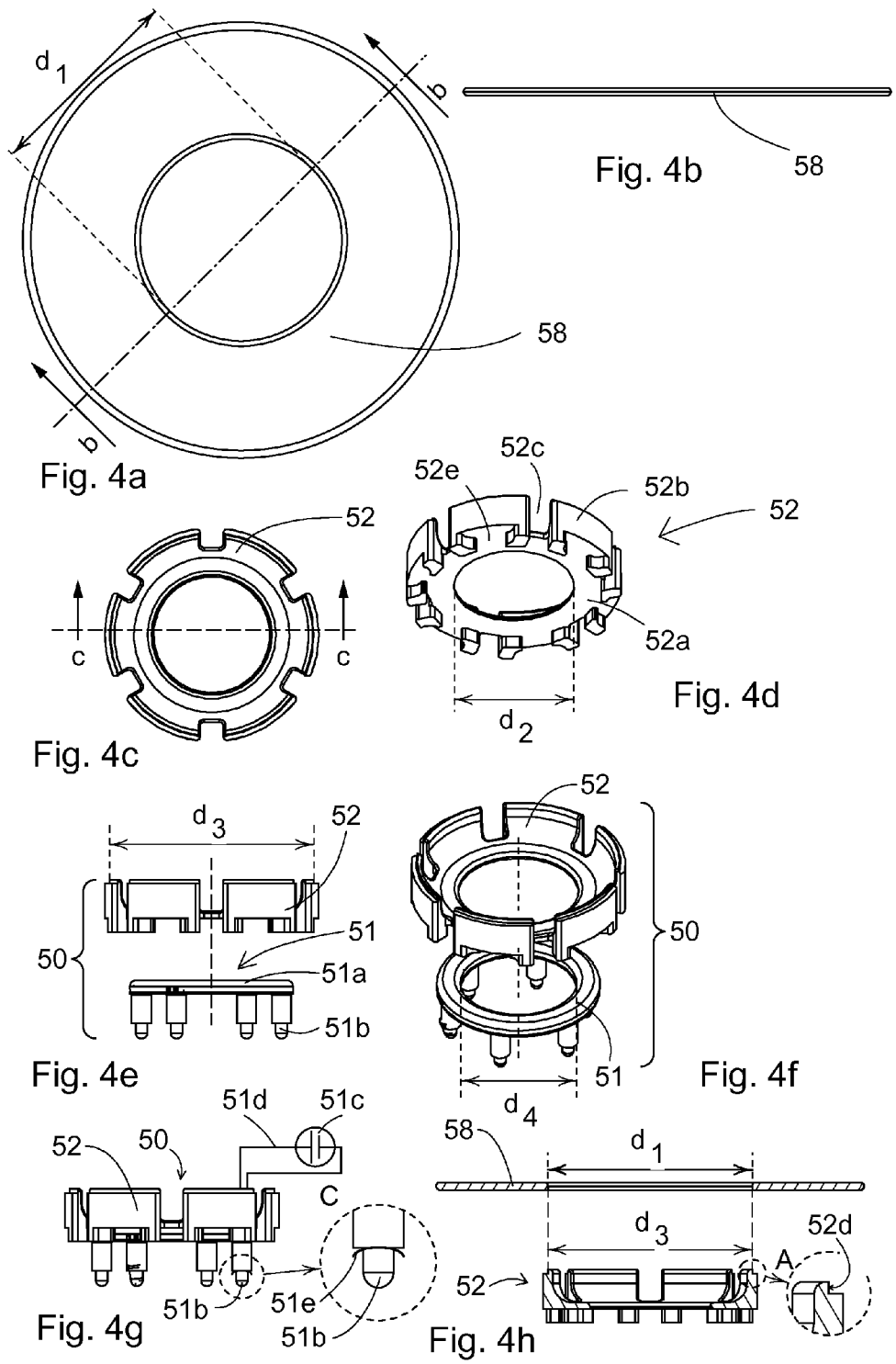

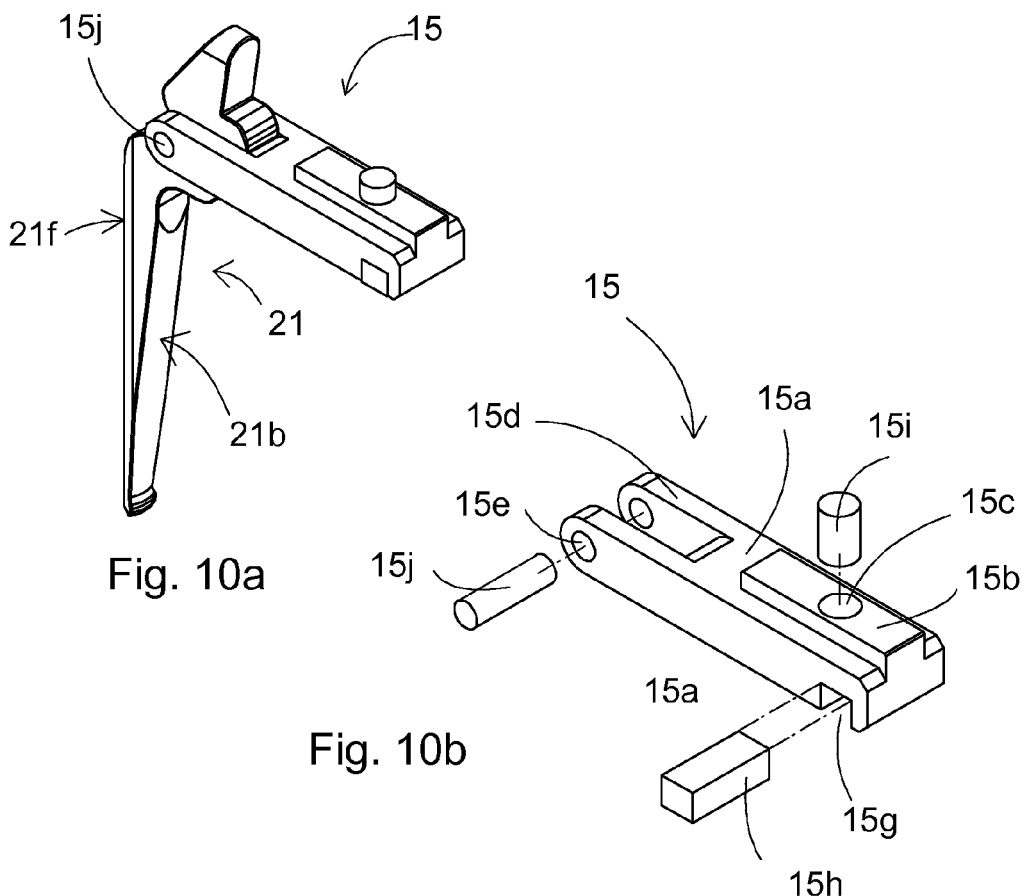

Fig. 10d
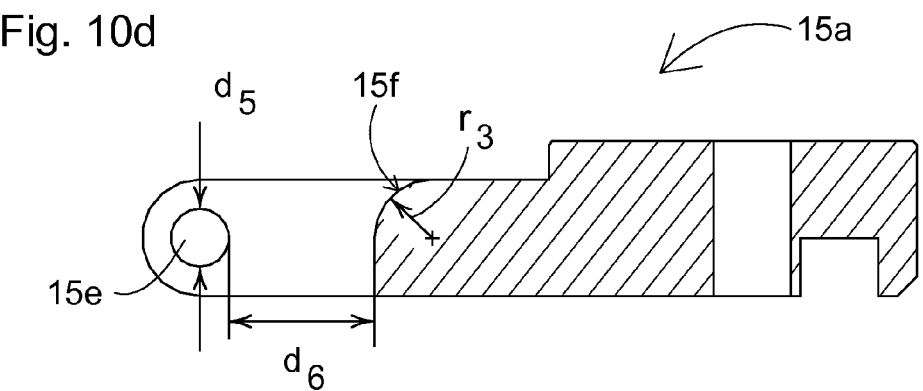
Fig. 10e
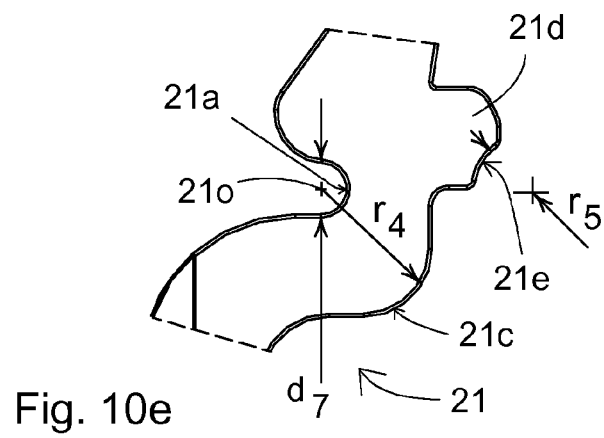
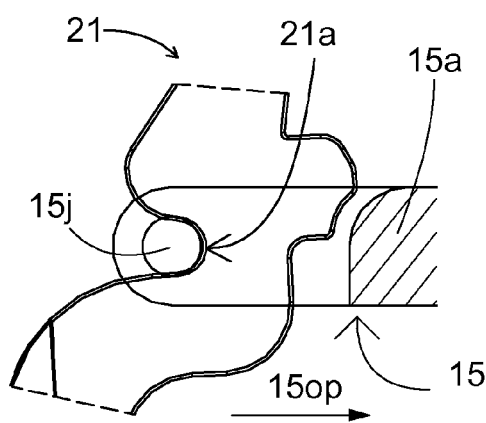
Fig. 10f
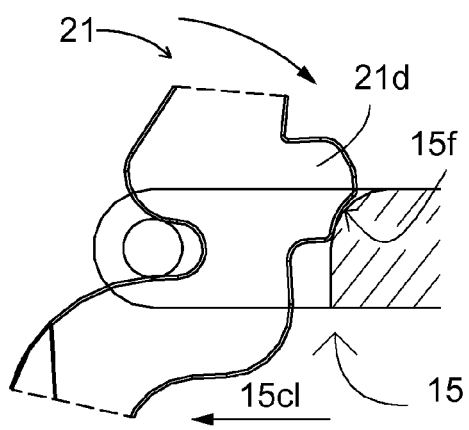
Fig. 10g

SURGICAL RETRACTOR

REFERENCE TO CROSS-RELATED APPLICATION

This application is a Continuation-in-Part of U.S. patent application Ser. No. 12/880,162, filed on Sep. 13, 2010, which is a Continuation-in-Part of U.S. patent application Ser. No. 12/814,492, filed on Jun. 14, 2010, which claims priority from U.S. Provisional Patent Application No. 61/307, 469, filed on Feb. 24, 2010.

This application claims priority benefits from U.S. patent application Ser. No. 12/880,162, filed on Sep. 13, 2010, herein incorporated by reference in its entirety, which claims priority from U.S. patent application Ser. No. 12/814,492, filed on Jun. 14, 2010, herein incorporated by reference in its entirety, which claims priority from U.S. Provisional Application No. 61/307,469, filed on Feb. 24, 2010, herein incorporated by reference in its entirety

FIELD OF THE INVENTION

The present invention relates to apparatus and techniques for performing minimally invasive surgery and, in particular to a retractor device for minimally invasive surgery, more particularly to a new expanding retractor for spinal minimal invasive neurosurgery.

BACKGROUND OF THE INVENTION

A concentrically expansible needle retractor for minimally invasive surgery, of one the present inventors, is described in PCT/IL2000/00387, filed Jul. 4, 2000, the full disclosures of which are incorporated herein by reference.

An improved radial expansible retractor for minimally invasive surgery, of the present inventors, is described in PCT/IL2006/001250, filed Oct. 30, 2006, which has significant improvements which can benefit patients, the full disclosures of which are incorporated herein by reference.

FIG. 1a of the prior art is a perspective view schematic illustration of the improved radial expansible retractor, which will be referred to in the present application as a prior art radial expansible retractor (PARER) 100.

The illustrations show PARER ribs 141 touching each other, forming a hollow cylinder.

The prior art radial expansible retractor 100 is equipped with a PARER adaptor 169 and with a mechanism for transmitting gentle rotational mechanical movement from a PARER rotating wheel 161 to a PARER grooved disc 152, (not shown in the present illustrations).

FIG. 1b of the prior art is a perspective view schematic illustration of a PARER cover 151, of the prior art radial expansible retractor, in whose center is a PARER cover central perforation 151a of a suitable diameter for inserting a tubule and performing the medical procedure.

FIG. 1c of the prior art is a perspective view schematic illustration of a PARER grooved disc 152, of the prior art radial expansible retractor, in whose center is a PARER grooved disc central perforation 152a, of a suitable diameter for inserting the tubule and performing the medical procedure, and PARER grooves 152b, in the present case eight, designated to grant continuous forced movement to rib carrier pins.

In the case of need to open a shape other than a circle, the PARER grooved disc 152 can be used with at least part of the grooves having a different curve, and ends at different distances from the center. This difference necessarily results in different movement of each of the ribs, forming a lateral section, which is not circular.

Namely, the desired opening shape to be achieved by means of prior art radial expansible retractor must be determined prior to commencement of the medical operation.

FIG. 1d of the prior art is a perspective view schematic illustration of a of PARER channeled disc 153, of the prior art radial expansible retractor 100, in whose center is a PARER channeled disc central perforation 153a, of a suitable diameter for inserting the tubule and performing the medical procedure, and PARER channels 153b, in the present case eight, designated to grant continuous forced movement to the rib carrier (not shown in the present figure). The PARER channels 153b are completely straight, and are pointed in the directions of the radiuses from a joint center of the PARER channeled disc 153. Their dimensions conform to those of rib carrier, and they are designated to enable strictly radial movement of PARER rib carrier 144 with regard to the aforementioned center.

Combination of the PARER channeled disc 153 and the PARER cover 151 is done by means of geometrically conforming both to each other, together forming a casing suitable for carrying PARER grooved disc 152 and granting it smooth rotational movement.

FIG. 1e of the prior art is lateral section schematic illustrations of the prior art radial expansible retractor.

The figure clearly showing PARER rib carrier 144 disposed within PARER channel 153b of the PARER channeled disc 153, with a PARER rib carrier pin 145 disposed within PARER groove 152b of the PARER grooved disc 152. The PARER rib carrier 144 connects to PARER rib base 142, which is the integral base of PARER rib 141, by means of PARER rib carrier bolt 147.

FIG. 1f of the prior art is a perspective view schematic illustration of a PARER rib 141 of the prior art radial expansible retractor.

At one end of PARER rib 141, the PARER rib's base 142 is disposed, into which the PARER rib base hole 143 is perforated. PARER rib 141 is formed as an elongated rod whose cross section can have many various geometrical shapes, also including the shape of a section of the wall of a cylinder.

FIG. 1g of the prior art is a perspective view schematic illustration of a PARER rib carrier 144 of the prior art radial expansible retractor. Its shape conforms for connection to the PARER rib's base 142 and it includes PARER rib carrier hole 146, and PARER rib carrier pin 145.

As far as minimal invasive methods of treatment of spinal stenosis are concerned, they are commonly performed with the assistance of tubular retractors.

A tubular retractor for minimally invasive surgery, of Bartie et al., is described in U.S. Pat. No. 6,210,325, granted Apr. 3, 2001, the full disclosures of which are incorporated herein by reference.

Use of tubular retractors for the performance of treatment of spinal stenosis has some very grave drawbacks, also including:

Over traumatization (disruption of muscles and nerves roots) of soft tissues upon insertion of a retractor, in most cases hammering is required to insert the retractor between muscle fibrils, resulting in destruction and disruption of soft tissues. During postoperative recovery, this kind of iatrogenic damage can inflict pain more severe than that caused by the pathology itself.

The tubular retractor frequently causes postoperative hemorrhaging and compression of the spinal cord, with motor function deterioration of the patient's extremities.

Uncontrolled soft tissue retraction (without measurement of retracted tissue pressure (RTP) and retracted tissue oxygen saturation (RTOS)) causes ischemic muscular degeneration-IMD and development of extremely rough postoperative scar tissue, resulting in circular compression of nerve roots and thus severe postoperative pain.

Very fast insertion of such tubular retractors causes splitting of muscles from vertebral bones and hemorrhaging. Surgeons must be aware that even though the surgery is completed effectively in a narrow space, symptoms can occur immediately if even a small hematoma is generated in this space.

Appropriate surgical tools and manual skills are required since surgeons must work in a narrow space. Further, there may be confusion regarding anatomical structures in such a limited space. Another problem is the limitations of effective decompression due to limited and constant (unchangeable, non-adjustable) diameters of tubular retractors.

Due to differing curvatures of vertebral lamina, tubular retractors don't enable the surgeon to approach lateral parts of lamina, including vertebral facets, and vision may be obstructed or disrupted by the use of tools in a narrow space with limited light.

Non-simultaneous unidirectional retraction of muscles causes uneven distribution of pressure to the soft tissues. Uncontrolled soft tissue retraction (without measurement of retracted tissue pressure (RTP) and retracted tissue oxygen saturation (RTOS)) causes ischemic muscular degeneration (IMD), and development of extremely rough postoperative scar tissue, resulting in circular compression of nerve roots and thus severe postoperative pain.

There is thus a widely recognized need for, and it would be highly advantageous to have, a surgical retractor for performing minimally invasive surgery, that will not have the aforementioned drawbacks, that will also enable working with massive tissue pressures to the extent that body tissues can apply, that will enable creating openings of various section shapes which can be changed in the course of operation, and that will be equipped with ribs of various shapes and sizes, that can be easily replaced without use of additional tools.

SUMMARY OF THE INVENTION

The surgical retractor according to the present invention further improves the performance currently available with the prior art. It enables creating openings in the human body in locations in which the tissue pressure on its ribs is significantly more powerful than in brain surgery, such as in operations in close proximity with to the spine, with the ribs of the surgical retractor subject to pressure of the adjacent muscles. An additional improvement is enabling the option of determining the shape of the opening in the operated body created by the surgical retractor when opening, and even changing the shape as necessary throughout the operation. This is achieved by a combination of opening all ribs of the surgical retractor simultaneously as a circle and subsequent individual control of each separate rib's inclination angle. Another major improvement is in enabling the replacement, prior to commencement of use of the surgical retractor, of the ribs of the surgical retractor without any need for any additional tools.

Yet another significant improvement is the addition of a light source to the surgical retractor, which grants the operating surgeon high visibility of the working area.

The surgical retractor can also be added a flexible sleeve, made for example of rubber or silicone, to prevent entry of surrounding tissue into the working channel.

Yet another significant improvement, according to embodiments of the present invention, is that some of the components of the surgical retractor are made of materials transparent to Röntgen rays (x-rays).

According to the teachings of the present invention there is provided a surgical retractor, including: a ribs assembly; a mechanism for transferring of linear and rotational movement adapted to apply mechanical forces and moments to the ribs assembly; and a channeled disc wherein the mechanism for transferring of linear and rotational movement and the ribs assembly are mounted on the channeled disc.

According to another further teaching of the present invention the channeled disc is made of material selected from a group consisting of nylon and polycarbonate.

According to another further teaching of the present invention the ribs assembly includes: at least two ribs, wherein each one of the ribs has a rib force arm and a rib working arm disposed on the rib force arm, wherein the rib has a rib back surface, a rib front surface, a rib top end, a rib bottom end, a rib top end, a rib bottom end and a rib shoulder, wherein the rib shoulder is disposed on the force arm, wherein the rib force arm has a rib force arm length and a rib force arm width, wherein the rib force arm width tapers toward the rib top end, wherein the rib working arm has a rib working arm length and a rib working arm width, wherein the rib working arm width tapers toward the rib bottom end wherein the rib has a concave segment of a rib front surface, the concave segment of a rib front surface having a concave segment of a rib front surface diameter.

According to another further teaching of the present invention the ribs are made of material containing nylon and carbon fibers.

According to another further teaching of the present invention the ribs are made of stainless steel.

According to another further teaching of the present invention at least one of the rib working arms' length is larger than at least another one of the rib working arms' length.

According to another further teaching of the present invention the channeled disc includes: at least two channels.

According to another further teaching of the present invention the mechanism for transferring of linear and rotational movement includes: at least two main sliders, wherein each one of the main sliders has a main slider upper portion having an upper portion length, a main slider mid portion, having a mid portion length wherein the main slider mid portion is disposed on the main slider upper portion, and a main slider lower portion, having a lower portion length, wherein the main slider lower portion is disposed on the main slider mid portion, wherein the upper portion length is larger than the mid portion length, wherein the lower portion length is larger than the upper portion length, and wherein each of the main slider lower portion is partially mounted inside one of the channels.

According to another further teaching of the present invention each of the main sliders includes: a pair of slider arms disposed on the main slider lower portion; and a slider pivot disposed on the pair of slider arms, wherein the main slider lower portion has a slider among arms surface and wherein there is a gap between the slider pivot and the slider among arms surface having a predetermined dimension value, and wherein the slider pivot is adapted for transferring force to the concave segment of a rib front surface.

According to another further teaching of the present invention the main slider has a first interior thread located in the main slider upper portion.

According to another further teaching of the present invention the mechanism for transferring of linear and rotational movement further includes: at least two angular adjustment bolts wherein each of the angular adjustment bolts is mounted inside the one of the first interior thread and is adapted for transferring force to one of the rib force arms.

According to another further teaching of the present invention the main slider has a second interior thread located in the main slider mid portion.

According to another further teaching of the present invention the mechanism for transferring of linear and rotational movement further includes: at least two linear adjustment bolts wherein each of the linear adjustment bolts is mounted inside one of the second interior threads.

According to another further teaching of the present invention the surgical retractor further including: an opening mechanism first type, wherein the opening mechanism first type is adapted for engaging to the main sliders for performing linear opening and wherein the opening mechanism first type is adapted for removing from the main sliders at an operation stage.

According to another further teaching of the present invention the opening mechanism first type includes: an opening mechanism base having at least two opening mechanism base grooves, and at least four opening mechanism base tracks; an opening mechanism pole disposed on the opening mechanism base; opening mechanism arms ring, having at least two pairs of opening mechanism arms ring arms, wherein the opening mechanism arms ring has opening mechanism arms ring central hole, and wherein the opening mechanism arms ring is mounted on the opening mechanism pole; at least two opening mechanism arms; at least two opening mechanism sliders; at least four opening mechanism arm upper pivots; and at least four opening mechanism arm lower pivots, wherein each one of the opening mechanism arm upper pivot is disposed on one of the pairs of opening mechanism arms ring arms, wherein each one of the opening mechanism arm lower pivots is disposed on one of the opening mechanism sliders, wherein the each one of the opening mechanism arms is mounted on the opening mechanism arm upper pivot and on one of the opening mechanism arm lower pivots.

According to another further teaching of the present invention the surgical retractor further includes: an opening mechanism second type, wherein the opening mechanism second type is adapted for engaging to the main sliders for performing linear opening and wherein the opening mechanism first type is adapted for removing from the main sliders at an operation stage.

According to still another further teaching of the present invention the opening mechanism second type includes: an opening mechanism base having at least two opening mechanism base grooves, and at least four opening mechanism base tracks; an opening mechanism cylinder disposed on the opening mechanism base, wherein the opening mechanism cylinder has an opening mechanism cylinder external thread and an opening mechanism cylinder internal diameter; an opening mechanism nut mounted on the opening mechanism cylinder, wherein the opening mechanism cylinder has an opening mechanism nut internal thread; an opening mechanism arms ring, having at least two pairs of opening mechanism arms ring arms, wherein the opening mechanism arms ring has an opening mechanism arms ring central hole, and wherein the opening mechanism arms ring is mounted on the opening mechanism cylinder; at least two opening mechanism arms; at least two opening mechanism sliders; at least four opening mechanism arm upper pivots; and at least four opening mechanism arm lower pivots, wherein each one of the opening mechanism arm upper pivots is disposed on one of the pairs of opening mechanism arms ring arms, wherein each one of the opening mechanism arm lower pivots is disposed on one of the opening mechanism sliders, and wherein the each one of the opening mechanism arms is mounted on the opening mechanism arm upper pivot and on one of the opening mechanism arm lower pivots.

According to another further teaching of the present invention each one of the opening mechanism sliders includes: an opening mechanism slider upper channel, adapted for enabling a rotational movement of one of the opening mechanism arm; an opening mechanism slider bottom channel adapted for engaging to one of the main sliders; two opening mechanism slider side channels, wherein each one of the opening mechanism slider side channels is adapted for enabling a linear movement of one of the main sliders on one of the opening mechanism base tracks; and an opening mechanism slider pushing portion adapted for transferring force to one of the main sliders.

According to another further teaching of the present invention the surgical retractor further includes: an external disc having at least two external disc stairs, wherein the external disc is mounted on the channeled disc and partially between each of the main sliders, the main slider upper portion and the main slider lower portion, wherein the external disc is adapted for rotational movement around the channeled disc, and wherein the external disc stairs are adapted for prevention the main sliders from movement.

According to another further teaching of the present invention the surgical retractor further includes: a lighting assembly disposed on the channeled disc.

According to the teaching of the present invention there is provided a method of minimally invasive operation for decompression of spinal stenosis, the method including the stages of: inserting a surgical retractor through a bilateral projection of first bilateral vertebral lamina, wherein the surgical retractor has ribs, a mechanism for transferring of linear and rotational movements to the ribs, and a channeled disc, wherein the channeled disc is made of material selected from a group consisting of nylon and polycarbonate; moving the ribs in linear movements; moving at least one of the ribs in a rotational movement; incising a first lamina; inserting a wedge for a distraction of the first bilateral vertebral lamina; and replacing at least one of the ribs.

BRIEF DESCRIPTION OF THE DRAWINGS

The invention is herein described, by way of example only, with reference to the accompanying drawings, wherein:

FIG. 1a of the prior art is a perspective view schematic illustration of a prior art radial expansible retractor.

FIG. 1b of the prior art is a perspective view schematic illustration of a cover of the prior art radial expansible retractor.

FIG. 1c of the prior art is a perspective view schematic illustration of a grooved disc of the prior art radial expansible retractor.

FIG. 1d of the prior art is a perspective view schematic illustration of a channeled disc of the prior art radial expansible retractor.

FIG. 1e of the prior art is lateral section schematic illustrations of part of the prior art radial expansible retractor.

FIG. 1f of the prior art is a perspective view schematic illustration of a rib of the prior art radial expansible retractor.

FIG. 1g of the prior art is a perspective view schematic illustration of a rib carrier of the prior art radial expansible.

FIG. 4a is a top view schematic illustration of a guarding ring, according to an embodiment of the present invention, upon which a section plane b-b is marked.

FIG. 4b is a side view schematic illustration of the guarding ring, according to an embodiment of the present invention.

FIG. 4c is a top view schematic illustration of a lighting source supporter, according to an embodiment of the present invention, upon which a section plane c-c is marked.

FIG. 4d is an isometric bottom view schematic illustration of a lighting source supporter, according to an embodiment of the present invention.

FIG. 4e is an exploded side view schematic illustration of a lighting assembly, according to an embodiment of the present invention.

FIG. 4f is an exploded isometric top view schematic illustration of a lighting assembly, according to an embodiment of the present invention.

FIG. 4g is a side view schematic illustration of a lighting assembly, according to an embodiment of the present invention.

FIG. 4h is a cross sectional view b-b illustration of a guarding ring and a cross sectional view c-c illustration of a lighting source supporter according to an embodiment of the present invention.

FIG. 10a is an isometric top view schematic illustration of a rib and a main slider combined together, according to an embodiment of the present invention.

FIG. 10b is an exploded isometric top view schematic illustration of a main slider, according to an embodiment of the present invention.

FIG. 10c is a top view schematic illustration of a slider main body, according to an embodiment of the present invention, upon which a section plane e-e is marked.

FIG. 10d is a cross sectional view e-e illustration of a slider main body, according to an embodiment of the present invention.

FIG. 10e is a partial side view illustration of a rib, according to an embodiment of the present invention.

FIG. 10f is a partial side view illustration of a rib and a main slider, according to an embodiment of the present invention.

FIG. 10g is a partial side view illustration of a rib and a main slider, according to an embodiment of the present invention.

DETAILED DESCRIPTION OF EMBODIMENTS

Figure 2A:
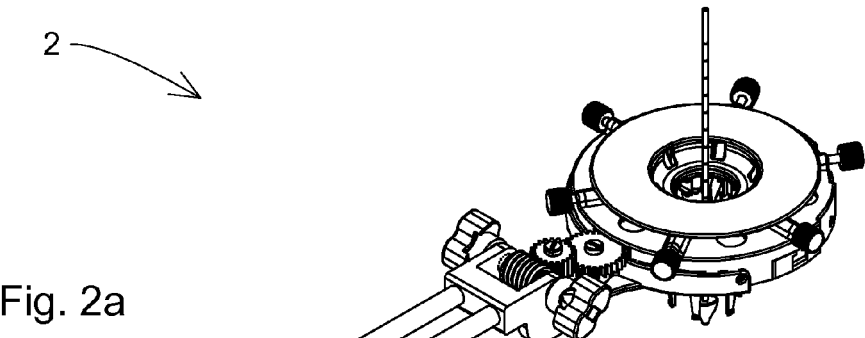
FIG. 2a, is an isometric view schematic illustrations of a surgical retractor according to an embodiment of the present invention.

The present invention is a surgical retractor. The principles and operation of a surgical retractor according to the present invention may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawings.

Unless otherwise defined, all technical and scientific terms used herein have the same meaning as commonly understood by one of ordinary skill in the art to which this invention belongs. The materials, dimensions, methods, and examples provided herein are illustrative only and are not intended to be limiting.

The following list is a legend of the numbering of the application illustrations:

2 surgical retractor
10 mechanism for transferring of linear and rotational movements
11 cover disc
11a cover disc base
11b cover disc base
11c cover disc wall
11d cover disc wall hole
11e cover disc wall openings
11f cover disc supports
11g cover disc base hole
11i cover disc perforation
11j cover disc holding pin
12 grooved disc
12a grooved disc central perforation
12b curved groove
12c grooved disc outer surface
12d grooved disc hole
12e grooved disc teeth
12ao grooved disc central perforation center
12bo groove radius origin
12f grooved disc body
13 channeled disc
13a channeled disc base
13b channeled disc wall
13c channeled disc wall niche
13d channeled disc wall hole
13e channeled disc perforation
13f channeled disc long slot
13g channeled disc short slot
13h track
13i track side wall
13j track upper wall
13k channel
13l channel upper opening
13m channeled disc wall tenon
13n lamp housing
13p channeled disc wire hole
14a angular adjustment bolt
14b linear adjustment bolt
14c linear adjustment bolt head
15 main slider
15a slider main body
15b slider upper body
15c slider pin hole
15d slider arm
15e slider pivot hole
15f slider among arms surface
15g slider niche
15h slider friction reducer
15i slider pin
15j slider pivot
15op movement toward opening
15cl movement toward closing
15m first interior thread
15n second interior thread
15p main slider upper portion
15q main slider mid portion
15r main slider lower portion
15s main slider back edge
16 carrier
16a carrier bow
16b carrier bow bottom hole
16c carrier bridge
16d carrier bridge first hole
16e carrier bridge second hole
16f carrier arm
16g carrier back wall
16h carrier back wall hole
16i carrier bow side hole
16j carrier arm hole
17 transmission
17a transmission knob
17b transmission shaft
17c transmission worm
17e transmission tubular
17f transmission first cog wheel
17g transmission second cog wheel
17h transmission third cog wheel
18 base disc
19 external disc 19h external disc stair
20 ribs assembly
21 rib
21a concave segment of a rib front surface
21b rib back surface
21c convex segment of a rib back surface
21d rib shoulder
21e rib shoulder concave segment
21f rib front surface
21fa rib force arm
21g rib top end
21h rib bottom end
21i rib bottom end projection
21j rib force arm front surface
21k rib working arm front surface
21m rib hole
21n rib hook
21p rib hook pin
21q rib segment
21r cable tensioner
21s cable
21t anchoring point
21md movement direction (of a rib)
21rm rotational movement (of a rib)
21wa rib working arm
21o concave segment of a rib front surface origin
23 flexible sleeve
30 central rod
30a central rod tail
30b central rod tail slot
30c central rod head dome
30s central rod tail symmetrical line
40 adaptor
40a adaptor rod
40b lock first part
40c lock second part
40d lock connector
40e lock fastener screw
40f clip
44 connector
47 clamp
48 holding arm
50 lighting assembly
51 lighting source
51a lighting source supporter base
51b lamp
51c power source
51d electricity conductors
51e light reflector
52 lighting source supporter
52a lighting source supporter base
52b lighting source supporter wall
52c lighting source supporter wall slots
52d lighting source supporter wall shoulder
52e lighting source supporter wall groove
58 guarding ring
60a opening mechanism first type
60a opening mechanism second type
61a opening mechanism pole
61b opening mechanism cylinder
61ba opening mechanism cylinder external thread
61D opening mechanism cylinder internal diameter
62 opening mechanism arms ring
62a opening mechanism arms ring central hole
62b opening mechanism arms ring arm
63 opening mechanism arm
63a opening mechanism arm upper pivot
63b opening mechanism arm lower pivot
64 opening mechanism slider
64a opening mechanism slider upper channel
64b opening mechanism slider bottom channel
64c opening mechanism slider side channel
64d opening mechanism slider pushing portion
65 opening mechanism base
65a opening mechanism base hole
65b opening mechanism base groove
65c opening mechanism base track
70 opening mechanism nut
66a opening mechanism nut body
66b opening mechanism nut internal thread
66c opening mechanism nut handle
70 casing
70a casing bolt
80a pressure sensor
80b tissue oxygen saturation sensor
80c transparent window
80d electrical conductor
80e pressure transducer
80f oxygen saturation sensor
90 body tissue
90a muscle
90b spinal canal
90c vertebra
90d incision line of lamina
90e bone
90f skin
90g discus hernia
90h spinosus
90i spinal cord
90j lamina
91 wedge
92 fascia
F force (general)
$F_1$ adjustment bolt force
$F_2$ body tissue force
$F_3$ slider pivot force
$F_4$ test force
$F_5$ axial force
$F_6$ radial force
$d_1$ guarding ring interior diameter
$d_2$ lighting source supporter base ring interior diameter
$d_3$ lighting source supporter wall shoulder outer diameter
$d_4$ lighting source base interior diameter
$d_5$ slider pivot hole diameter
$d_6$ gap between the slider pivot and the slider among arms surface
$d_7$ concave segment of a rib front surface diameter
$d_8$ rib force arm length
$d_9$ rib working arm length
$d_{10}$ rib working arm projection to the center
$d_{11}$ rib force arm width
$d_{12}$ rib working arm width
$d_{13}$ rib bottom end deflection
$d_{14}$ slider arms gap
$d_{15}$ rib cross section head cut off length
$d_{16}$ rib thickness
$d_{17}$ central rod tail diameter
$d_{18}$ ribs interior diameter
$d_{19}(\mu)$ slider pin distance from the grooved disc central perforation center
$d_{20}$ slider pivot distance from the grooved disc central perforation center
$d_{21}$ upper portion length
$d_{22}$ mid portion length $d_{23}$ lower portion length
$r_1$ groove radius
$r_2$ channeled disc perforation radius
$r_3$ slider among arms surface radius
$r_4$ convex segment of a rib back surface radius
$r_5$ rib shoulder concave segment radius
$\alpha$ angle between the slider and the channeled disc
$\beta$ angle between the rib force arm front surface to the rib working arm front surface
$\gamma$ rib cross section head angle
$\mu$ grooved disc rotational angle
$\delta$ rib opening angle
100 prior art radial expansible retractor (PARER)
141 PARER rib
142 PARER rib base
143 PARER rib base hole
144 PARER rib carrier
145 PARER rib carrier pin
146 PARER rib carrier hole
147 PARER rib carrier bolt
148 PARER central rod
151 PARER cover disc
151a PARER cover central perforation
152 PARER grooved disc
152a PARER grooved disc central perforation
152b PARER groove
153 PARER channeled disc
153a PARER channeled disc central perforation
153b PARER channel
161 PARER rotating wheel
169 PARER adaptor Referring now to the drawings, FIG. 2a, is an isometric top view schematic illustration of a surgical retractor 2 according to an embodiment of the present invention.

The surgical retractor 2 is shown in an assembled state.

Figure 2B:
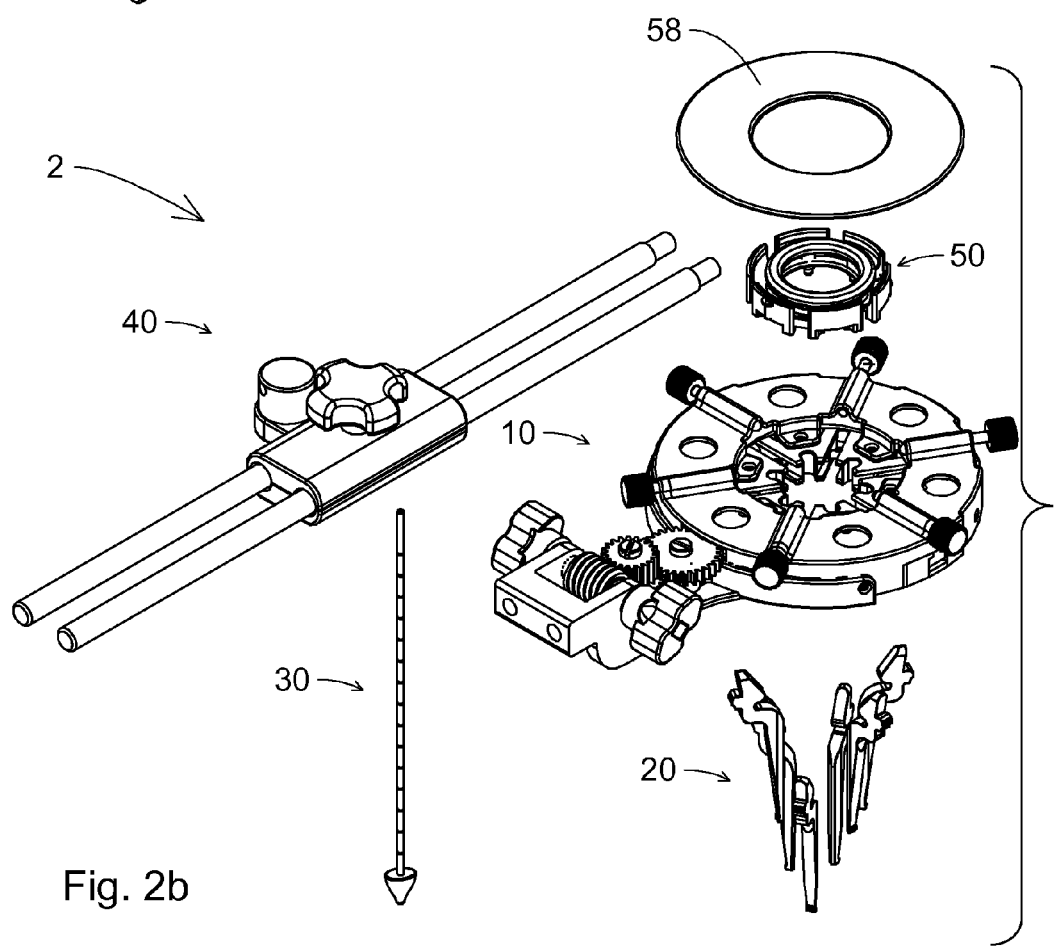
FIG. 2b, is an exploded, isometric top view schematic illustrations of a surgical retractor, up to main assemblies, according to an embodiment of the present invention.

FIG. 2b, is exploded, isometric top view schematic illustrations of a surgical retractor 2, up to main assemblies, according to an embodiment of the present invention.

The active assembly, which practically creates the opening in the operated patient's body for the purpose of performing the operation, is a ribs assembly 20, which can have an integrated central rod 30, which leads the penetration into the body. The ribs assembly 20 has a wide range of opening states, which will be described in further detail in the following. These opening states are commanded and controlled by a mechanism for transferring of linear and rotational movements 10. In addition, the surgical retractor 2, according to the present invention, can include a lighting assembly 50 for the purpose of illuminating the operation area, a guarding ring 58 to prevent entry of foreign objects, dust, dirt, etc., into the surgical retractor 2, and adaptor 40 for the purpose of connection to a holder device.

Figure 2C:
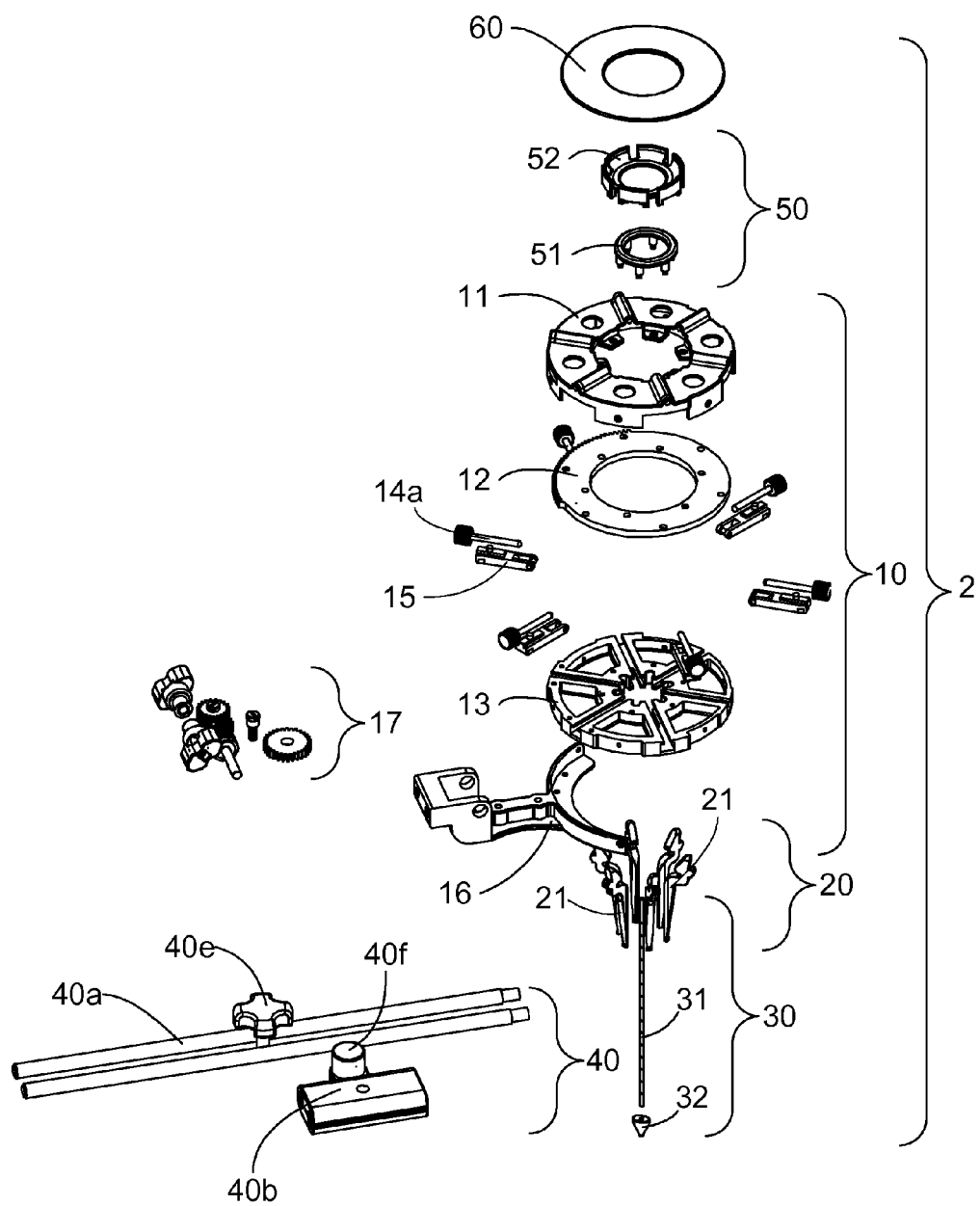
FIG. 2c, is an exploded, isometric top view schematic illustrations of a surgical retractor, up to elements, according to an embodiment of the present invention.

FIG. 2c, is exploded, isometric top view schematic illustrations of a surgical retractor 2, up to elements, according to an embodiment of the present invention.

The lighting assembly 50, according to an embodiment of the present invention, includes lighting source 51 and lighting source supporter 52. The mechanism for transferring of linear and rotational movement 10, according to an embodiment of the present invention, includes cover disc 11, grooved disc 12, channeled disc 13, six angular adjustment bolts 14a, six main sliders 15, a carrier 16, and a transmission 17. The ribs assembly 20, according to an embodiment of the present invention, includes six ribs 21.

According to another embodiment of the present invention the quantity of ribs 21 is other than six, and therefore the quantities of the other elements, quantified as six in the present illustration, are correspondingly quantified.

The central rod 30, according to an embodiment of the present invention, includes central rod tail 31, and central rod head dome 32. The adaptor 40, according to an embodiment of the present invention, includes one or more adaptor rods 40a, lock first part 40b, and lock fastener screw 40e.

As noted, the quantities of elements noted above are in no way limiting the present invention, and there may be other combinations of quantities, such as eight ribs 21. The positions and connections of these assemblies, also with regard to each other, their functions, and methods of operation, will be specified in the following.

While the general preference is for a surgical retractor 2 suitable for repeated use, made such that it can be sterilized, sterilization of the components can be avoided by integration of certain single-use components. Examples of possible single-use components are ribs 21 and lighting source 51.

Figure 3A:
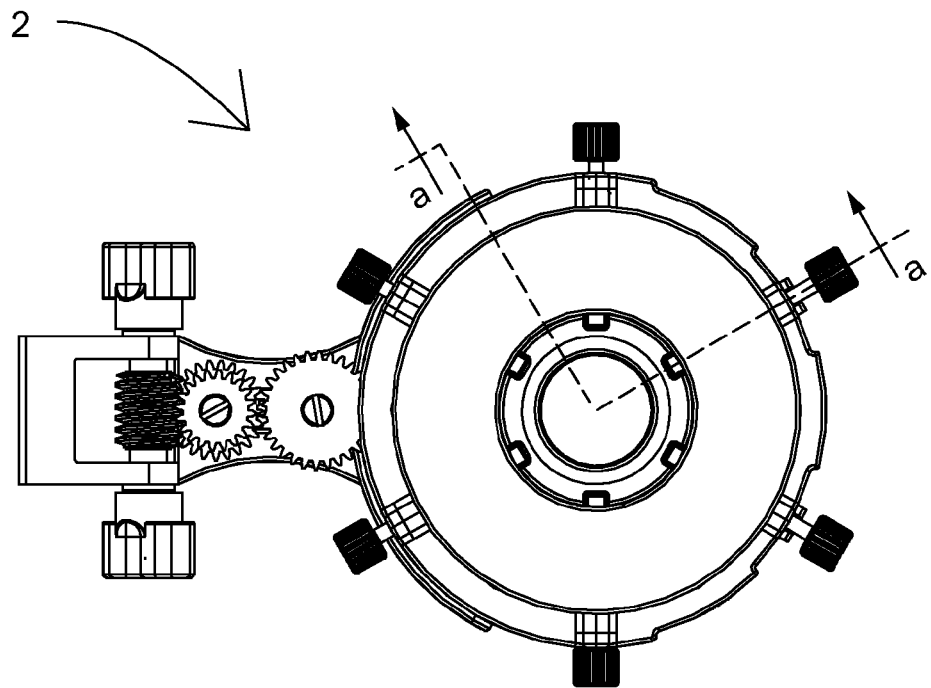
FIG. 3a is a top view schematic illustration of a surgical retractor, without adaptor, according to an embodiment of the present invention, upon which a section plane a-a is marked.

FIG. 3a is a top view schematic illustration of a surgical retractor 2, without an adaptor, according to an embodiment of the present invention, upon which a section plane a-a is marked.

Figure 3B:
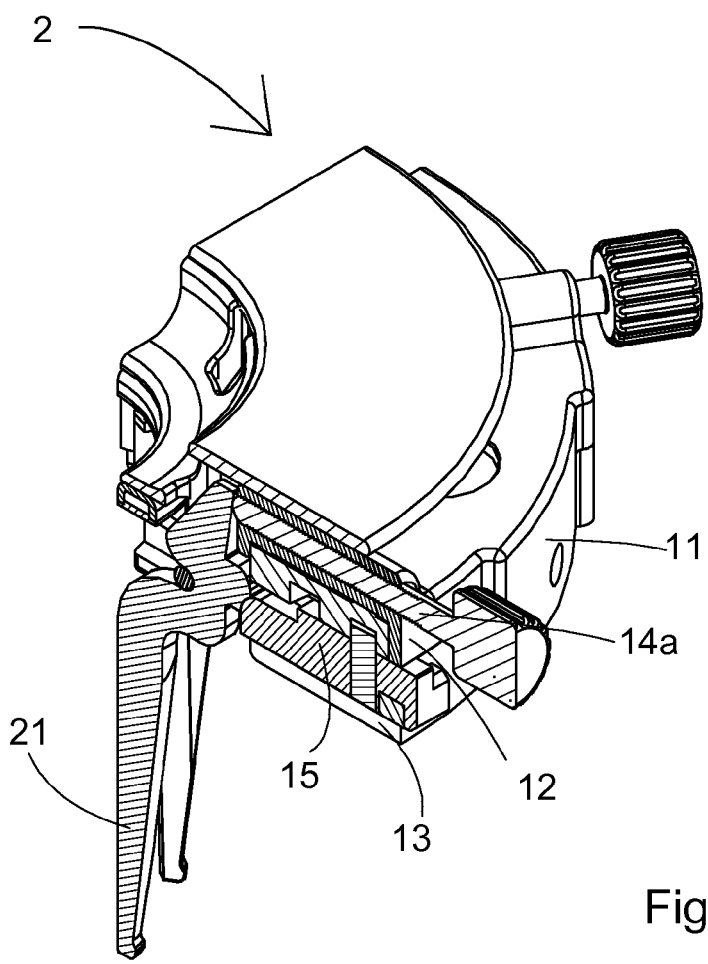
FIG. 3b is a cross sectional view a-a illustration of a surgical retractor, according to an embodiment of the present invention.

FIG. 3b is a cross sectional view a-a, isometric top illustration of a surgical retractor 2, according to an embodiment of the present invention.

The section shows the positions of elements relative to each other. Rib 21 is engaged within a main slider 15. The cover disc 11 encases the main slider 15 and the grooved disc 12 from the outside, and is connected to the channeled disc 13. An angular adjustment bolts 14a is engaged with the cover disc 11 and can be in contact with rib 21.

FIG. 4a is a top view schematic illustration of a guarding ring 58, according to an embodiment of the present invention, upon which a section plane b-b is marked.

As noted, the guarding ring 60 is meant to prevent the entry of foreign objects, dust, dirt, etc., into the surgical retractor.

The guarding ring 58 is shaped as a flat ring, having a guarding ring interior diameter $d_1$. This inner diameter must be of a sufficient size to enable passage of the operating tools, as well as to provide the surgeon with a wide enough visual field. The value of this diameter should preferably be no smaller than 50 millimeters.

FIG. 4b is a side view schematic illustration of the guarding ring 58, according to an embodiment of the present invention.

FIG. 4c is a top view schematic illustration of a lighting source supporter 52, according to an embodiment of the present invention, upon which a section plane c-c is marked.

FIG. 4d is an isometric bottom view schematic illustration of a lighting source supporter 52, according to an embodiment of the present invention.

The lighting source supporter 52 includes a lighting source supporter base 52a, which can be shaped as a ring, having a lighting source supporter base ring interior diameter $d_2$.

This diameter must also be of a sufficient size, similarly to the diameters of other elements to be described in the following, for the same reasons given with regard to the size of guarding ring interior diameter $d_1$ (not shown in the present drawings).

Surrounding the lighting source supporter base 52a is a lighting source supporter wall 52b with a walled cylinder shape, on which are lighting source supporter wall slots 52c, which are meant to prevent disruption of the movement of other elements.

The lighting source supporter wall 52b in the configuration shown in the present illustrations protrudes slightly above and beneath the lighting source supporter base 52a, and the part that protrudes beneath has lighting source supporter wall grooves 52e.

FIG. 4e is an exploded side view schematic illustration of a lighting assembly 50, according to an embodiment of the present invention.

The lighting assembly 50 shown in the present illustration is composed of the lighting source supporter 52 and lighting source 51; however other configurations can also be used, with the lighting assembly 50 being composed of a single unit.

The lighting source 51 includes a lighting source base 51a and one or more lamps 51b, which can also be light emitting diode (LED) lights.

According to one embodiment of the present invention, at least one lamp 51b is an ultra violet (UV) LED, which provides disinfection during the surgical procedure.

The lighting source 51, if not suitable for repeated sterilization, is a disposable component, meant for single-time use. All other elements must be composed of materials suitable for medical standard repeated sterilization.

FIG. 4f is an exploded isometric top view schematic illustration of a lighting assembly 50, according to an embodiment of the present invention.

The lighting source 51 has a lighting source base interior diameter $d_4$. The external shape of the lighting source 51 at least partially conforms to the internal shape of the lighting source supporter 52, so that they are fastened to each other by force of friction, which is no smaller than the weight of each of these elements.

FIG. 4g is a side view schematic illustration of a lighting assembly 50, according to an embodiment of the present invention.

The present illustration shows the lighting source supporter wall 52b and the lighting source supporter base 51a, engaged with each other. In another possible configuration, the lighting assembly 50 is composed of one unit whose shape is practically identical to that of the engaged units, other than lamps 51b. The lamps 51b are electrically fed from power source 51c by means of electricity conductors 51d.

Attached to each lamp 51b, according to an embodiment of the present invention, is a light reflector 51e, shown magnified in circle C, which reflects the light so as to facilitate the surgeon's good view of the working area, without glaring directly into the surgeon's eyes.

FIG. 4h is a cross sectional view b-b illustration of a guarding ring 58 and a cross sectional view c-c illustration of a lighting source supporter 52 according to an embodiment of the present invention.

The top part of the lighting source supporter 52 has a lighting source supporter wall shoulder 52d, shown magnified in circle A, which has a lighting source supporter wall shoulder outer diameter $d_3$.

The lighting source supporter wall shoulder outer diameter $d_3$ and the guarding ring interior diameter $d_1$ are practically of the same value, so that when the guarding ring 58 is engaged with lighting source supporter 52, a friction force occurs between them, preventing the guarding ring 58 from separating as a result of gravity or of movement. There are other possible methods of connecting the guarding ring 58 with the lighting source supporter 52, such as by means of screwing, riveting, etc., and even by means of a fixed connection, when they are composed as a single unit.

Figure 5A:
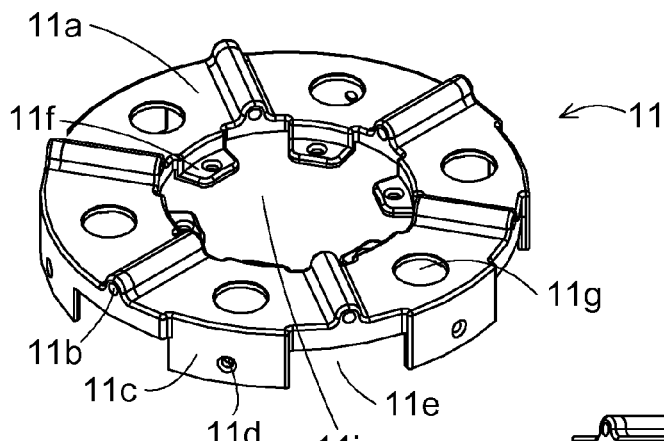
FIG. 5a is an isometric top view schematic illustration of a cover disc, according to an embodiment of the present invention.

FIG. 5a is an isometric top view schematic illustration of a cover disc 11, according to an embodiment of the present invention.

The cover disc 11 includes a cover disc base 11a having several cover disc base interior threads 11b and cover disc base holes 11g.

The presence of the cover disc base holes 11g serves the purpose of reducing weight and enables effective penetration of materials such as detergents during rinsing and disinfection.

The cover disc base 11a is shaped as a flat ring, the internal part of the ring being disposed with cover disc supports 11f, and its external circumference is mounted within a cover disc wall 11c.

The cover disc wall 11c is shaped as a walled cylinder, having cover disc wall holes 11d, and cover disc wall openings 11e.

The cover disc supports 11f protrude into a cover disc perforation 11i.

Figure 5B:
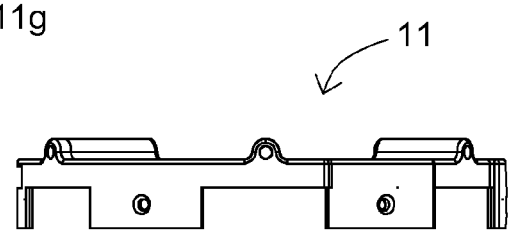
FIG. 5b is a side view schematic illustration of a cover disc, according to an embodiment of the present invention.

FIG. 5b is a side view schematic illustration of a cover disc 11, according to an embodiment of the present invention.

Figure 5C:
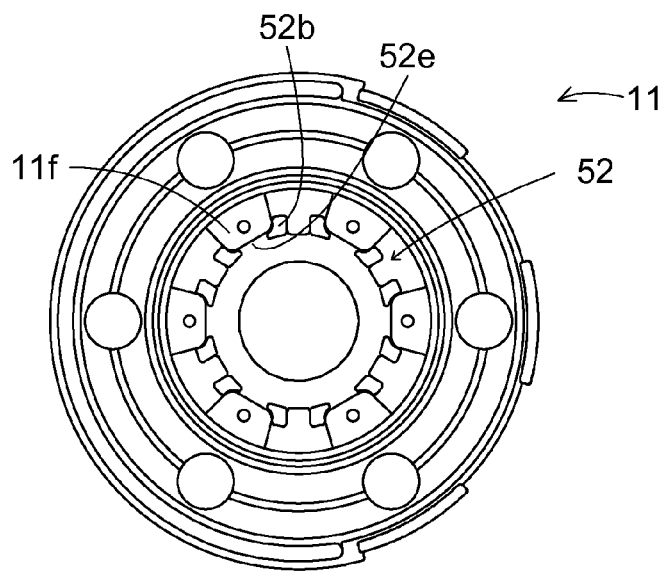
FIG. 5c is an isometric bottom view schematic illustration of a cover disc and lighting source supporter, according to an embodiment of the present invention.

FIG. 5c is an isometric bottom view schematic illustration of a cover disc 11 and lighting source supporter 52, according to an embodiment of the present invention.

In the configuration shown in the present illustration, the entire cover disc support 11f is within lighting source supporter wall 52b, conforming to a lighting source supporter wall groove 52e.

Figure 5D:
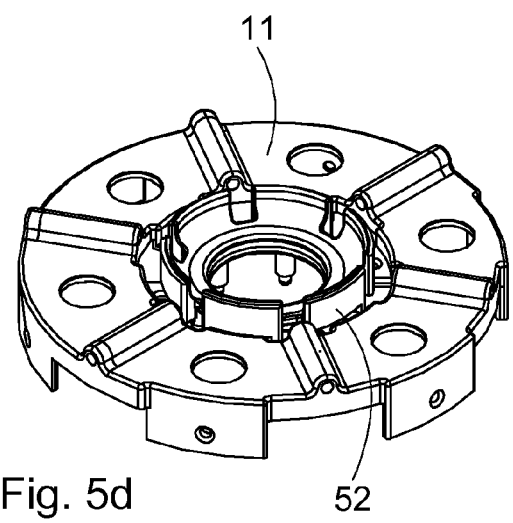
FIG. 5d is an isometric top view schematic illustration of a cover disc, and of lighting source supporter, according to an embodiment of the present invention.

FIG. 5d is an isometric top view schematic illustration of a cover disc 11, and of lighting source supporter 52, according to an embodiment of the present invention.

Both elements are engaged in each other, with their shapes and dimensions conforming for the purpose of this engagement.

Figure 6A:
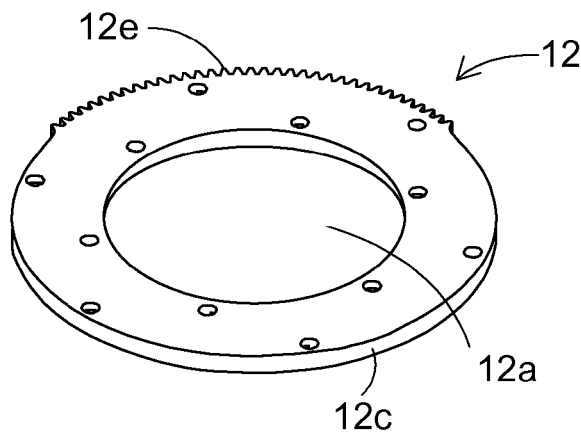
FIG. 6a is an isometric top view schematic illustration of a grooved disc, according to an embodiment of the present invention.

FIG. 6a is an isometric top view schematic illustration of a grooved disc 12, according to an embodiment of the present invention.

The grooved disc 12 is shaped like a flat ring, with a grooved disc central perforation 12a in its center, and a grooved disc outer surface 12c, some of which comprises grooved disc teeth 12e. The grooved disc teeth 12e serve the purpose of providing the grooved disc 12 with rotational movement.

Figure 6B:
FIG. 6b is side view schematic illustration of a grooved disc, according to an embodiment of the present invention.

FIG. 6b is side view schematic illustration of a grooved disc 12, according to an embodiment of the present invention.

Figure 6C:
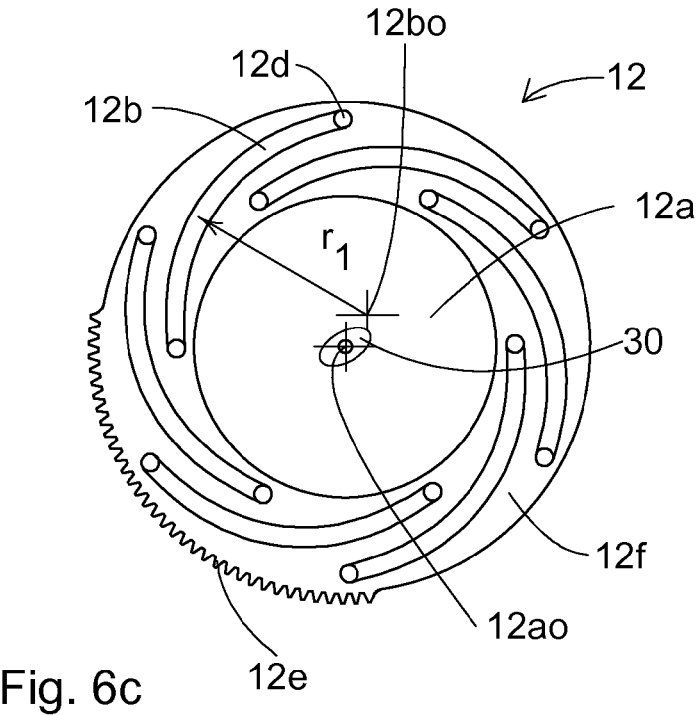
FIG. 6c is bottom view schematic illustration of a grooved disc and a central rod, according to an embodiment of the present invention.

FIG. 6c is bottom view schematic illustration of a grooved disc 12 and a central rod 30, according to an embodiment of the present invention.

This view shows curved grooves 12b whose depth, in the present case, is smaller than the thickness of the grooved disc 12, however can, in other configurations according to the present invention, be for the entire depth of the grooved disc 12. If the depth of the curved grooves 12b is smaller than the thickness of the grooved disc 12, grooved disc holes 12d can be added to facilitate a better flow of disinfectant material through them into the curved grooves 12b.

The grooved disc 12 serves for opening and closing the aperture created by the ribs 21 (not shown in the present illustration). Each curved groove 12b corresponds with one rib 21, and if all of the curved grooves 12b have the same curve shape, the distance of each rib 21 from the grooved disc central perforation center 12ao is consistently the same, in every state of rotation of the grooved disc 12, namely all of the ribs 21, at every cross section, are on a common circle.

According to another embodiment of the present invention, not all of the curved grooves 12b have the same curve shape. The curved grooves 12b can have many curve shapes. In the case shown in the present illustration, the curve shape of each one of them is a segment of a circle. When viewing the grooved disc 12, the groove radius origin 12bo is not at the same point as the grooved disc central perforation center 12ao.

The grooved disc central perforation center 12ao is practically positioned on the central rod tail symmetrical line 30s.

The grooved disc 12 has a grooved disc body 12f, whose general shape is that of a flat ring, on part of whose circumference are grooved disc teeth 12e.

Figure 7A:
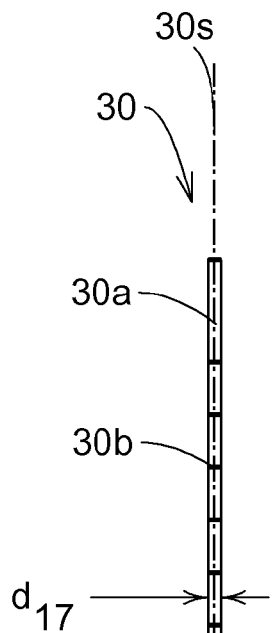
FIG. 7a is side view schematic illustration of a central rod, according to an embodiment of the present invention.

FIG. 7a is side view schematic illustration of a central rod 30, according to an embodiment of the present invention.

The central rod 30 has a central rod tail 30a, having a central rod tail diameter $d_{17}$ and in the configuration shown in the present illustration, it is slotted with central rod tail slots 30b, and has, at its end, central rod head dome 30c whose tip is tapered toward its end, from a side view.

The slots 30b serve the surgeon for the purpose of measuring penetration depth. For example, slots 30b can be marked at regular intervals of one centimeter each, and the measure of penetration can then be determined according to the numbers marked outside of the patient's body.

The central rod tail 30a has a central rod tail symmetrical line 30s. This line is disposed in a fixed location relative to the various components of the surgical retractor, according to the present invention, which do not move relative to each other when the central rod 30 is disposed between the ribs 21 (not shown in the present illustration), when they are in a closed mode, as they are at the beginning of insertion into the patient's body. This line can serve as a reference line for measurement of angles and distances, even when the central rod 30 is not in the position presently described.

The central rod 30 is designated as the leader guiding the penetration into the body of the operated patient. At the beginning of the procedure, it is centered between the ribs 21, (not shown in the present illustration), which are closed, while the central rod head dome 30c protrudes from them, and is first to come into contact with the operated patient's body.

The central rod 30 is taken out and removed from the operated area, after achieving sufficient opening of the ribs 21.

Figure 7B:
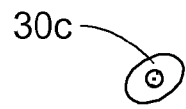
FIG. 7b is bottom view schematic illustration of a central rod head dome, according to an embodiment of the present invention.

FIG. 7b is bottom view schematic illustration of a central rod head dome 30c, according to an embodiment of the present invention.

In the configuration shown in the present invention, from a bottom view, the central rod head dome 30c has an oval shape; however it can have other shapes as well.

Figure 8A:
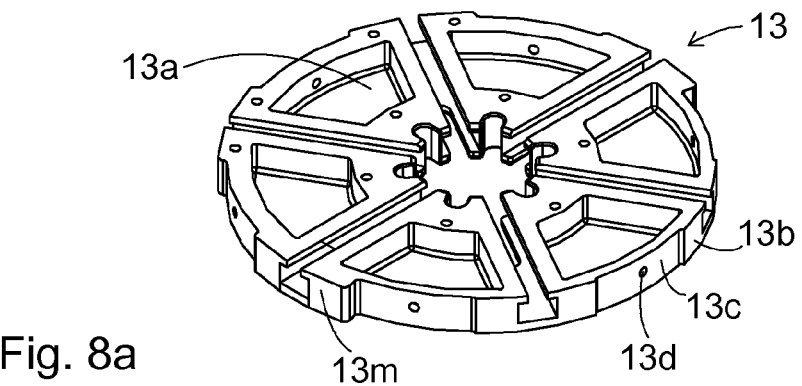
FIG. 8a is an isometric top view schematic illustration of a channeled disc, according to an embodiment of the present invention.

FIG. 8a is an isometric top view schematic illustration of a channeled disc 13, according to an embodiment of the present invention.

The channeled disc 13 includes a channeled disc base 13a, which has at its circumference the channeled disc wall 13b, which has several channeled disc wall niche 13c, as well as two channeled disc wall tenons 13m.

This shape of the circumference of the channeled disc 13 serves the purpose of conforming to other component at the time of assembly; however other shapes can also be used according to the present invention. Furthermore, for the purpose of connecting components, there are several channeled disc wall holes 13d, having internal screw threading.

Figure 8B:
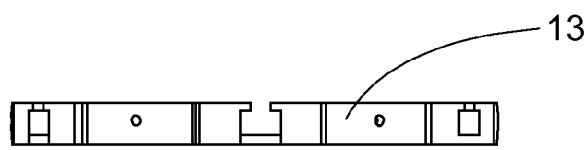
FIG. 8b is side view schematic illustration of a channeled disc, according to an embodiment of the present invention.

FIG. 8b is side view schematic illustration of a channeled disc 13, according to an embodiment of the present invention.

Figure 8C:
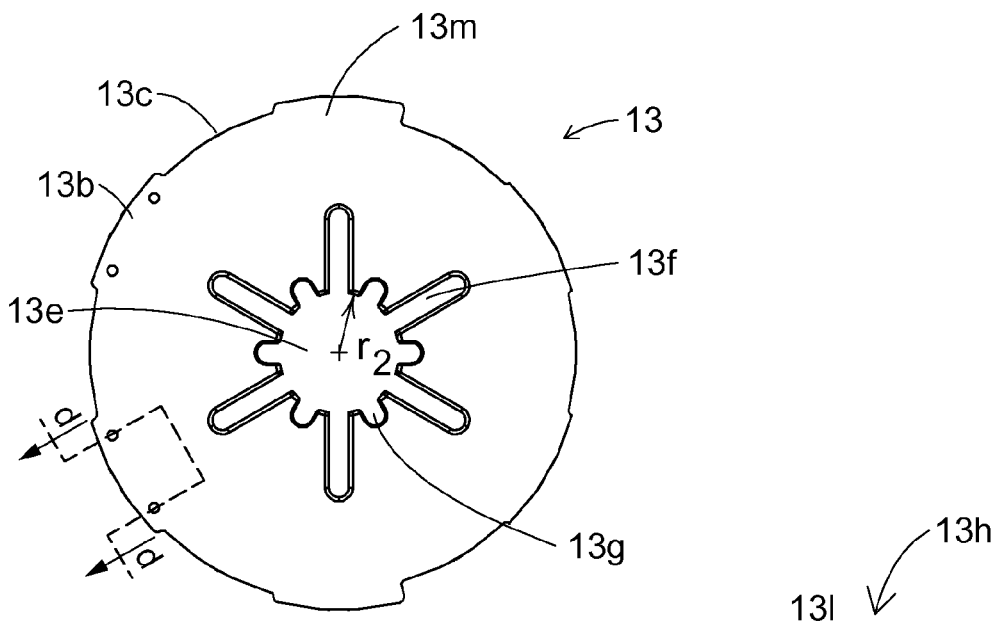
FIG. 8c is bottom view schematic illustration of a channeled disc, according to an embodiment of the present invention, upon which a section plane d-d is marked.

FIG. 8c is bottom view schematic illustration of a channeled disc 13, according to an embodiment of the present invention, upon which a section plane d-d is marked.

In the center of the channeled disc 13 is channeled disc perforation 13e, which is shaped as a circle having channeled disc perforation radius $r_2$. The channeled disc perforation radius $r_2$ disc is likely to be the element most limiting the maximal visual field of view that can be achieved during an operation, and the element most limiting the dimensions of the operating tools, therefore its size should preferably be no smaller than 15 millimeters.

The channeled disc 13 is slotted for its entire depth with channeled disc long slots 13f in order to enable positioning and movement of the ribs 21 (not shown in the present illustration), and in the channeled disc short slots 13g, which create cavities for the positioning of the lamps 51b.

Figure 8D:
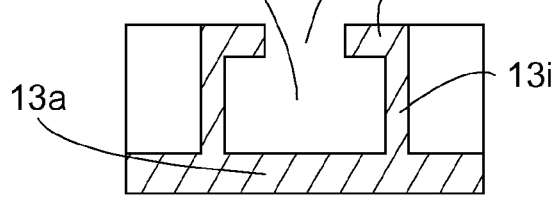
FIG. 8d is cross sectional view d-d illustration of a track, according to an embodiment of the present invention.

FIG. 8d is cross sectional view d-d illustration of a track 13h, according to an embodiment of the present invention.

The channeled disc 13 also engages a component that can make radial linear movement relative to a single point, the main slider 15 (which, along with other elements mentioned in the description of the present illustration, is not shown in the present illustration). For this purpose, the channeled disc 13 has tracks 13h. Every track 13h is closed on its bottom, in view of the orientation of the present illustration, by the channeled disc base 13a, on both of its sides by two track side walls 13i, and on its top by track upper wall 13j.

The track upper wall 13j has a channel upper opening 13l, which has suitable dimension for longitudinal movement of the slider upper body 15b. The space created between the elements described, as shown in the present illustration, comprises the channel 13k, whose dimensions are suitable for those of a main slider 15 so as to enable its radial longitudinal movement, and to prevent its movement in any other undesired direction.

Figure 9A:
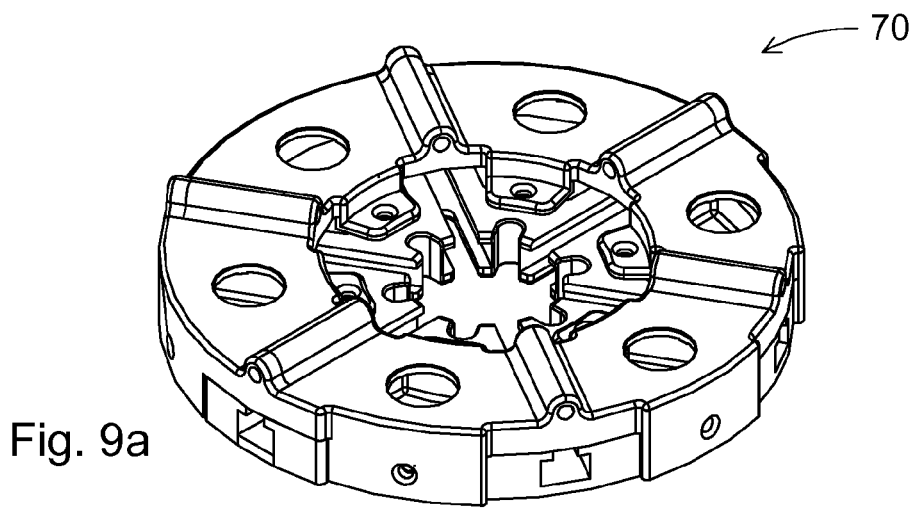
FIG. 9a is an isometric top view schematic illustration of casing, according to an embodiment of the present invention.

FIG. 9a is an isometric top view schematic illustration of casing 70, according to an embodiment of the present invention.

Figure 9B:
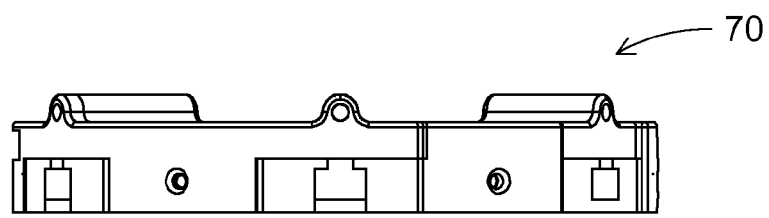
FIG. 9b is a side view schematic illustration of a casing, according to an embodiment of the present invention.

FIG. 9b is a side view schematic illustration of casing 70, according to an embodiment of the present invention.

Figure 9C:
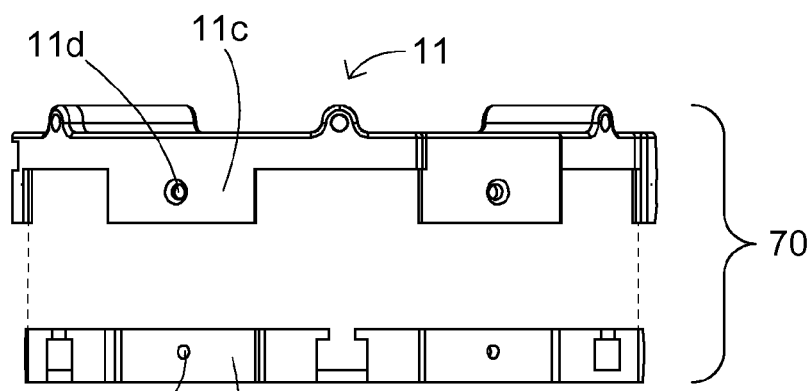
FIG. 9c is an exploded side view schematic illustration of casing, according to an embodiment of the present invention.

FIG. 9c is an exploded side view schematic illustration of casing 70, according to an embodiment of the present invention.

According to the embodiment shown in the present illustration, the engagement of the cover disc 11 with the channeled disc 13 is done by means of geometrically conforming both to each other, together forming a casing 70 suitable for carrying grooved disc 12 (not shown in the present illustration), and granting it smooth rotational movement, as well as for carrying and granting smooth movement of other components. The present illustration shows that the cover disc wall 11c and the cover disc wall hole 11d respectively conform with the channeled disc wall niche 13c and the channeled disc wall hole 13d, thus enabling a successful connection of the cover disc 11 with the channeled disc 13.

Figure 9D:
FIG. 9d is a side view schematic illustration of a casing bolt, according to an embodiment of the present invention.

FIG. 9d is a side view schematic illustration of a casing bolt 70a, according to an embodiment of the present invention.

Casing bolt 70a, one of which is shown in the present illustration magnified relative to the previous illustration, completes the connection of the cover disc 11 together with the channeled disc 13.

FIG. 10a is an isometric top view schematic illustration of a rib 21 and a main slider 15 combined together, according to an embodiment of the present invention.

All the ribs 21 and main sliders 15 are arranged in engaged pairs. Every main slider 15 is designated to linearly move one of the ribs 21.

Rib 21 has a rib back surface 21b and a rib front surface 21f. The rib front surfaces 21f of all the ribs 21 all face inwards relative to the spatial shape that they form together.

The rib back surface 21b and a rib front surface 21f are each divisible into several segments according to the structural parts of the type of rib 21 to which they belong.

FIG. 10b is an exploded isometric top view schematic illustration of a main slider 15, according to an embodiment of the present invention.

The main slider 15 includes a slider main body 15a, whose shape and dimensions are suitable for maintaining back and forth linear movement within a channel 13k, (not shown in the present illustration).

From the top part of the slider main body 15a, protrudes slider upper body 15b, whose shape and dimensions are suitable for maintaining back and forth linear movement within a channel upper opening 131, (not shown in the present illustration). Above slider upper body 15b, protrudes a slider pin 15i, whose shape and dimensions are suitable for maintaining back and forth linear movement within curved groove 12b, (not shown in the present illustration).

The slider pin 15i can be an integral part of the slider upper body 15b and of the slider main body 15a, or can be partially engaged within slider pin hole 15c.

The part of main slider 15 designated to be engaged with rib 21, (not shown in the present illustration), has two slider arms 15d, the space between which is suitable to contain a rib 21, so as to enable it rotational movement while preventing its lateral movement. Between both arms 15d is a slider pivot 15j, within two slider pivot holes 15e.

Between both slider arms 15d, is a perpendicularly disposed slider among arms surface 15f. At the bottom of the slider main body 15a, near the end farther from the slider arms 15d, is an optional slider niche 15g, within which is a slider friction reducer 15h that protrudes very slightly relative to the dimensions of the main slider 15, from beneath the main slider 15. The slider friction reducer 15h is composed of a material, such as silicone, having a smaller friction coefficient than the friction coefficient of the material, for example steel, composing the main slider 15.

FIG. 10c is a top view schematic illustration of a slider main body 15a, according to an embodiment of the present invention, upon which a section plane e-e is marked.

The present illustration shows a view from the top of the slider among arms surface 15f. Between both of the slider arms 15d, is a slider arms gap $d_{14}$.

FIG. 10d is a cross sectional view e-e illustration of a slider main body 15a, according to an embodiment of the present invention.

The present illustration indicates three dimensions of special significance for the purpose of conforming with a rib 21 (not shown in the present illustration), which are a slider pivot hole diameter $d_5$, a gap between the slider pivot and the slider among arms surface $d_6$ and a slider among arms surface radius $r_3$.

FIG. 10e is a partial side view illustration of a rib 21, according to an embodiment of the present invention.

The present illustration shows details and dimensions of special significance for the purpose of conforming with main slider 15, (not shown in the present illustration). A concave segment of a rib front surface 21a serves to transmit force during opening movement of rib 21 from the slider pivot 15j, (not shown in the present illustration). The preferred shape of concave segment of a rib front surface 21a is a half circle whose center is defined as a concave segment of a rib front surface origin 21o, having a concave segment of a rib front surface diameter $d_7$.

The convex segment of a rib back surface 21c has a section shape of a circle, whose center is concave segment of a rib front surface origin 21o, and which has a convex segment of a rib back surface radius $r_4$.

The maximum value of the convex segment of a rib back surface radius $r_4$ is at most equal to the value of the gap between the slider pivot and the slider among arms surface $d_6$ (not shown in the present illustration), so as to enable replacement of rib 21.

A rib shoulder 21d serves to transmit force from the slider main body 15a, (not shown in the present illustration) in order to perform closing. Part of rib shoulder 21d has a rib shoulder concave segment 21e, having a rib shoulder concave segment radius $r_5$.

The value of the rib shoulder concave segment radius $r_5$ corresponds with the slider among arms surface radius $r_3$ (not shown in the present illustration).

FIG. 10f is a partial side view illustration of a rib 21 and a main slider 15, according to an embodiment of the present invention.

The present illustration shows a state of movement toward opening 15o, in which the slider pivot 15j is moving to the right, in the orientation shown in the present illustration, and applies force to rib 21 in the area of contact with the concave segment of a rib front surface 21a.

FIG. 10g is a partial side view illustration of a rib 21 and a main slider 15, according to an embodiment of the present invention.

The present illustration shows a state of movement toward closing 15cl, in which main slider 15 moves to the left, in the orientation shown in the present illustration, and applies force, to rib 21 in the area of contact with the slider among arms surface 15f, which acts on the rib shoulder 21d. The rib shoulder 21d, also limits the rotational movement of rib 21 clockwise, according to the view shown in the present illustration, prevention of the rotational movement occurs during contact between the rib shoulder 21d with the slider among arms surface 15f.

Figure 10H:
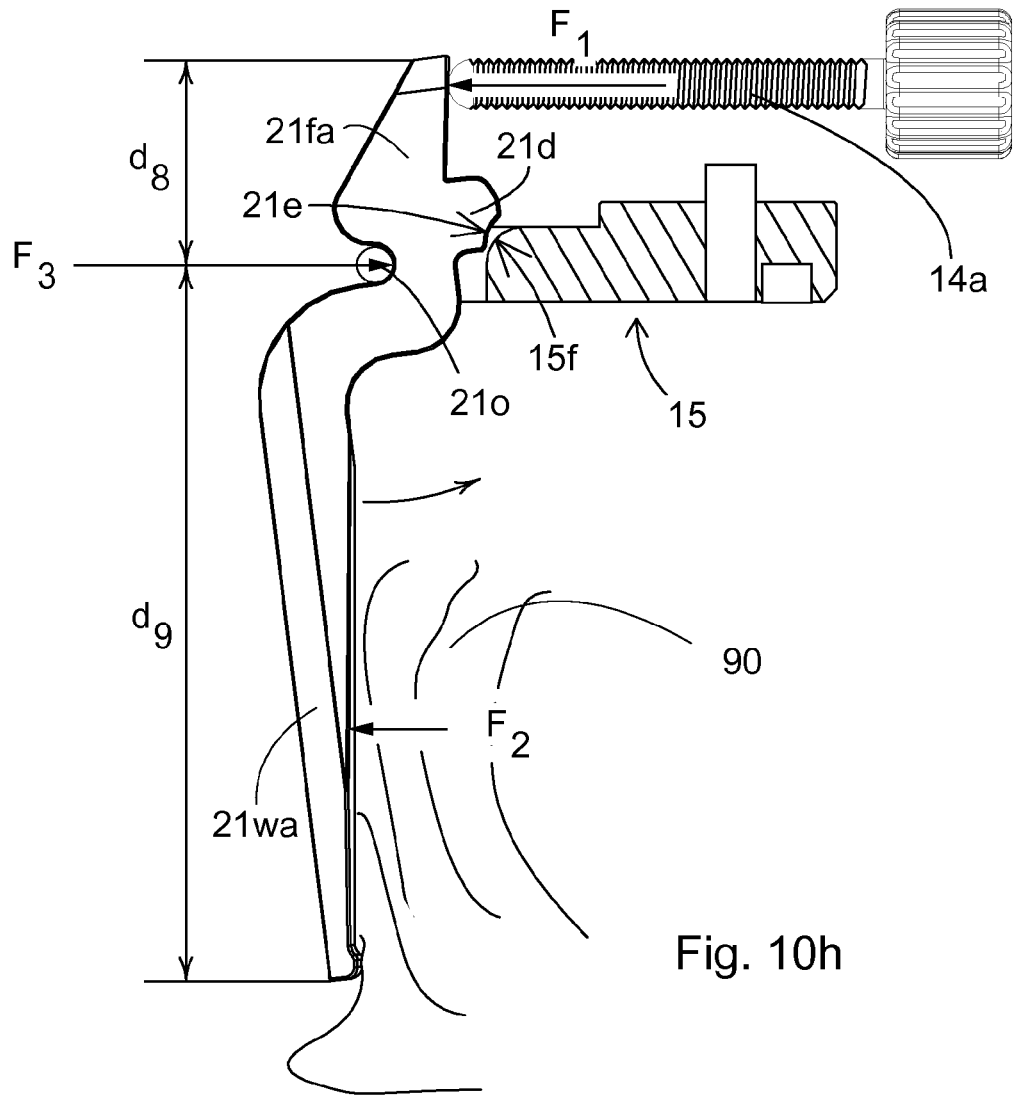
FIG. 10h is a side view illustration of a rib, an angular adjustment bolt and a main slider, partially sectioned, according to an embodiment of the present invention.

FIG. 10h is a side view illustration of a rib 21, an angular adjustment bolt 14a and a main slider 15, partially sectioned, according to an embodiment of the present invention.

The present illustration describes forces affecting rib 21 when it is inside the operated patient's body when body tissue 90 applies pressure to it, the resultant force of which, the body tissue force $F_2$, is applied to a specific point on a rib working arm 21wa of the rib 21. Conversely, in the state shown in the present illustration, the angular adjustment bolts 14a applies adjustment bolt force $F_1$ on a rib force arm 21fa. Both the adjustment bolt force $F_1$ and the body tissue force $F_2$ are balanced by a slider pivot force $F_3$, which is applied in the opposite direction.

The concave segment of a rib front surface origin 210 comprises a possible rotational center for rib 21, and its location determines which part of the rib 21 acts as the rib working arm 21wa and which acts as the rib force arm 21fa.

Furthermore, when the angular adjustment bolts 14a applies adjustment bolt force $F_1$ to the rib force arm 21fa, rib 21 rotates counterclockwise, in the view shown in the present illustration, and a gap is formed between the rib shoulder concave segment 21e and the slider among arms surface 15f.

The rib force arm 21fa has a rib force arm length $d_8$ and the rib working arm 21wa has a rib working arm length $d_9$.

Figure 10I:
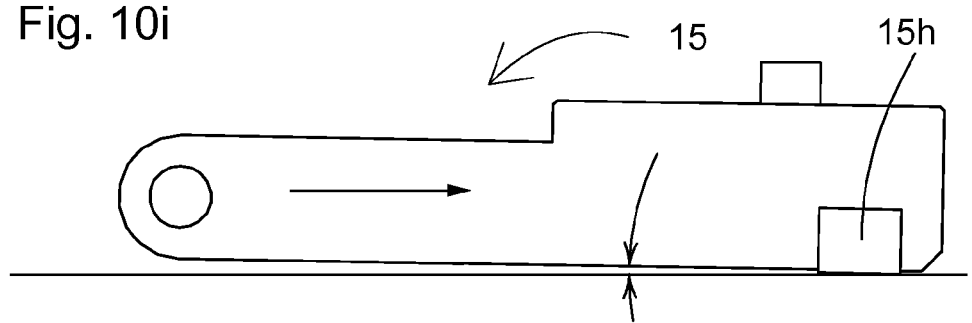
FIG. 10i is a side view illustration of a main slider, according to an embodiment of the present invention.

FIG. 10i is a side view illustration of a main slider 15, according to an embodiment of the present invention.

When the main slider 15 moves toward opening, to the right in the orientation of the present illustration, angle $\alpha$ is formed between the slider and the channeled disc and the contact between main slider 15 with the surface upon which it moves is only in the area of the slider friction reducer 15h.

Figure 11:
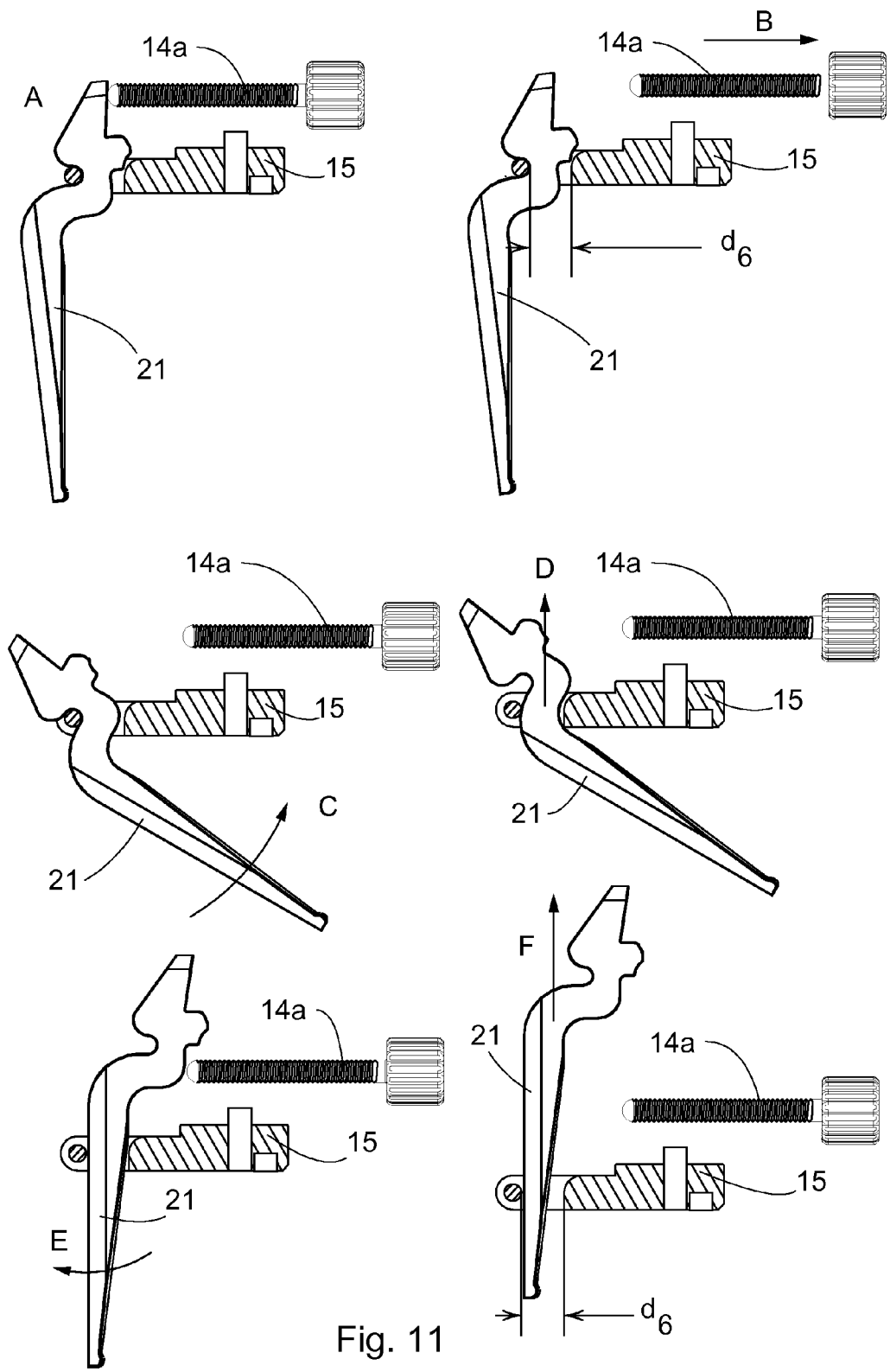
FIG. 11 is a side view illustration of a rib, an angular adjustment bolt and a main slider, partially sectioned, in six stages of separation, according to an embodiment of the present invention.

FIG. 11 is a side view illustration of a rib 21, an angular adjustment bolt 14a and a main slider 15, partially sectioned, in six stages of separation, according to an embodiment of the present invention.

These stages are part of a method for replacing rib 21, and they demonstrate the manner of removing rib 21 from its place, from a state suitable for operation, engaged with main slider 15. Similarly, but with reversal of the order of stages, rib 21 is engaged with a main slider 15.

The stages are:

Starting (stage A), showing one possible starting state, in which the angular adjustment bolt 14a is in contact with rib 21;

retreating of the angular adjustment bolt 14a (stage B);
rotating clockwise of the rib 21 (stage C);
pulling up the rib 21 as much as possible (stage D)
rotating counter-clockwise of the rib 21 (stage E); and
separating the rib 21 from the main slider 15 by pulling up the rib 21 all the way out (stage F).

In order to enable this removal there cannot be any width dimension of rib 21, required to go through the gap between the slider pivot and the slider among arms surface $d_6$, which is wider than this gap.

Figures 12A, 12B:
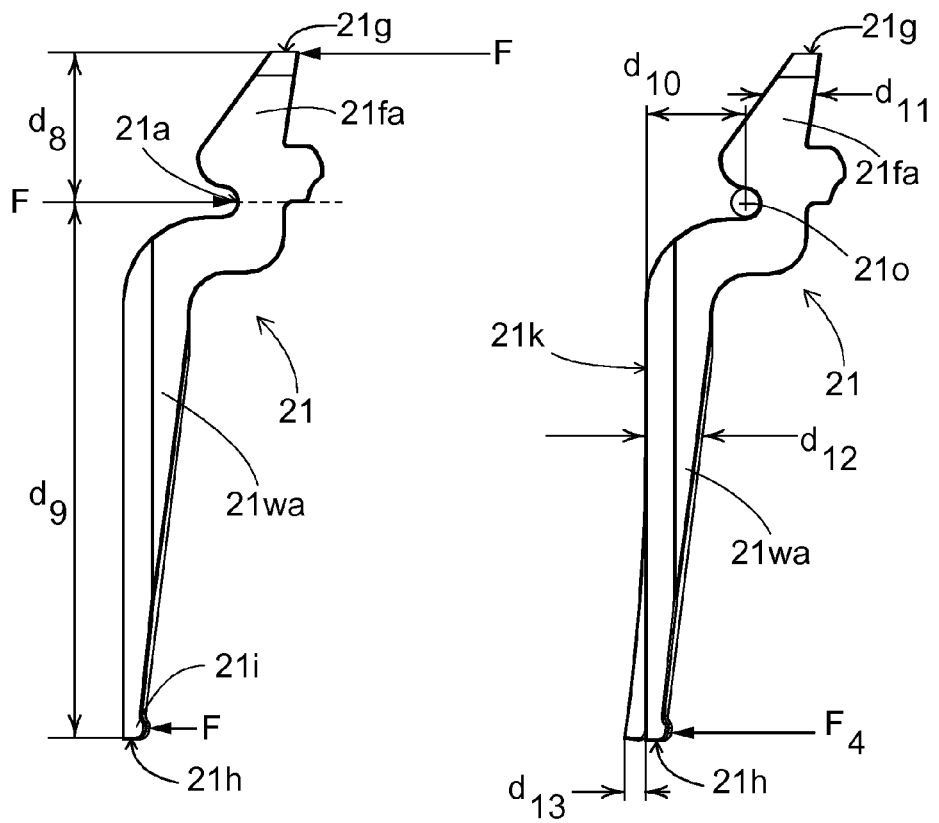
FIG. 12a is a side view illustration of a rib, according to an embodiment of the present invention.
FIG. 12b is a side view illustration of a rib, according to an embodiment of the present invention.

FIG. 12a is a side view illustration of a rib 21, according to an embodiment of the present invention.

The present illustration shows the division of the rib 21 into two arms. In a state in which the concave segment of a rib front surface 21a practically serves as a support point and both ends, the rib bottom end 21h and the rib top end 21g, are subject to forces F, which are horizontal according to the orientation of the present illustration; the part of rib 21 in which there is a counterclockwise twisting effort is defined as rib force arm 21fa and the part in which there is a clockwise twisting effort is defined as rib working arm 21wa.

Close to the rib bottom end 21h, there is a rib bottom end projection 21i, which is designated to facilitate prevention of rib 21 being pushed outward and upward as a result of forces applied to it by the operated patient's body tissue.

FIG. 12b is a side view illustration of a rib 21, according to an embodiment of the present invention.

The present illustration defines additional features of rib 21. Rib 21, according to an embodiment of the present invention, is practically rigid, considering the forces that may be applied to it during performance of an operation on a human body. The term "rigid" is to indicate that the rib practically does not bend, or deflect, when a reasonable force, moment, or torque from the tissue is applied. Proper design and production of rib 21 with use of suitable materials such as steel or titanium, can ensure meeting the required test criterion for a rib 21 having a rib working arm length $d_9$ and a maximum rib bottom end deflection $d_{13}$, under the activation of test force $F_4$ at a predefined level on the rib bottom end 21h, with the rib force arm 21fa harnessed.

A practical example of such a test is the following data:
rib working arm length $d_9$: 60 centimeter;
test force $F_4$: 200 Newton; and
maximum rib bottom end deflection $d_{13}$: 0.4 millimeter.

One effective way of obtaining the required rigidity, without adding unnecessary weight, is by selecting a shape in which rib working arm 21wa has a rib working arm width $d_{12}$ having a size that tapers toward the rib bottom end 21h.

Similarly to rib force arm 21fa, there is a rib force arm width $d_{11}$, which tapers toward rib top end 21g.

Another feature is the rib working arm projection to the center $d_{10}$, which is designated to remove the rib force arm 21fa from the doctor's visual field. The value of the rib working arm projection to the center $d_{10}$ should preferably be at least 10 millimeters, when this distance is measured from the concave segment of a rib front surface origin 21o, perpendicular to the plane on which rib working arm front surface 21k is disposed.

Figure 12C:
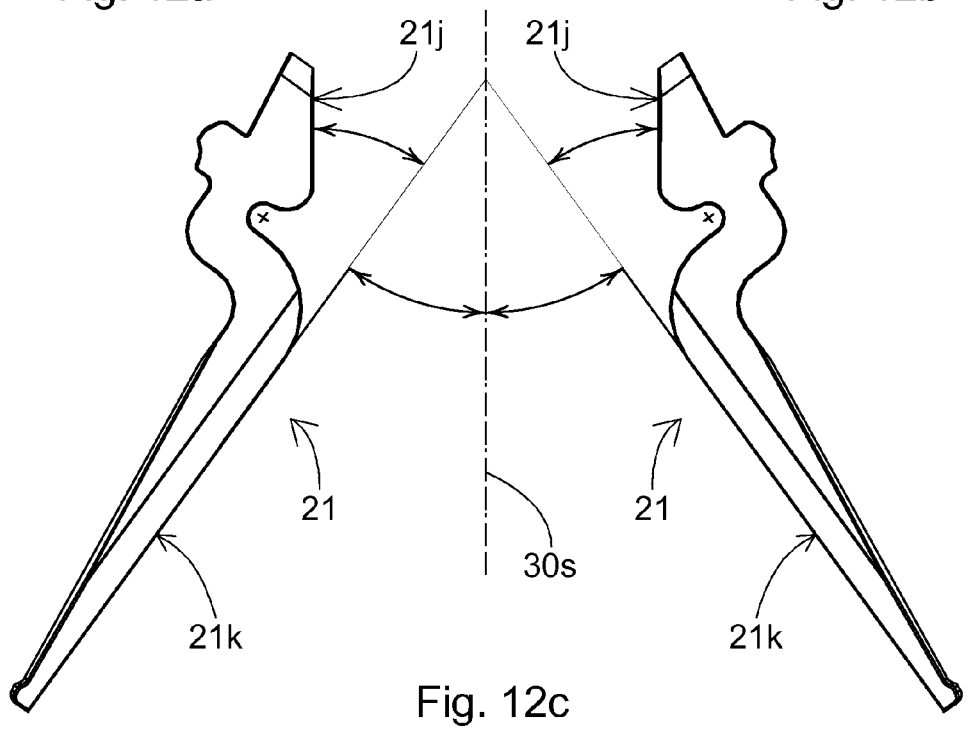
FIG. 12c is a side view illustration of two ribs, according to an embodiment of the present invention.

FIG. 12c is a side view illustration of two ribs 21, according to an embodiment of the present invention.

The two ribs 21 in the present case are on the same plane and are shown as minor images of each other.

Rib 21 has a rib force arm front surface 21j and a rib working arm front surface 21k, which are for most of their lengths in side view, straight. The present illustration shows each one of both ribs 21 at a rib opening angle δ at which the rib force arm front surface 21j is parallel to a symmetry line between both ribs 21. In this state, the angle between the rib force arm front surface and the rib working arm front surface β is equal to rib opening angle δ.

The rib opening angle δ is measured between the symmetrical line 30s and the rib working arm front surface 21k.

Figure 13A:
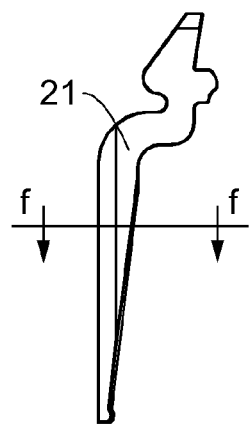
FIG. 13a is a side view illustration of a rib, according to an embodiment of the present invention, upon which a section plane f-f is marked.

FIG. 13a is a side view illustration of a rib 21, according to an embodiment of the present invention, upon which a section plane f-f is marked.

Figure 13B:
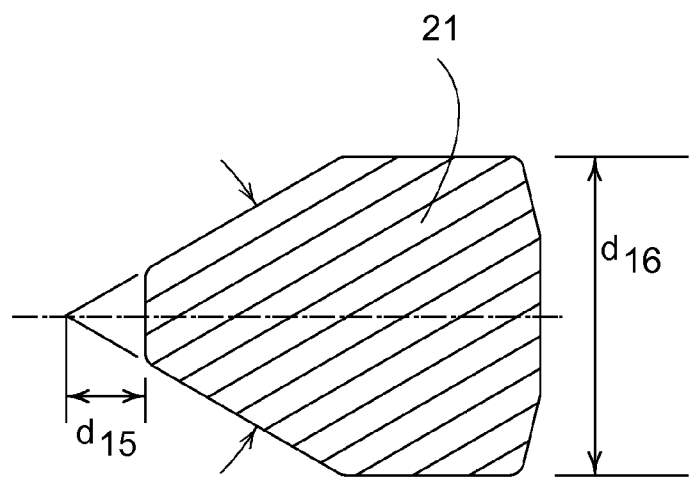
FIG. 13b is a cross sectional view f-f illustration of a rib, according to an embodiment of the present invention.

FIG. 13b is a cross sectional view f-f, view illustration of a rib 21, according to an embodiment of the present invention.

Rib 21 has a rib thickness $d_{16}$, which conforms to the dimensions of the slider arms gap $d_{14}$, so as to enable rotational movement between the two, but to enable practically no sideways movement of rib 21. The side of the section facing forwards is tapered, and has a rib cross section head angle γ, a preferred value of which is 360 degrees divided by the number of ribs 21 included in the retractor. The tapered part end is cut off, and has a rib cross section head cut off length $d_{15}$.

Figure 13C:
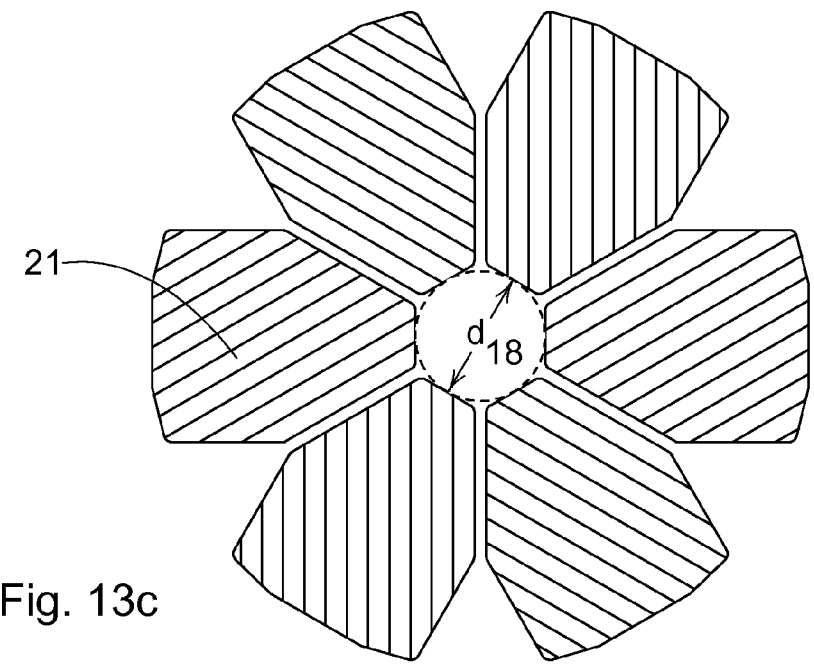
FIG. 13c is six cross sectional views f-f illustration of six ribs, according to an embodiment of the present invention.

FIG. 13c is six cross sectional views f-f illustration of six ribs 21, according to an embodiment of the present invention.

According to an embodiment of the present invention the retractor includes six ribs 21, however other numbers can be used.

The ribs 21 are shown in the present illustration in a state referred to in the present invention as a closed state, and each one touches the adjacent ones for most of its length rib working arm 21wa (not shown in the present illustration). In this closed state, the ribs 21 bind an internal circle (dashed line in the illustration), having a ribs interior diameter $d_{18}$, which conforms to the dimensions of the central rod tail diameter $d_{17}$.

Figure 14A:
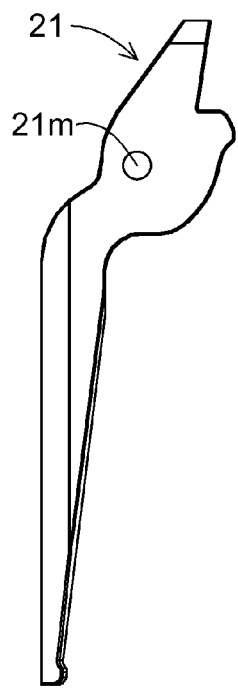
FIG. 14a is a side view illustration of a rib, according to an embodiment of the present invention.

FIG. 14a is a side view illustration of a rib 21, according to an embodiment of the present invention.

According to an embodiment of the present invention, the rib 21 includes a rib hole 21m. The rib hole 21m is assembled such that a slider pivot 15j (not shown in the present illustration) is engaged within it, and their dimensions conform so as to enable effective rotational movement between both.

According to this embodiment, replacement of a rib 21 requires removing and then reinserting the slider pivot 15j (not shown in the present illustration) in place.

Figure 14B:
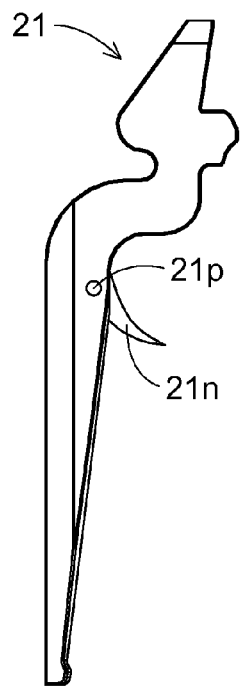
FIG. 14b is a side view illustration of a rib with a rib hook, according to an embodiment of the present invention.

FIG. 14b is a side view illustration of a rib 21 with a rib hook 21n, according to an embodiment of the present invention.

In order to prevent penetration of the patient's skin into the wound cavity, the rib 21, according to an embodiment of the present invention, is equipped with a rib hook 21n. In order to prevent the addition of the rib hook 21n from hampering the replacement of rib 21, the rib hook 21n must either be sufficiently small, detachable from the rib 21, or foldable, for example around rib hook pin 21p, in this case, the rotation ability is upward, in the orientation shown in the present illustration, while downward rotation is not possible beyond the state shown in the illustration.

Figure 14C:
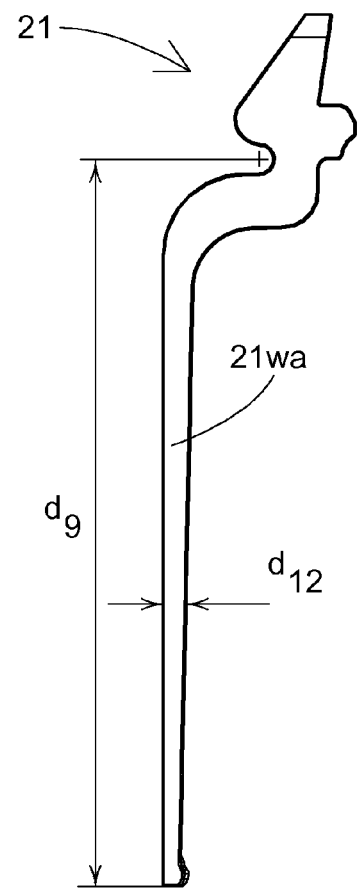
FIG. 14c is a side view illustration of a rib, according to an embodiment of the present invention.

FIG. 14c is a side view illustration of a rib 21, according to an embodiment of the present invention.

According to an embodiment of the present invention, the rib 21 is somewhat flexible, and does not need to meet the definition and test requirement for rigidity given with regard to the description of FIG. 12b. As such, the rib working arm length $d_9$ can have a relatively high value, and there is no requirement for any large change in values of rib working arm width $d_{12}$ according to their positions along the rib working arm 21wa, to the extent that their values can be fixed.

Figure 14D:
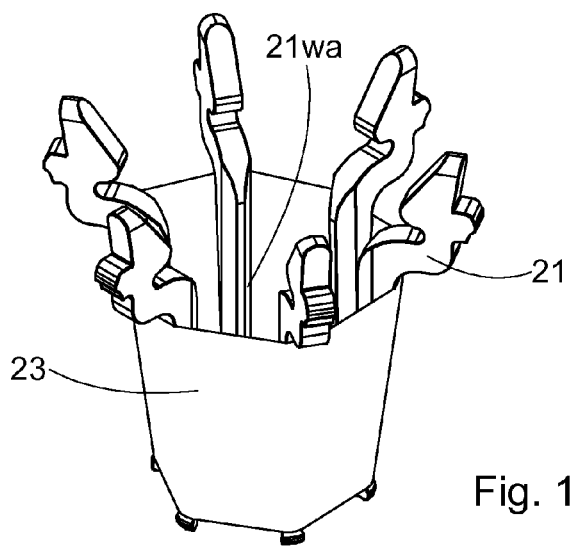
FIG. 14d is an isometric view illustration of six ribs, and a flexible sleeve, according to an embodiment of the present invention.

FIG. 14d is an isometric view illustration of six ribs 21, and a flexible sleeve 23, according to an embodiment of the present invention.

The flexible sleeve 23 externally encases the six ribs 21 along their rib working arms 21wa, for their entire length or part of it, and is designated to prevent tissue from entering the opening created for the purpose of performing the medical procedure.

The material composing the flexible sleeve 23 can be polyisoprene, a natural polymer, for example, however this material is in no way limiting the present invention.

Polyisoprene is strong and elastic, is transparent after expansion, is inert, and does not cause allergic reactions.

Figure 14E:
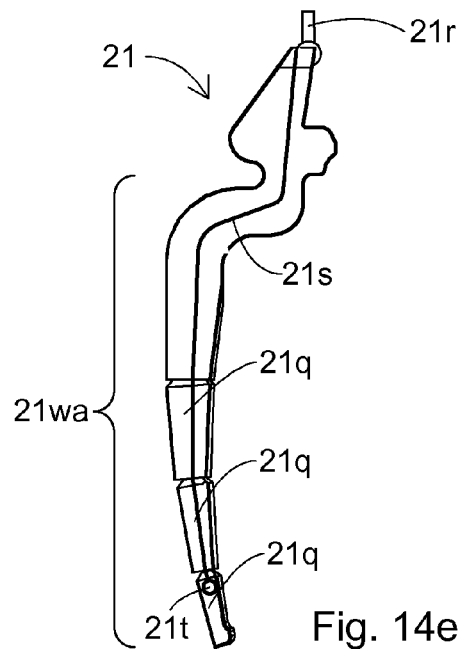
FIG. 14e is a side view illustration of a rib having rib segments, in a relaxed state, according to an embodiment of the present invention.

FIG. 14e is a side view illustration of rib 21, having rib segments 21q, in a relaxed state, according to an embodiment of the present invention.

The rib working arm 21wa of the rib 21 is divided into several rib segments 21q, three in the case of the present illustration.

A cable 21s is connected at one end to an anchoring point 21t, disposed within the lower rib segment 21q.

The cable 21s is shown in the present illustration as if running through a series of perforations for the length of all parts of a transparent rib 21 and connects at the other end to a cable tensioner 21r. When the cable tensioner 21r is in a proper state, the cable 21s is relaxed and enables minimal distancing of the rib segments 21q from each other, thus enabling creation of a rotational angle in any direction, if there is no specific device to limit it, between every pair of adjacent rib segments 21q. Even though the present illustration shows only one cable 21s and only one cable tensioner 21r, this is in no way limiting the present invention, and different quantities of these elements are also possible.

Figure 14F:
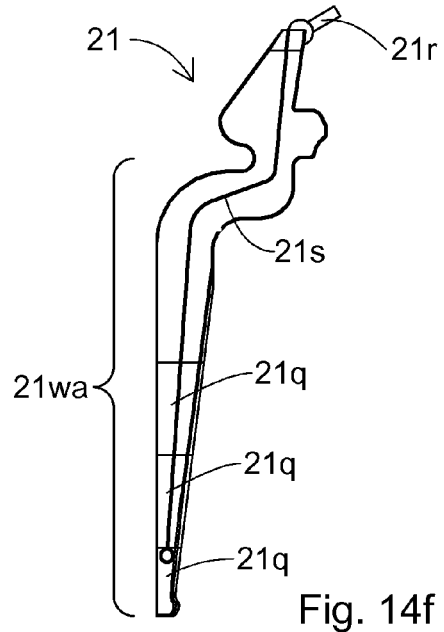
FIG. 14f is a side view illustration of rib having rib segments, in a flexed state, according to an embodiment of the present invention.

FIG. 14f is a side view illustration of rib 21, having rib segments 21q, in a flexed state, according to an embodiment of the present invention.

The cable tensioner 21r applies tensioning force on the cable 21s, thus causing the rib segments 21q to join so as to create the desired external shape of rib 21.

The cable 21s must be composed of a sufficiently strong material such as carbon nanotubes.

Figure 14G:
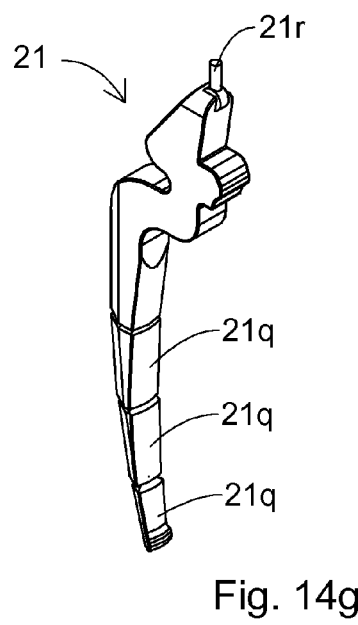
FIG. 14g is an isometric view illustration of a rib, having rib segments, in a relaxed state, according to an embodiment of the present invention.

FIG. 14g is an isometric view illustration of a rib 21, having rib segments 21q, in a flexed state, according to an embodiment of the present invention.

Figure 14H:
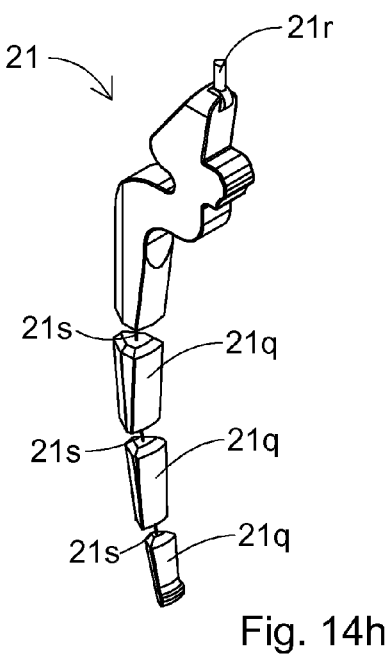
FIG. 14h is an isometric view illustration of a rib, having rib segments, in a relaxed state, according to an embodiment of the present invention, with the rib segments distanced from each other.

FIG. 14h is an isometric view illustration of rib 21, having rib segments 21q, in a relaxed state, according to an embodiment of the present invention, with the rib segments 21q distanced from each other.

The distances between the rib segments 21q shown in the present illustration are exaggerated, for the purpose of demonstrating the upper part of each rib segment 21q, which is one of many possible shapes enabling partial engagement of each rib segment 21q in the lower part of the rib segments 21q above it. The present invention is not limited to any specific number of rib segments 21q, or any specific position of them.

Figure 15A:
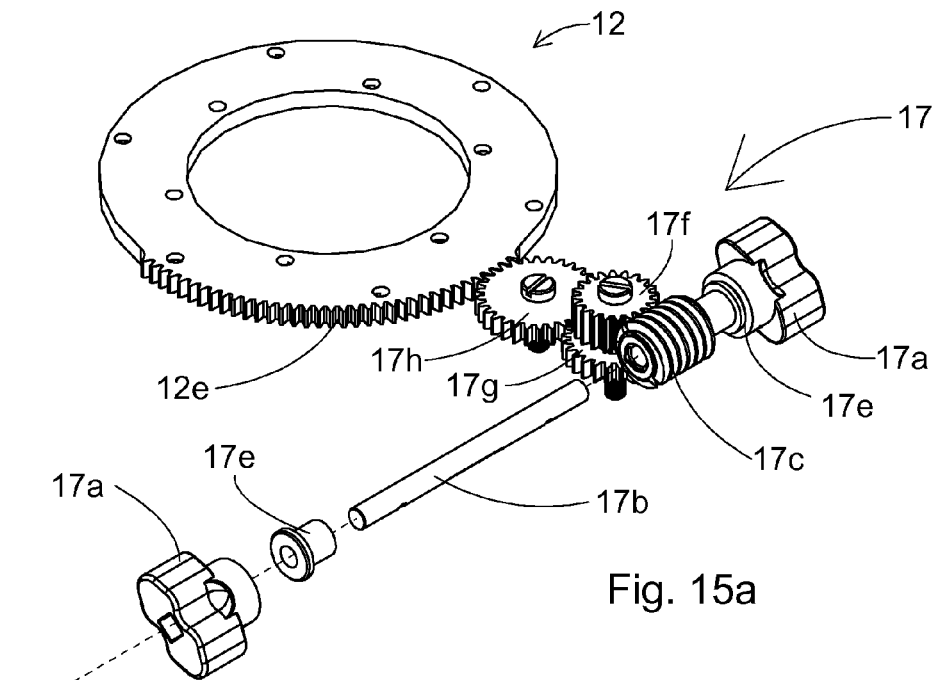
FIG. 15a is an isometric top view illustration of a transmission, partially exploded, according to an embodiment of the present invention.

FIG. 15a is an isometric top view illustration of a transmission 17, partially exploded, according to an embodiment of the present invention.

The transmission 17 is designated to grant rotational movement to grooved disc 12. The movement starts with manual rotation of at least one of the two transmission knobs 17a, which transmit rotational movement through a transmission tubular 17e to a transmission shaft 17b, and through that to a transmission worm 17c. The transmission worm 17c rotates a transmission first cog wheel 17f, which is rigidly connected on a shaft with a transmission second cog wheel 17g. The transmission second cog wheel 17g rotates a transmission third cog wheel 17h, which, at the end of the process, grants the necessary rotational movement to grooved disc 12 by means of the grooved disc teeth 12e. The engagement of the transmission first cog wheel 17f by rigid connection on a shaft with the transmission second cog wheel 17g is for the purpose of obtaining the desired transmission ratio, and to provide a convenient distance for users' hands when forming the opening operation.

Use of the transmission third cog wheel 17h, other than its effect on the transmission ratio, is to distance the transmission knobs 17a from the grooved disc 12.

Figure 15B:
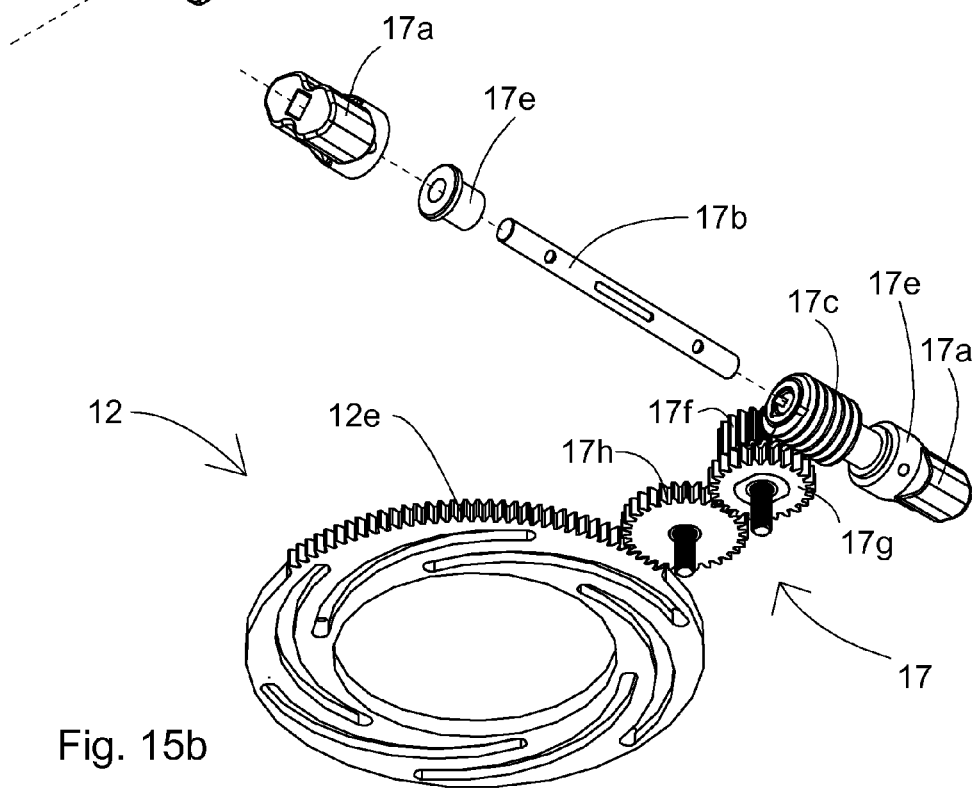
FIG. 15b is an isometric bottom view illustration of a transmission, partially exploded, according to an embodiment of the present invention.

FIG. 15b is an isometric bottom view illustration of a transmission 17, partially exploded, according to an embodiment of the present invention.

This transmission can enable controlled opening at a slow rate of 50 micrometers per second by applying force of the fingers.

According to the present invention, transmission systems of various different structures can be used. Likewise, a suitable mechanical engine can be used instead of manual force.

Figure 16A:
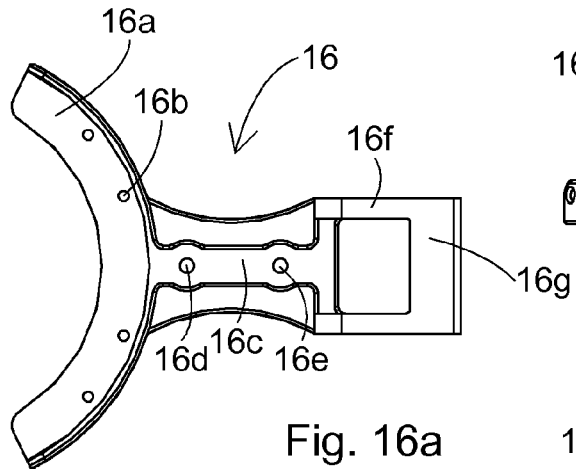
FIG. 16a is a top view illustration of a carrier, according to an embodiment of the present invention.

FIG. 16a is a top view illustration of a carrier 16, according to an embodiment of the present invention.

The carrier 16 includes a carrier bow 16a, a carrier bridge 16c, two carrier arms 16f, and a carrier back wall 16g.

The carrier 16 connects the channeled disc 13 with the adaptor 40 (both not shown in the present illustration), and carries the transmission 17, (not shown in the present illustration).

Carrier bow 16a has carrier bow bottom holes 16b and carrier bow side holes 16i (not shown in the present illustration), for the purpose of connection to the channeled disc 13 (not shown in the present illustration).

In the carrier bridge 16c there are two holes, a carrier bridge first hole 16d, designated to carry the shaft of the transmission third cog wheel 17h, (not shown in the present illustration) and a carrier bridge second hole 16e, designated to carry the common shaft of the transmission first cog wheel 17f and the transmission second cog wheel 17g (both not shown in the present illustration).

Figure 16B:
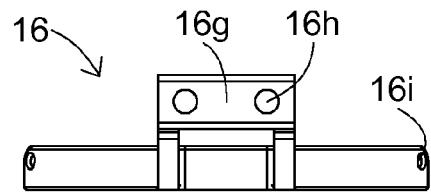
FIG. 16b is a back view illustration of a carrier, according to an embodiment of the present invention.

FIG. 16b is a back view illustration of a carrier 16, according to an embodiment of the present invention.

Carrier back wall holes 16h in the carrier back wall 16g are designated for connection to the adaptor rods 40a (not shown in the present illustration).

Figure 16C:
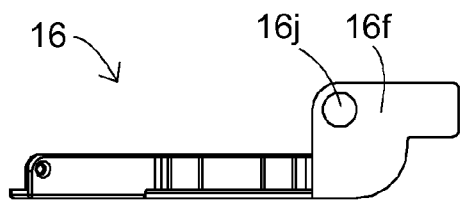
FIG. 16c is a side view illustration of a carrier, according to an embodiment of the present invention.

FIG. 16c is a side view illustration of a carrier 16, according to an embodiment of the present invention.

The transmission shaft 17b (not shown in the present illustration), in an assembled state, runs through carrier arm hole 16j in the two carrier arms 16f.

Figure 16D:
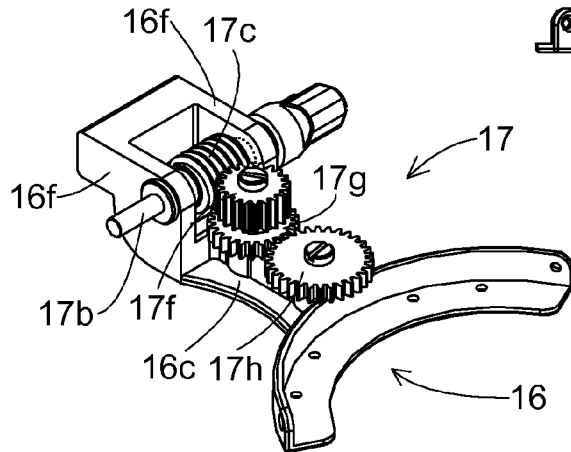
FIG. 16d is an isometric top view illustration of a carrier, and a transmission, according to an embodiment of the present invention.

FIG. 16d is an isometric top view illustration of a carrier 16, and a transmission 17, according to an embodiment of the present invention.

One transmission knob 17a is not shown in the present illustration. The transmission worm 17c is mounted upon the transmission shaft 17b, between both carrier arms 16f.

The transmission first cog wheel 17f, the transmission second cog wheel 17g and the transmission third cog wheel 17h are mounted above the carrier bridge 16c, according to the orientation of the present illustration.

Figure 16E:
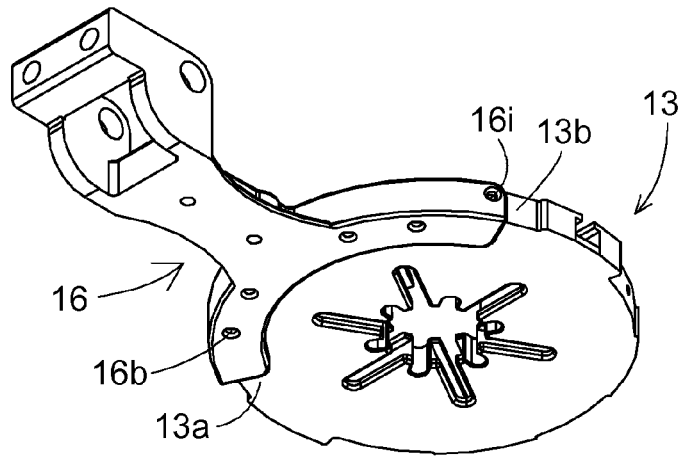
FIG. 16e is an isometric bottom view illustration of a carrier, and a channeled disc, according to an embodiment of the present invention.

FIG. 16e is an isometric bottom view illustration of a carrier 16, and a channeled disc 13, according to an embodiment of the present invention.

Their joint connection can be by means of screws through the carrier bow bottom holes 16b and the carrier bow side holes 16i. The screws can be such as the casing bolts 70a, (not shown in the present illustration), with suitable holes, having internal screw threading in the channeled disc base 13a and the channeled disc wall 13b.

Figure 17A:
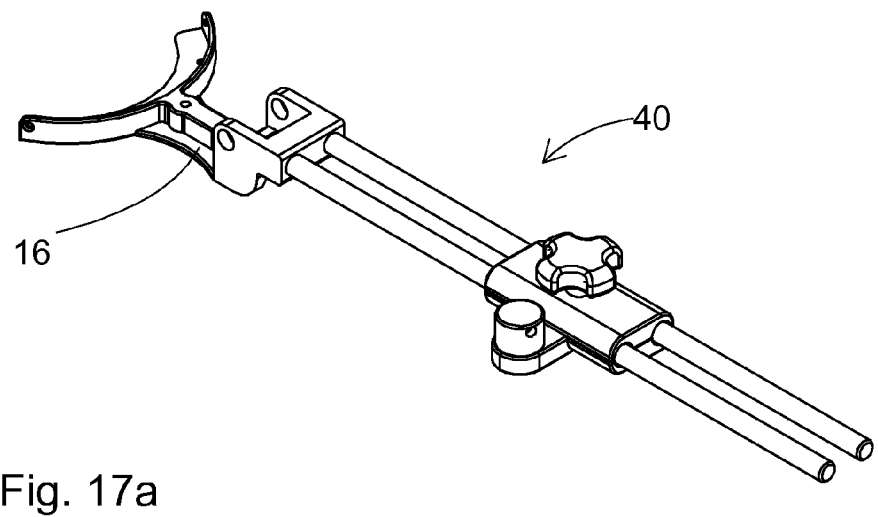
FIG. 17a is an isometric top view illustration of a carrier, and an adaptor, according to an embodiment of the present invention.

FIG. 17a is an isometric top view illustration of a carrier 16, and an adaptor 40, according to an embodiment of the present invention.

Figure 17B:
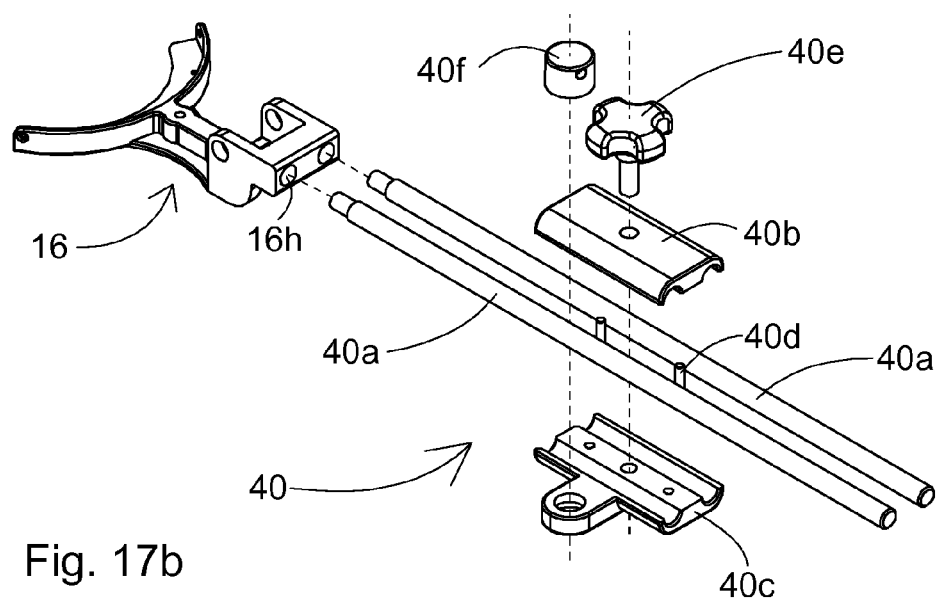
FIG. 17b is an exploded isometric top view illustration of a carrier, and an adaptor, according to an embodiment of the present invention.

FIG. 17b is an exploded isometric top view illustration of a carrier 16, and an adaptor 40, according to an embodiment of the present invention.

Figure 18A:
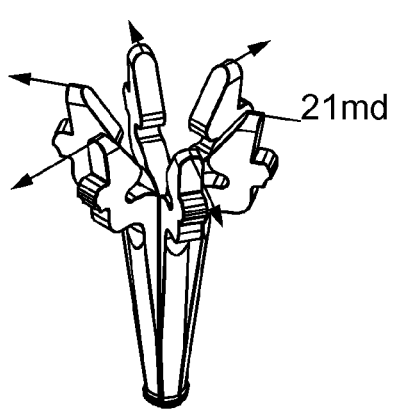
FIG. 18a is an isometric top view illustration of six ribs, in a closed state, according to an embodiment of the present invention.

FIG. 18a is an isometric top view illustration of six ribs 21 in a closed state, according to an embodiment of the present invention.

The number of ribs 21 shown in the present illustration is six, however this is not limiting the present illustration specifically to this number. In this state, the ribs 21 are inserted into the operated patient's body, while they are as tightly close to each other as possible, thus creating an entry puncture of the smallest diameter that can be achieved with them. This diameter, which is determined by the widest section created by the six ribs 21, should preferably be no larger than 8 mm, while in any case the diameter should be as small as it enabled by the mechanical strength of the ribs 21.

The arrows at the upper part of the present illustration indicate movement directions 21md of each one of the ribs 21, if linear opening is required.

Figure 18B:
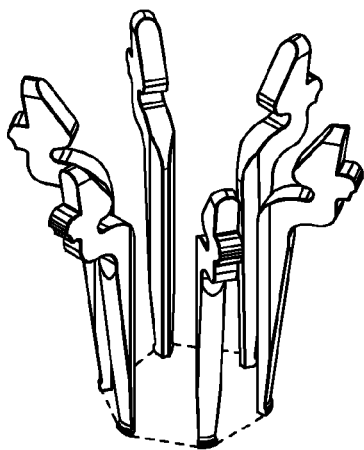
FIG. 18b is an isometric top view illustration of six ribs, in an opened state, according to an embodiment of the present invention.

FIG. 18b is an isometric top view illustration of six ribs 21 in an open state, according to an embodiment of the present invention.

The opening performed in order to achieve this state was with uniform linear movement of each one of the six ribs 21, such that all six are, at every possible lateral section, on a circle together.

Figure 18C:
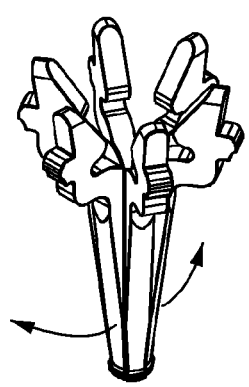
FIG. 18c is an isometric top view illustration of six ribs, in a closed state, according to an embodiment of the present invention.

FIG. 18c is an isometric top view illustration of six ribs 21 in a closed state, according to an embodiment of the present invention.

The arrows at the lower part of the illustration indicate the possibility of rotational movement 21rm of ribs 21, two in this case.

Figure 18D:
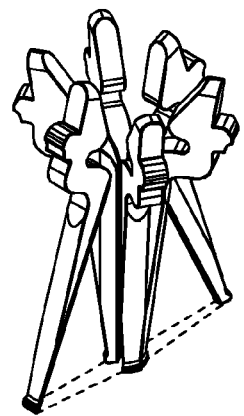
FIG. 18d is an isometric top view illustration of six ribs, in an opened state, according to an embodiment of the present invention.

FIG. 18d is an isometric top view illustration of six ribs 21 in an open state, according to an embodiment of the present invention.

This state was achieved after performance of rotational movement in opposite directions and equal distance of two ribs 21.

Figure 18E:
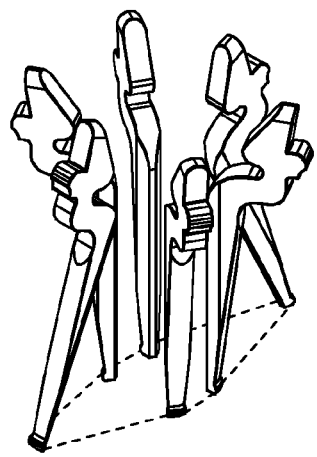
FIG. 18e is an isometric top view illustration of six ribs, in an opened state, according to an embodiment of the present invention.

FIG. 18e is an isometric top view illustration of six ribs 21 in an open state, according to an embodiment of the present invention.

This state was achieved after performance of uniform linear opening of all six ribs 21, followed by rotational movement in opposite directions and equal distance of two ribs 21, both on the same plane of movement.

Figure 18F:
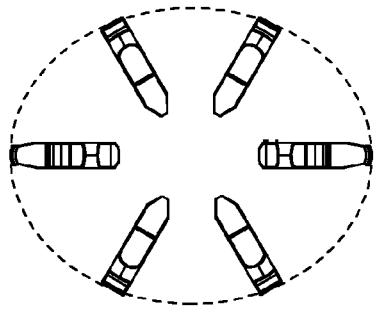
FIG. 18f is a bottom view illustration of six ribs, according to an embodiment of the present invention.

FIG. 18f is a bottom view illustration of six ribs 21 in an open state, according to an embodiment of the present invention.

This state was achieved after performance of uniform linear opening of all six ribs 21, followed by rotational movement in opposite directions and equal distance of two ribs 21, both on the same plane of movement.

The six ribs 21, at each lateral section, are all on an ellipse.

Figure 19A:
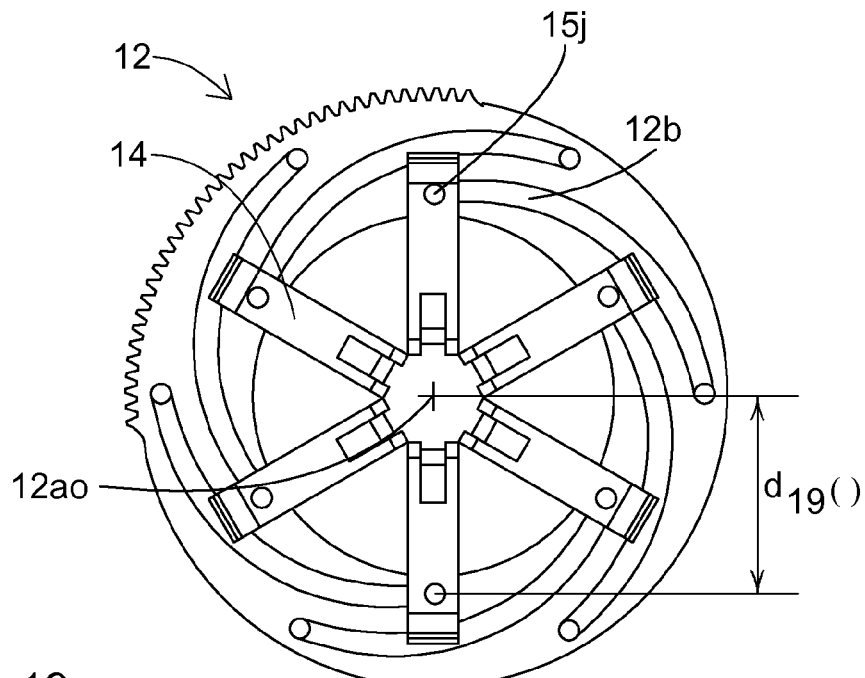
FIG. 19a is a bottom view illustration of a grooved disc, and six main sliders, in closed state, according to an embodiment of the present invention.

FIG. 19a is a bottom view illustration of a grooved disc 12, and six main sliders 15, in closed state, according to an embodiment of the present invention.

In the closed state of the present illustration, all six of the slider pivots 15j are each on a curved groove 12b designated for it, in a location in which the slider pins' distance from the grooved disc central perforation center $d_{19}(\mu)$ is minimal.

Figure 19B:
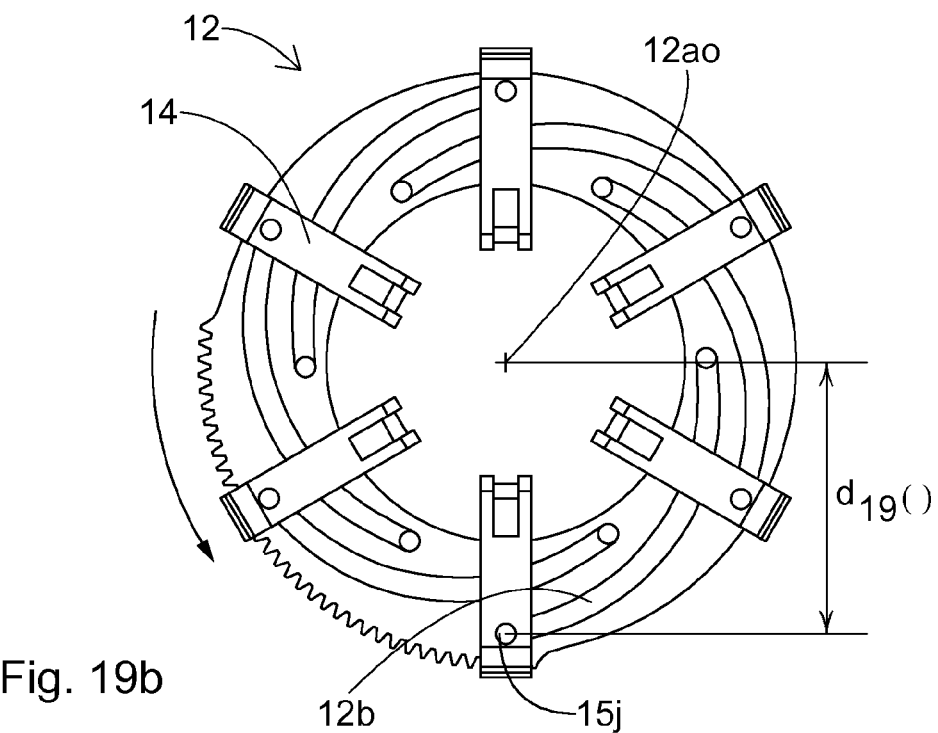
FIG. 19b is a bottom view illustration of a grooved disc, and six main sliders in opened state, according to an embodiment of the present invention.

FIG. 19b is a bottom view illustration of a grooved disc 12, and six main sliders 15, in opened state, according to an embodiment of the present invention.

After the grooved disc 12 performs rotational movement of a grooved disc rotational angle $\mu$, the slider pins' distance from the grooved disc central perforation center $d_{19}(\mu)$ is maximum. Between both of these end states, the slider pins' distance from the grooved disc central perforation center $d_{19}(\mu)$ depends on the grooved disc rotational angle $\mu$.

Figure 20:
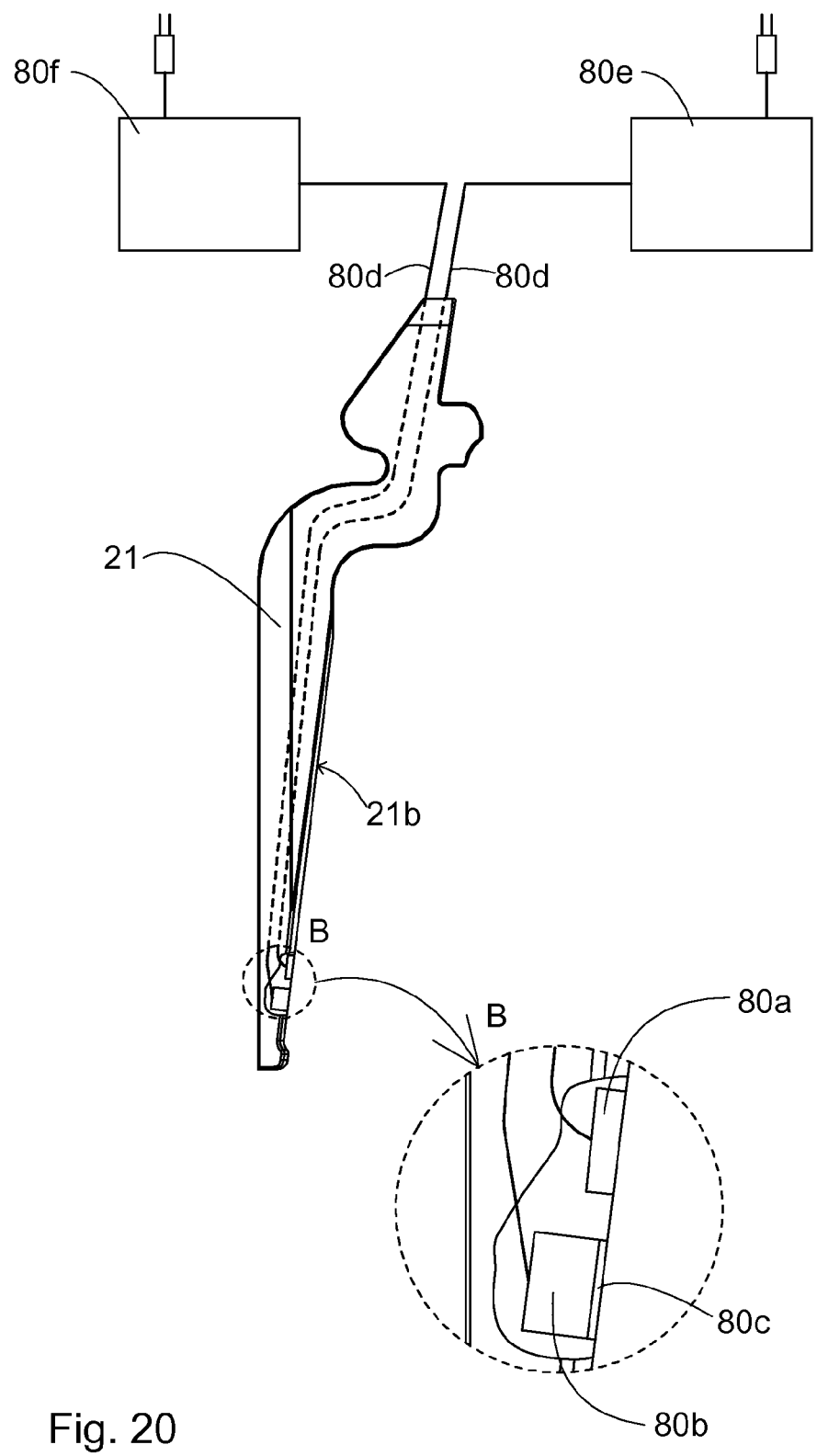
FIG. 20 is a side view illustration of a rib having sensors, and a block diagram of transducers, according to an embodiment of the present invention.

FIG. 20 is a side view illustration of a rib 21 having sensors, and a block diagram of transducers, according to an embodiment of the present invention.

For the purpose of pressure and saturation measurement monitoring during the operation, at least one rib 21 is mounted with a pressure sensor 80a and a tissue oxygen saturation sensor 80b, disposed near the rib back surface 21b, and each connected to an electrical conductor 80d. The pressure sensor 80a transmits signals to an pressure transducer 80e, and the tissue oxygen saturation sensor 80b transmits signals to an oxygen saturation sensor 80f.

The pressure sensor 80a serves the purpose of measuring pressure according to the type of tissue applying the pressure, such as intra-cranial pressure, intra-tissue pressure, or retracted tissue pressure The tissue oxygen saturation sensor 80b can also be composed of an infrared diode emitter that emits infrared radiation and a receiver for receiving the infrared radiation returned from the tissue.

The infrared diode emitter and the receiver are disposed behind a transparent window 80c, which can also be made of ceramic material or glass.

According to anther embodiment of the present invention the pressure sensor 80a and the tissue oxygen saturation sensor 80b are mounted separately, each on a different rib 21.

Figure 21:
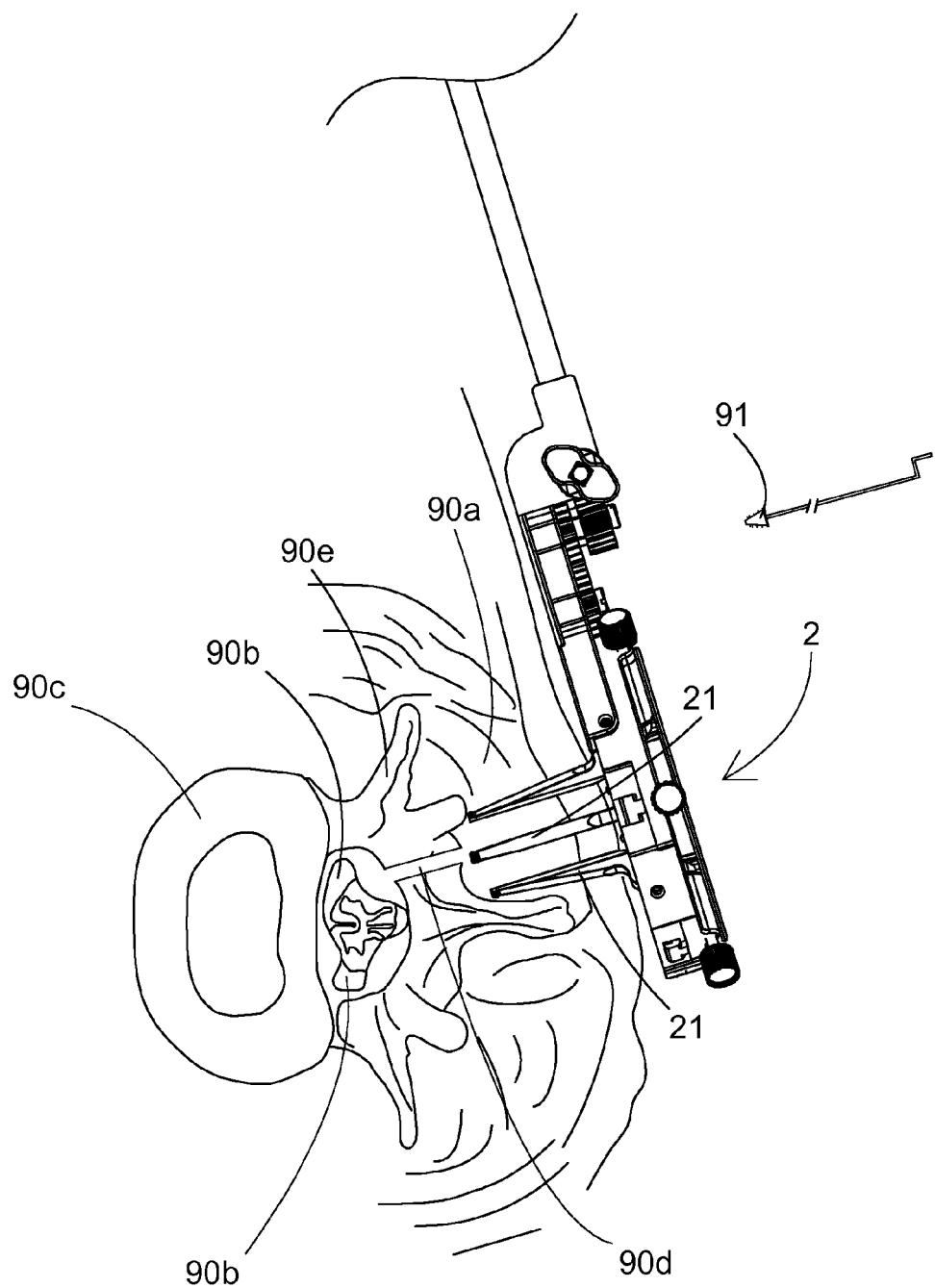
FIG. 21 is a side view illustration of a surgical retractor after penetration and opening for the purpose of performing spinal minimal invasive neurosurgery, according to an embodiment of the present invention.

FIG. 21 is a side view illustration of a surgical retractor 2, after insertion and opening for the purpose of performing spinal minimal invasive neurosurgery, according to an embodiment of the present invention.

The ribs 21 were inserted through the muscle 90a and opened, in the case shown in the present illustration, with the opening movements of all of the ribs 21 being strictly linear.

The insertion was toward the vertebrae 90c, more specifically toward the spinal canal 90b. Subsequently, an incision line of lamina 90d was made. Due to the external shape of the bone 90e, use was made of ribs 21 of varying lengths, with the rib 21 shown as the central one being longer.

A wedge 91, shown here magnified relative to the dimensions of the surgical retractor 2, can serve for opening-distraction and fusion of lamina vertebralis.

Figure 22:
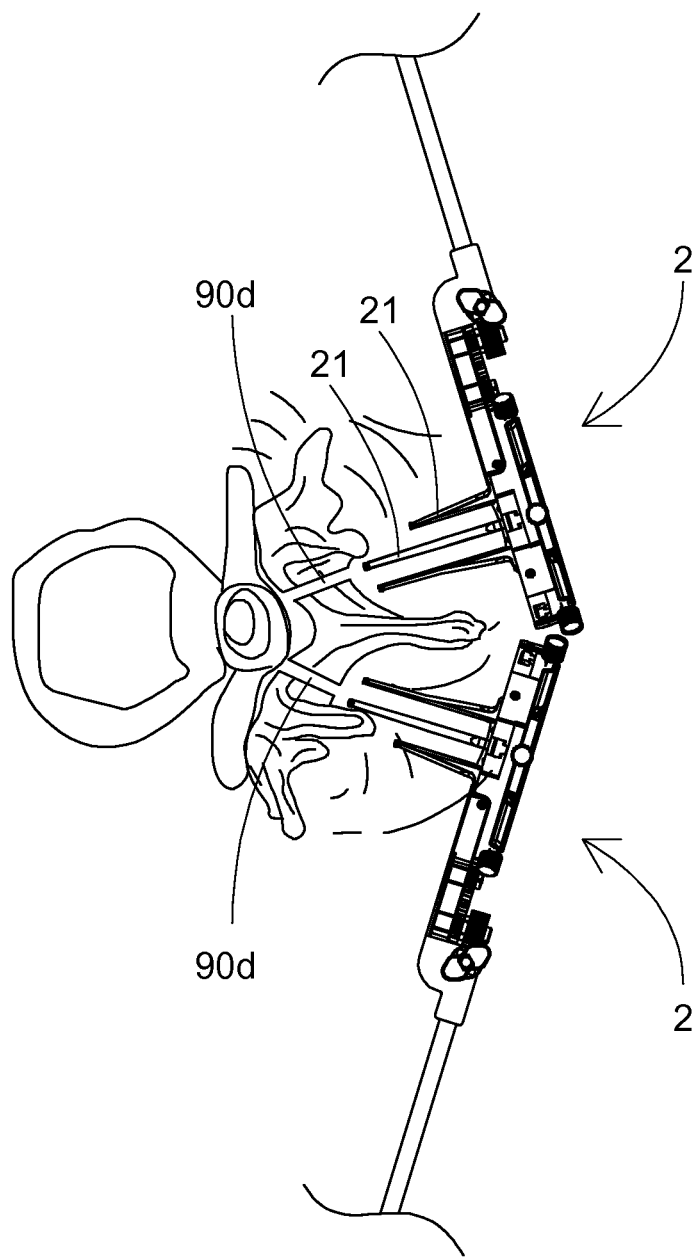
FIG. 22 is a side view illustration of two surgical retractors after penetration and opening for the purpose of performing spinal minimal invasive neurosurgery, according to an embodiment of the present invention.

FIG. 22 is a side view illustration of two surgical retractors 2 after insertion and opening, for the purpose of performing spinal minimal invasive neurosurgery, according to an embodiment of the present invention.

During performance of the operation, use was made of two surgical retractors 2 and two incision lines of lamina 90d are made.

When necessary, one retractor can be used to perform an operation on one side and, after completion on one side, to perform the same operation on the other side. However, it is optimally preferable to perform a simultaneous bilateral laminotomy (SBL) with minimal time delay, to prevent future anatomical asymmetry in lamina and any unnecessary movement of the excised lamina, which can cause iatrogenic damage to neural roots and ligaments Likewise, simultaneous insertion of bilateral wedges for symmetric spinal channel decompression (SSCD) is also preferable.

The present illustration clearly shows the different lengths of ribs 21 relative to each other.

Figure 23:
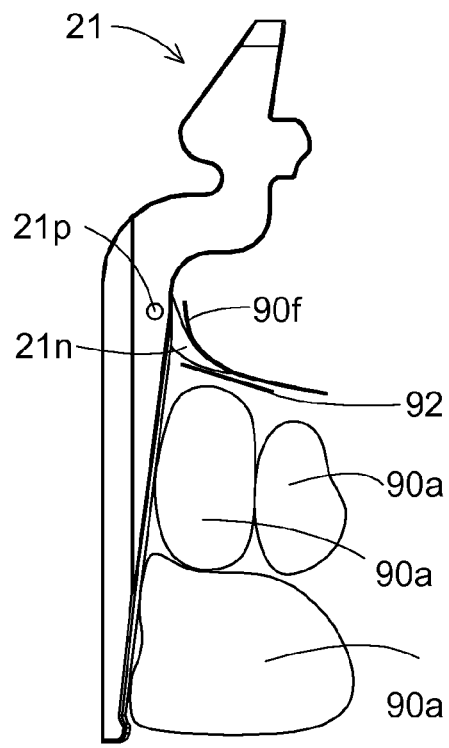
FIG. 23 is a side view illustration of a rib having a rib hook, inside skin and muscle, according to an embodiment of the present invention.

FIG. 23 is a side view illustration of a rib 21, having The present illustration demonstrates the manner in which the rib hook 21*n* supports skin 90*f* and is above fascia 92, while the muscles 90*a* are in contact with rib 21.

Figure 24:
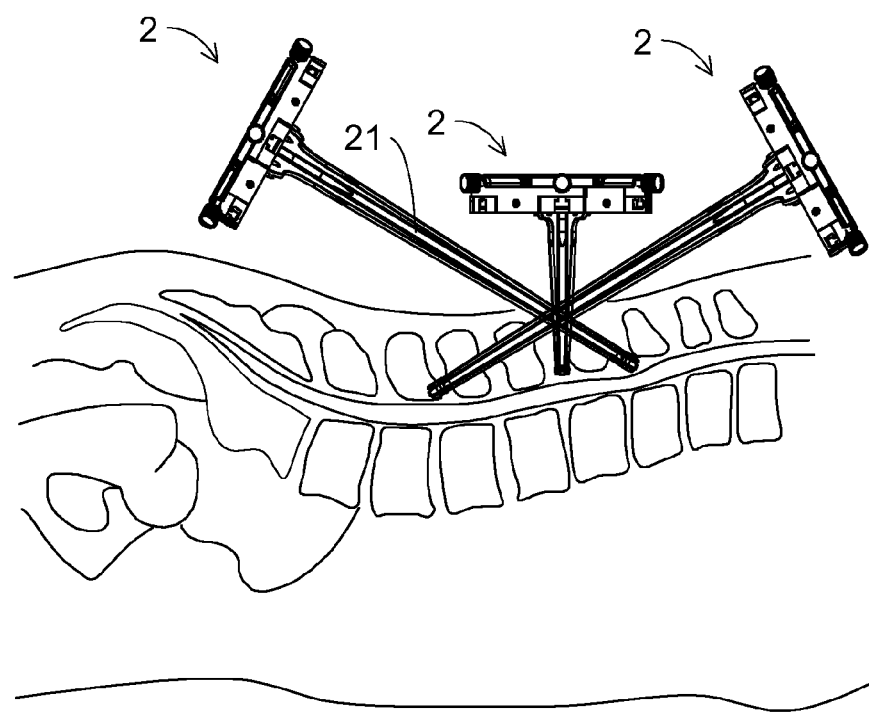
FIG. 24 is a side view illustration of a surgical retractor at three different angles, according to an embodiment of the present invention.

FIG. 24 is a side view illustration of a surgical retractor 2 at three different angles, according to an embodiment of the present invention.

This illustration demonstrates the option of inserting a surgical retractor 2 through one single incision and positioning it at different angles relative to the spine for the purpose of performing several different operations. Between subsequent operations, the ribs 21 can be replaced to be of a suitable length for each different purpose.

Figure 25:
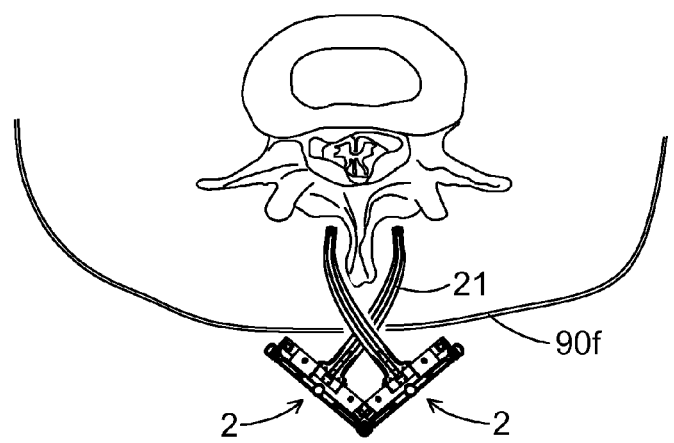
FIG. 25 is a side view illustration of a surgical retractor at two different angles, according to an embodiment of the present invention.

FIG. 25 is a side view illustration of a surgical retractor 2 at two different angles, according to an embodiment of the present invention.

According to an embodiment of the present invention, the ribs 21 are curved. This illustration demonstrates the option for performing bilateral spinal cord decompression via a single incision.

Figure 26:
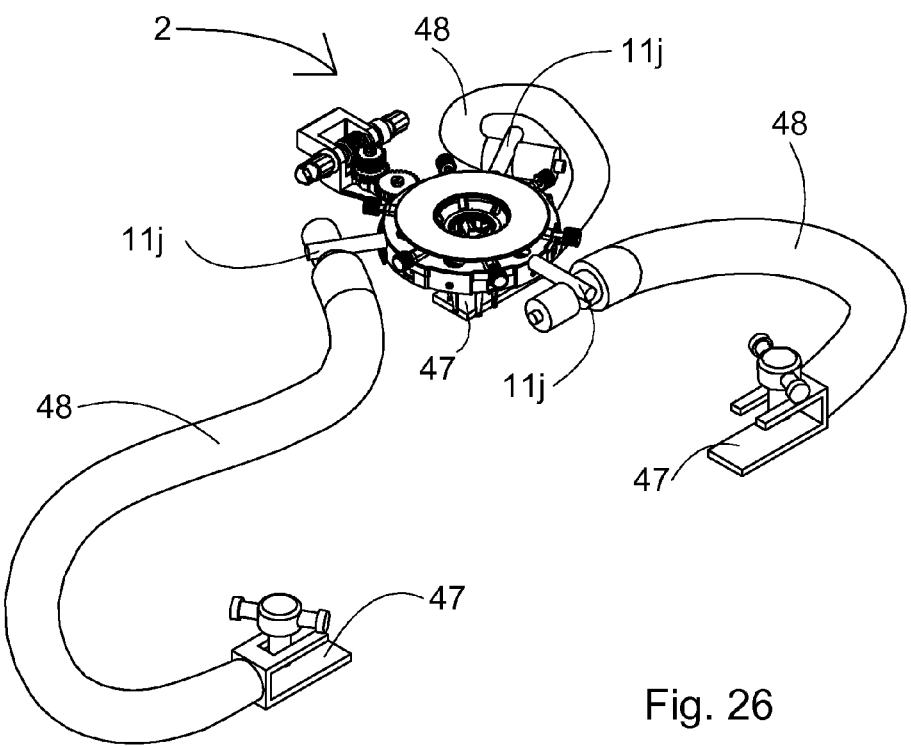
FIG. 26 is an isometric view illustration of a surgical retractor connected to holding arms, according to an embodiment of the present invention.

FIG. 26 is an isometric view illustration of a surgical retractor 2 connected to holding arms 48, according to an embodiment of the present invention.

The present illustration demonstrates connection and carrying of the surgical retractor 2 without use of an adaptor 40, (not shown in the present illustration).

The surgical retractor 2 according to an embodiment of the present invention includes cover disc holding pins 11*j*, for example, three, each of which can be connected to a holding arm 48, with a clamp 47, or any other suitable device, at its end, for the purpose of connection to the operation bed.

The holding arm 48 is an arm which can be bent and geometrically adapted, and is capable of steadily carrying a load. This arm can be continuous or composed of segments.

FIGS. 27*a*-27*f* are side view illustrations of a surgical retractor 2 at six different stages of opening in the operated patient's body, according to an embodiment of the present invention.

All six illustrations show only two ribs 21 for each retractor 2.

Figure 27A:
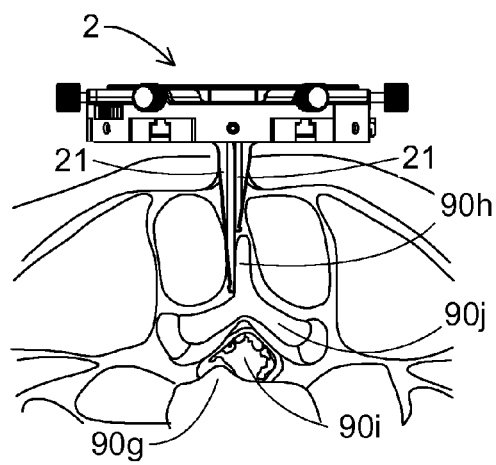
FIGS. 27a-27f are side view illustrations of a surgical retractor at six different stages of opening within the operated patient's body.

FIG. 27*a* shows a stage of insertion of a retractor 2, having ribs 21, with the length of each one being different from the other.

These lengths are selected according to the anatomic structure of the operated patient.

Figure 27B:
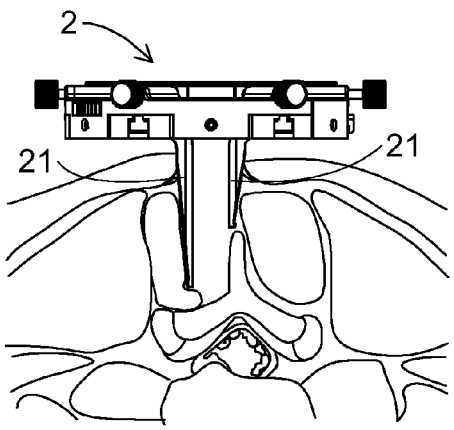

FIG. 27*b* shows a stage of linear opening, toward the left according to the orientation of the present illustration, of the longer rib 21.

Figure 27C:
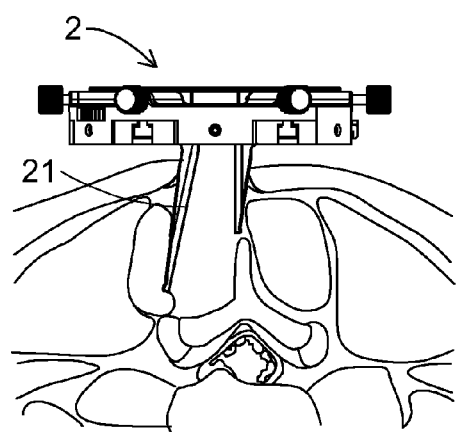

FIG. 27*c* shows a stage of angular opening, clockwise according to the orientation of the present illustration, of the longer rib 21.

Figure 27D:
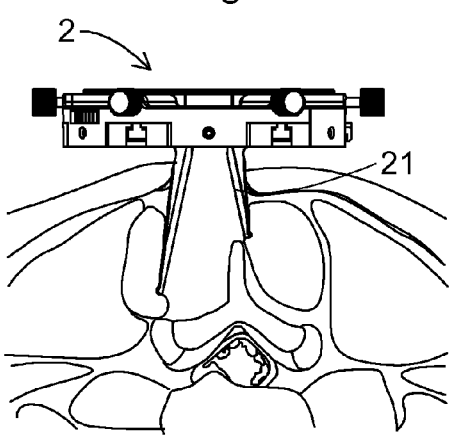

FIG. 27*d* shows a stage of angular opening, counterclockwise according to the orientation of the present illustration, of the shorter rib 21.

Figure 27E:
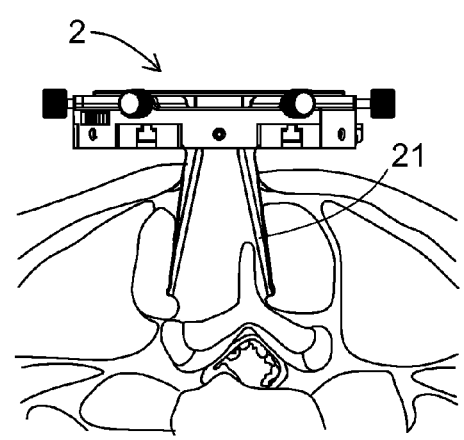

FIG. 27*e* shows a stage after replacement of the shorter rib 21 with a longer rib 21, which requires removal and subsequent reinsertion of the retractor 2.

Figure 27F:
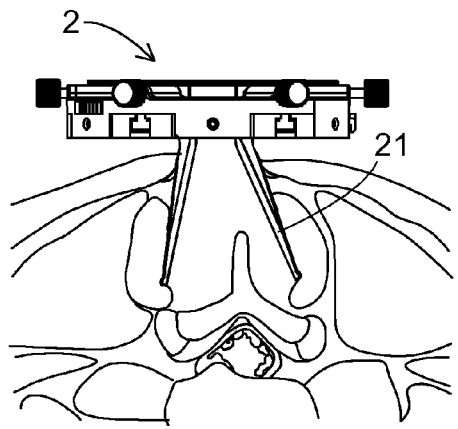

FIG. 27*f* shows an additional stage of angular opening, counterclockwise according to the orientation of the present illustration, of the new rib 21.

It is important to note that these stages, as shown above are not in any way limiting the present invention, and opening can be performed in many various forms and stages.

Figure 28:
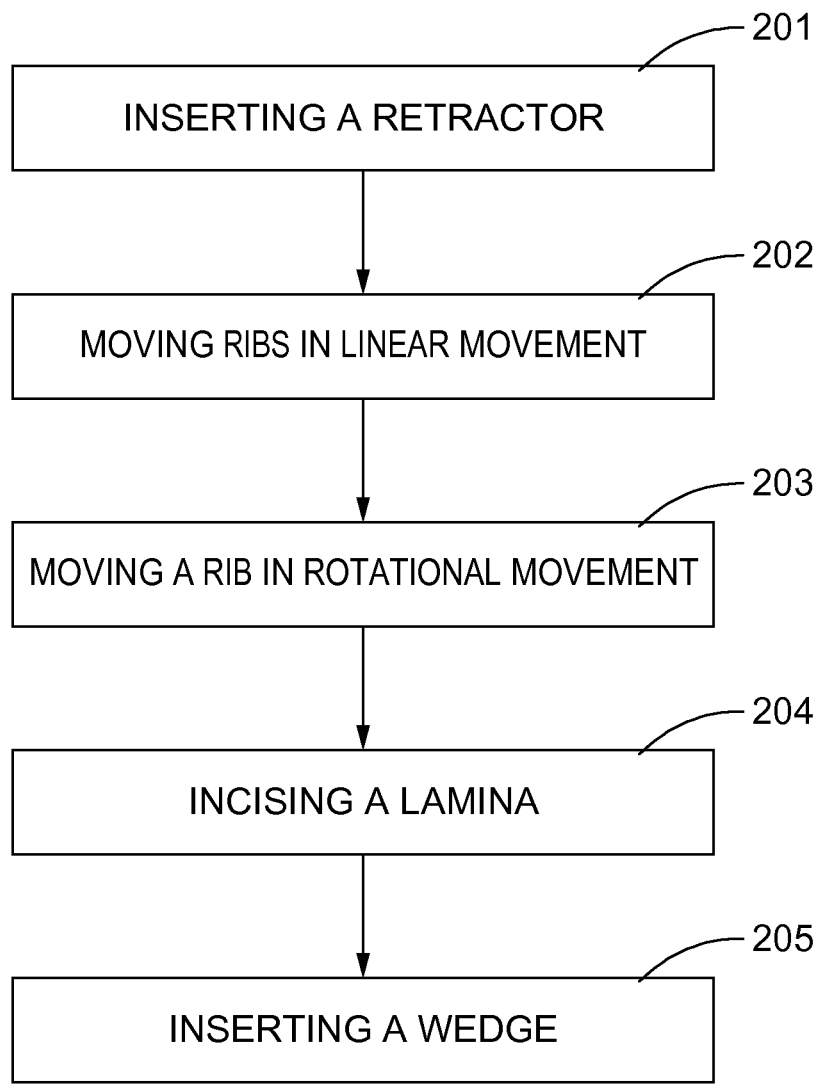
FIG. 28 is a flow chart that schematically illustrates a method of operation for decompression of spinal stenosis, in accordance with an embodiment of the present invention.

FIG. 28 is a flow chart that schematically illustrates a method of operation for minimal invasive (MI), bilateral symmetric decompression (BSD) of spinal stenosis (SS), in accordance with an embodiment of the present invention.

In the first stage of the method of operation for decompression of spinal stenosis, a surgical retractor is inserted through the bilateral projection of lamina vertebralis, wherein the surgical retractor has ribs and a mechanism for transferring of linear and rotational movements of the ribs, (stage 201).

In the second stage of the method of operation for decompression of spinal stenosis, the ribs are moving in linear movements, (stage 202).

In the third stage of the method of operation for decompression of spinal stenosis at least one rib is moving in a rotational movement, (stage 203).

In the fourth stage of the method of operation for decompression of spinal stenosis an incising a lamina proximal to vertebral facets is done with a micro drill or circular micro saw, (stage 204).

In the fifth stage of the method of operation for decompression of spinal stenosis a wedge is inserting for a distraction of bilateral vertebral lamina, (stage 205).

Figure 29A:
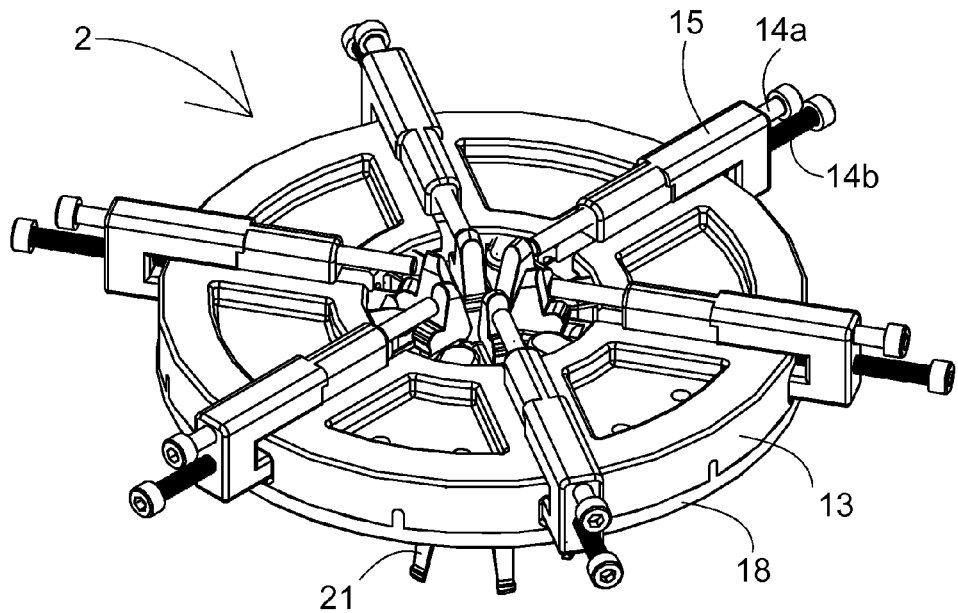
FIG. 29a is an isometric top view schematic illustration of a surgical retractor according to an embodiment of the present invention.

FIG. 29*a* is an isometric top view schematic illustration of a surgical retractor 2 according to an embodiment of the present invention.

This embodiment is simpler than the embodiment of FIG. 2*a*. It includes less part, can be more lightweight, and can likewise be less expensive. As such, it can be suitable for single-time use, as a whole or the majority of its parts.

This embodiment includes the same ribs 21, for all features, as described so far according to the present invention. The ribs 21 of all the embodiments can be made of material or materials transparent to x-rays.

The channeled disc 13 and the main slider 15 of the surgical retractor 2 according to FIG. 29*a* embodiment differ in shape from the channeled disc 13 and the main slider 15 of the surgical retractor 2 according to FIG. 2*a* embodiment. However, in both of these embodiments, the main sliders 15 are assembled into channeled discs 13 so as to enable linear radial movement relative to the centers channeled discs 13.

Figure 29B:
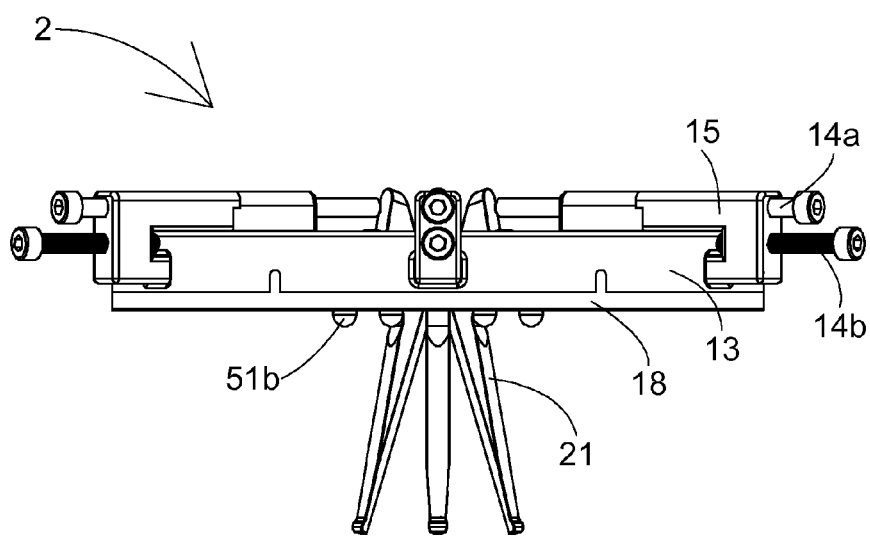
FIG. 29b is a side view schematic illustration of the surgical retractor of FIG. 29a according to an embodiment of the present invention.

FIG. 29*b* is a side view schematic illustration of the surgical retractor 2 of FIG. 29*a* according to an embodiment of the present invention.

The present illustration shows ribs 21 that are all identical in shapes and dimensions, in a state following angular opening. Channeled disc 13 is attached to a base disc 18, under which the illustration shows lamps 51*b*.

Figure 30:
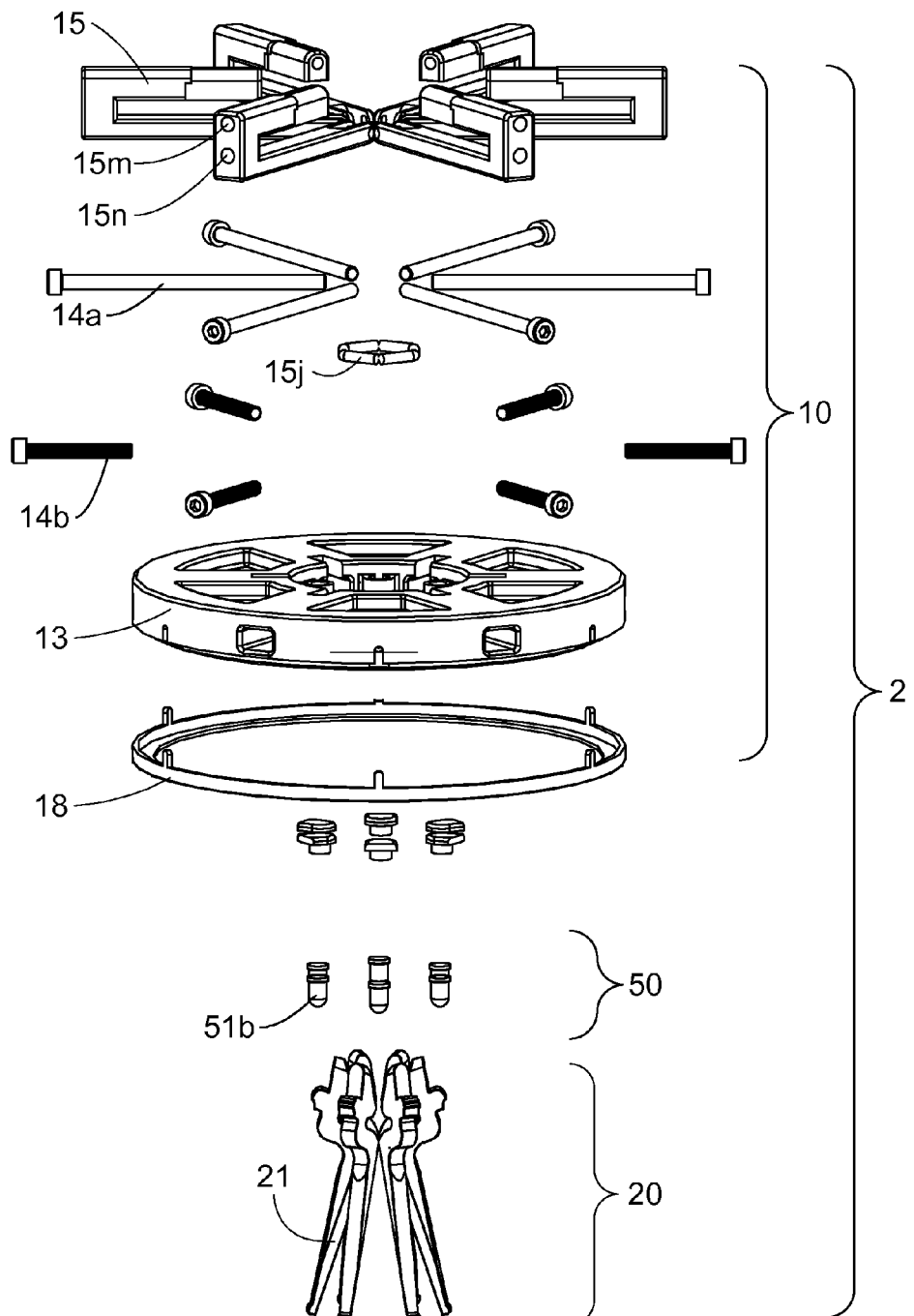
FIG. 30 is an exploded, isometric top view schematic illustration of the surgical retractor of FIG. 29a, according to an embodiment of the present invention.

FIG. 30 is an exploded, isometric top view schematic illustration of the surgical retractor 2 of FIG. 29*a*, according to an embodiment of the present invention.

The surgical retractor 2 of FIG. 29*a* includes several assemblies, the mechanism for transferring of linear and rotational movements 10, the ribs assembly 20, and the lighting assembly 50.

The mechanism for transferring of linear and rotational movements 10 includes the main sliders 15, slider pivots 15*j*, angular adjustment bolts 14*a*, linear adjustment bolts 14*b*, channeled disc 13, and a base disc 18.

The channeled disc 13 can be made of various materials, also including various metals or materials transparent to x-rays, such as a plastic material, and it can be designated for single-time use.

The base disc 18 is connected to the bottom of the channeled disc 13 and serves as a cover for electric wires (not shown in the present illustration), which provide electrical power supply to lighting assembly 50, and can also be made of various materials, also including various metals or materials transparent to x-rays.

Each rib 21 engages with a main slider 15 by means of a replaceable slider pivot 15*j* and can be made of various materials, also including various metals or materials transparent to x-rays.

Main slider 15 includes a first interior thread 15*m* into which is screwed an angular adjustment bolt 14*a*, and a second interior thread 15*n* into which is screwed a linear adjustment bolt 14*b*, by means of which the linear and angular opening of the ribs 21 can be adjusted.

Figure 31A:
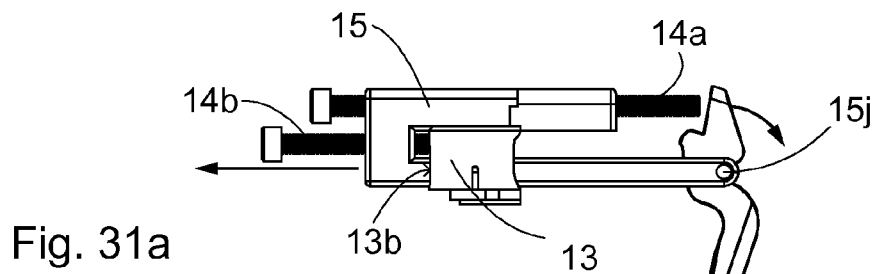
FIG. 31a is a side view schematic illustrations of a segment of a channeled disc, an angular adjustment bolt, a linear adjustment bolt, a main slider, a slider pivot, and a rib of the surgical retractor of FIG. 29a, according to an embodiment of the present invention.

FIG. 31*a* is a side view schematic illustration of a segment of a channeled disc 13, an angular adjustment bolt 14*a*, a linear adjustment bolt 14*b*, a main slider 15, a slider pivot 15*j*, and a rib 21 of the surgical retractor 2 of FIG. 29 according to an embodiment of the present invention.

The screwing of the angular adjustment bolt 14*a* into the first interior thread 15*m* of the main slider 15 applies moment on the rib 21, resulting in its rotational movement around the slider pivot 15*j* relative to the main slider 15. Screwing the linear adjustment bolt 14*b* into the second interior thread 15*n* of the main slider 15 applies force to the channeled disc 13 resulting in linear movement of the main slider 15 along with the rib 21 relative to the channeled disc 13.

The shapes and sizes of the slider pivot hole 15*e*, the gap between the slider pivot and the slider among arms surface $d_6$, the slider among arms surface 15*f*, and the slider among arms surface radius $r_3$ as shown in FIG. 10*d* also apply to the main slider 15 shown in the present illustration.

Figure 31B:
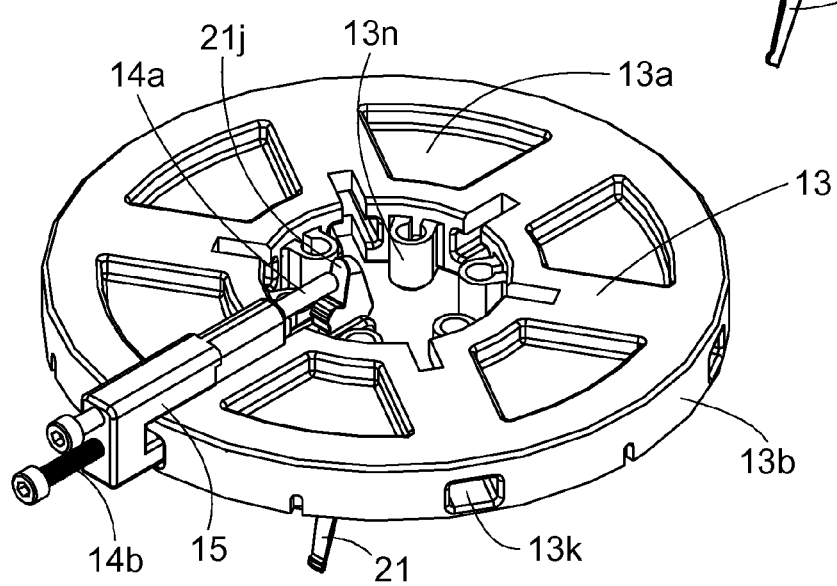
FIG. 31b is an isometric top view schematic illustration of a channeled disc, an angular adjustment bolt, a linear adjustment bolt, a main slider, and a rib of the surgical retractor of FIG. 29a, according to an embodiment of the present invention.

FIG. 31*b* is an isometric top view schematic illustrations of a channeled disc 13, an angular adjustment bolt 14*a*, a linear adjustment bolt 14*b*, a main slider 15, and a rib 21 of the surgical retractor 2 of FIG. 29*a*, according to an embodiment of the present invention.

The present illustration shows that channel 13*k* can have a lateral section shape that is closed in all directions.

Figure 32A:
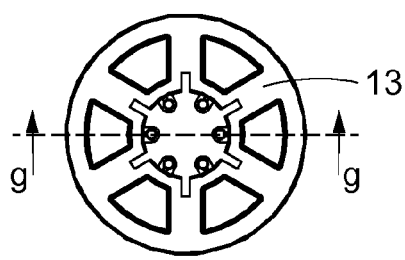
FIG. 32a is a top view schematic illustration of the channeled disc of the surgical retractor of FIG. 29a, according to an embodiment of the present invention, upon which a section plane g-g is marked.

FIG. 32*a* is a top view schematic illustration of the channeled disc 13 of the surgical retractor 2 of FIG. 29*a*, according to an embodiment of the present invention, upon which a section plane g-g is marked.

Figure 32B:
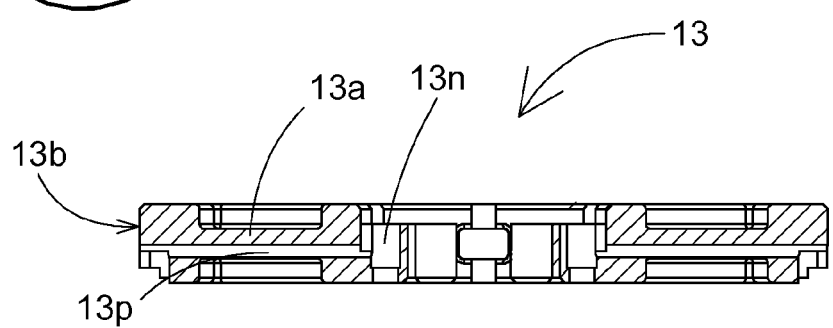
FIG. 32b is a cross sectional view g-g illustrations of the channeled disc of the surgical retractor of FIG. 29a, according to an embodiment of the present invention.

FIG. 32*b* is a cross sectional view g-g illustrations of the channeled disc 13 of the surgical retractor 2 of FIG. 29*a*, according to an embodiment of the present invention.

The present illustration shows channeled disc wire holes 13*p*, which can be threaded with electric wire to provide electric power to the lighting system.

Figure 33:
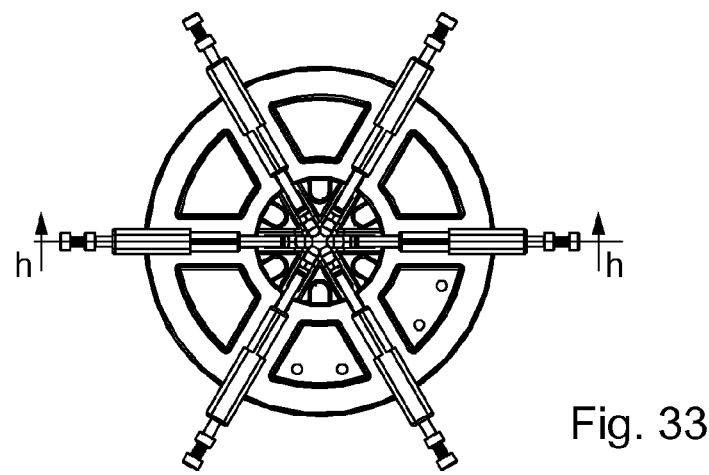
FIG. 33 is a top view schematic illustration of the surgical retractor of FIG. 29a, according to an embodiment of the present invention, upon which a section plane h-h is marked.

FIG. 33 is a top view schematic illustration of the surgical retractor 2 of FIG. 29, according to an embodiment of the present invention, upon which a section plane h-h is marked.

Figure 34:
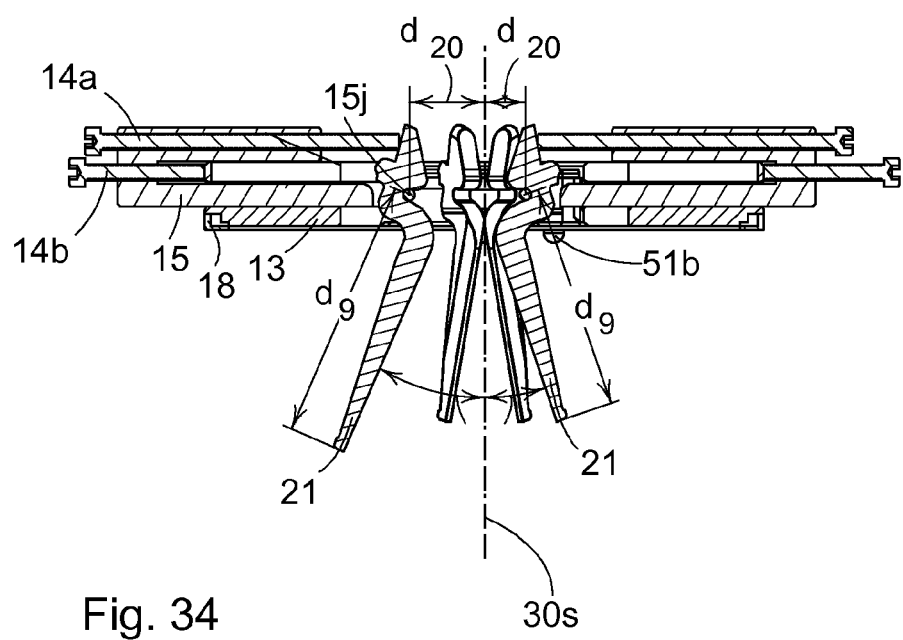
FIG. 34 is a cross sectional view h-h illustrations of the surgical retractor of FIG. 29a, according to an embodiment of the present invention.

FIG. 34 is a cross sectional view h-h illustration of the surgical retractor 2 of FIG. 29*a*, according to an embodiment of the present invention.

The section plane shows two ribs 21, the left one of which having a larger rib working arm length $d_9$. The dimensions of its rib opening angle δ and slider pivot distance from the grooved disc central perforation center $d_{20}$ are also larger.

The dimensions of the rib opening angle δ and the slider pivot distance from the grooved disc central perforation center $d_{20}$ are respectively determined by the extent to which the angular adjustment bolt 14*a* and the linear adjustment bolt 14*b* are screwed in relative to main slider 15.

The combination of dimensions given here is one private case of many possible cases and combinations, as well as occasional replacement of ribs 21.

Figure 35A:
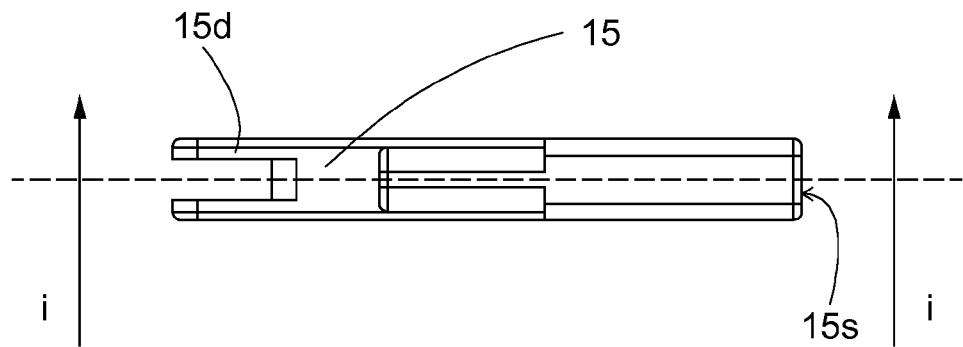
FIG. 35a is a top view schematic illustration of a main slider of the surgical retractor of FIG. 29a, according to an embodiment of the present invention, upon which a section plane i-i is marked.
Figure 35B:
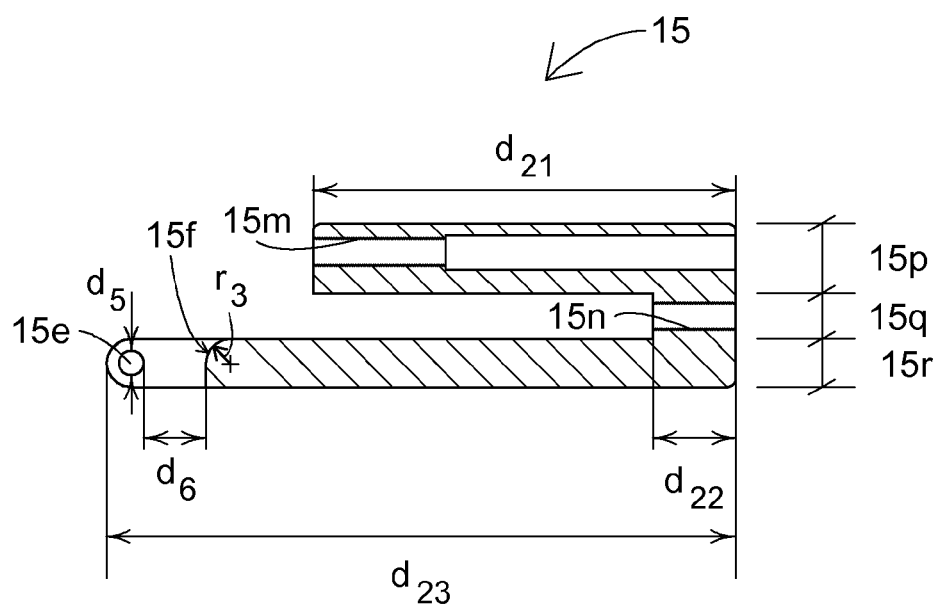
FIG. 35b is a cross sectional view i-i illustrations of a main slider of the surgical retractor of FIG. 29a, according to an embodiment of the present invention.

FIG. 35*b* is a cross sectional view i-i illustrations of a main slider 15 of the surgical retractor 2 of FIG. 29*a*, according to an embodiment of the present invention.

The main slider 15 of the surgical retractor 2 of FIG. 29*a* has three portions, a main slider upper portion 15*p*, a main slider mid portion 15*q*, and a main slider lower portion 15*r*.

In the upper portion 15*p*, there is a perforation, all or part of which comprises first interior thread 15*m*. In the mid portion 15*q*, there is a perforation, all or part of which comprises second interior thread 15*n*.

The three portions have an upper portion length $d_{21}$, a mid portion length $d_{22}$, and a lower portion length $d_{23}$, respectively. The dimension of the upper portion length $d_{21}$ r than that of is smaller lower portion length $d_{23}$, and the dimension of the mid portion length $d_{22}$ is smaller than those of both. This serves the purpose of conforming the shapes and dimensions of the main slider 15 to those of other components with which it is engaged, for smooth and efficient use.

Figure 36A:
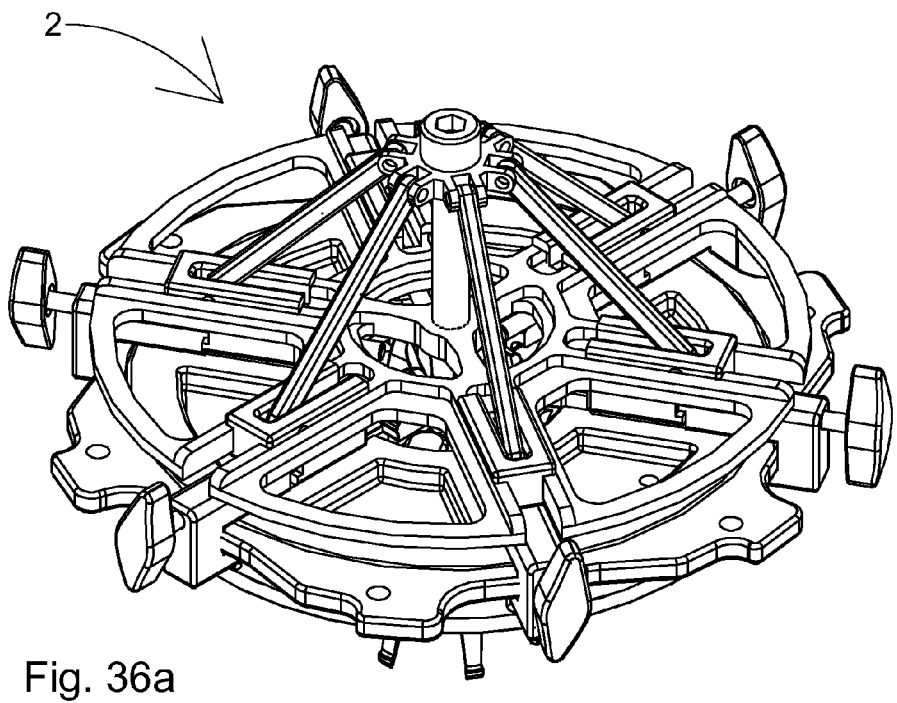
FIG. 36a is an isometric top view schematic illustration of a surgical retractor according to an embodiment of the present invention.

FIG. 36*a* is an isometric top view schematic illustration of a surgical retractor 2 according to an embodiment of the present invention.

Figure 36B:
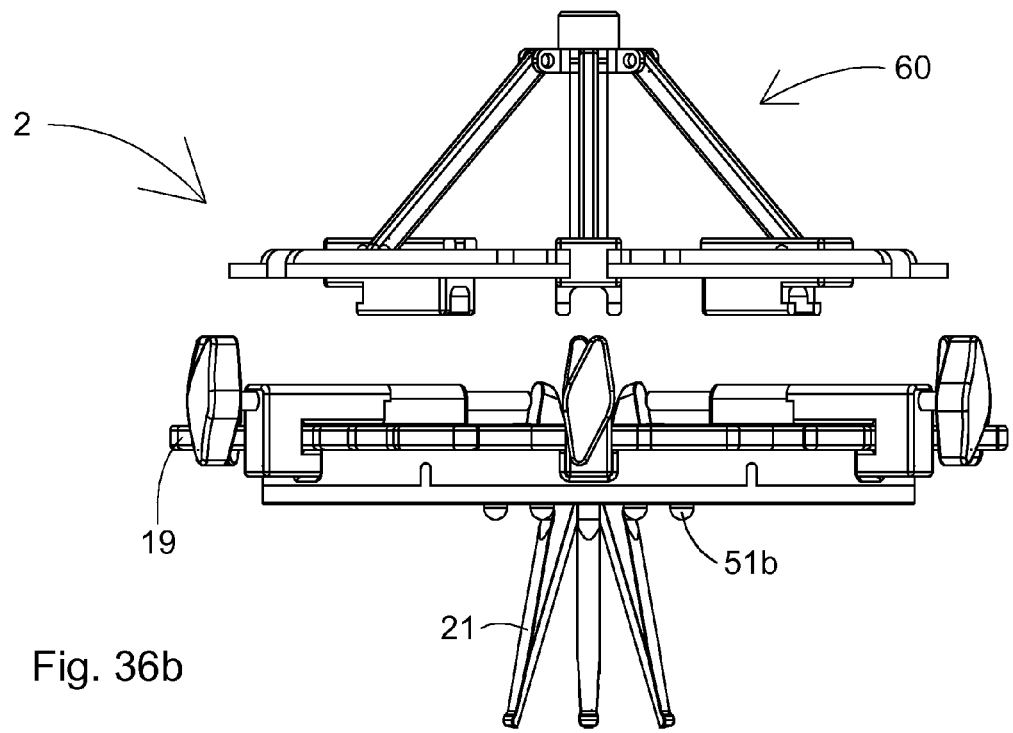
FIG. 36b is a side view schematic illustration of the surgical retractor of FIG. 36a, according to an embodiment of the present invention.

FIG. 36*b* is a side view schematic illustration of the surgical retractor 2 of FIG. 36*a*, according to an embodiment of the present invention.

This embodiment is very similar to the embodiment of FIG. 29*a*, however also includes an opening mechanism first type 60*a*, which facilitates linear opening of the ribs 21, and an external disc 19 to prevent undesired linear closing.

The present illustration shows the opening mechanism first type 60*a* slightly separated upwards from the other assemblies of the surgical retractor 2. The present illustration also shows lamps 51*b*.

Figure 37:
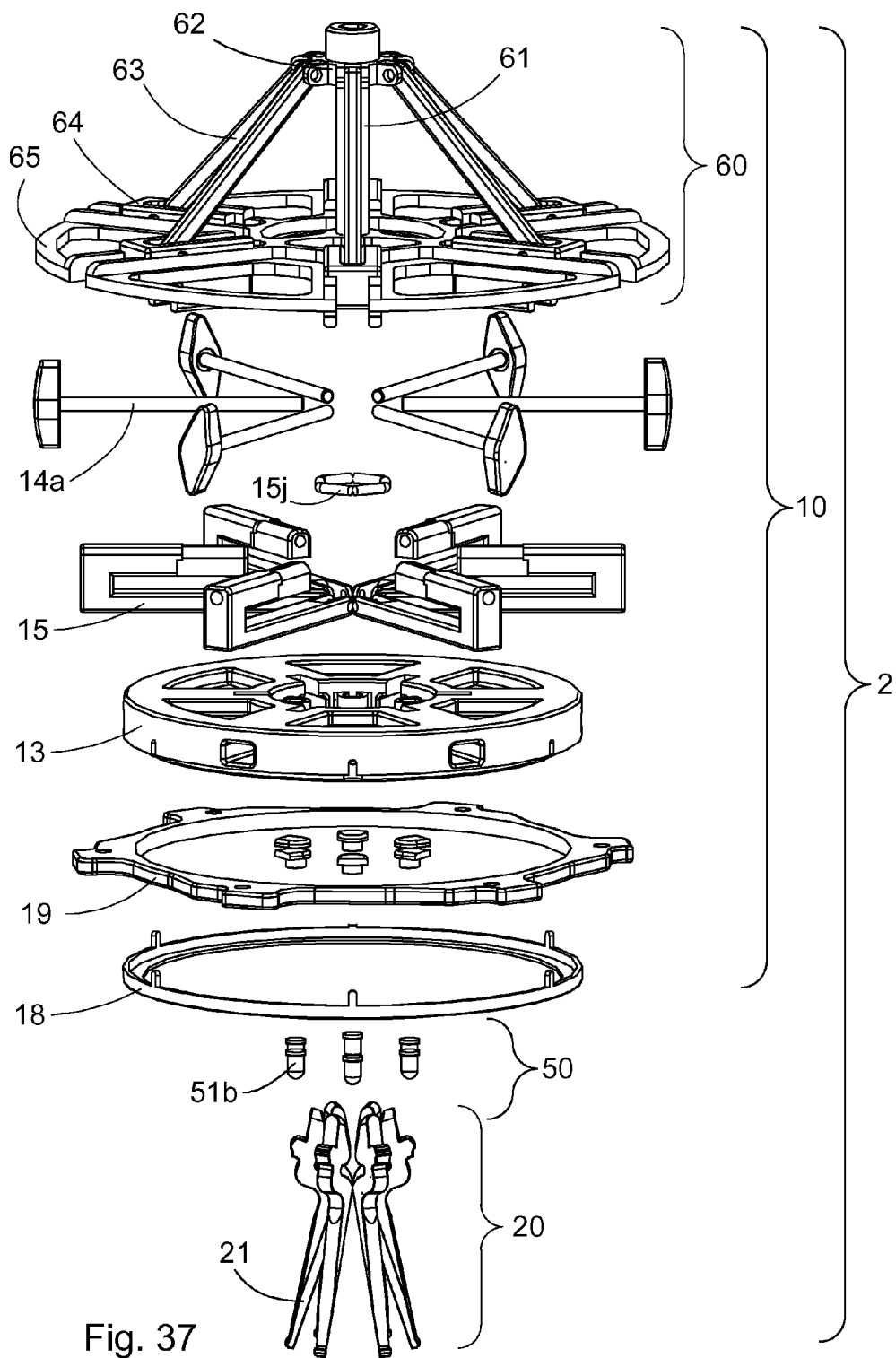
FIG. 37 is an exploded, isometric top view schematic illustration of the surgical retractor of FIG. 36a, according to an embodiment of the present invention.

FIG. 37 is an exploded, isometric top view schematic illustration of the surgical retractor 2 of FIG. 36*a*, according to an embodiment of the present invention.

The surgical retractor 2 of FIG. 36*a* includes several assemblies, the mechanism for transferring of linear and rotational movements 10, the ribs assembly 20, the lighting assembly 50, and the opening mechanism first type 60*a*.

The mechanism for transferring of linear and rotational movements 10 includes the main sliders 15, slider pivots 15*j*, angular adjustment bolts 14*a*, the channeled disc 13, and a base disc 18.

The channeled disc 13 can be made of various materials, also including metals or materials transparent to x-rays, such as plastic material, and can be designated for single-time use.

The base disc 18 is attached to the bottom of the cover disc 11 and serves as a cover for electrical wires (not shown in the present illustration), which provide electrical supply to lighting assembly 50, which can also be composed of various materials, also including metals or materials transparent to x-rays.

Each rib 21 engages with a main slider 15 by means of a replaceable slider pivot 15*j*, which can be made of various materials, also including metals or materials transparent to x-rays.

Main slider 15 includes a first interior thread 15*m*, into which is screwed an angular adjustment bolt 14*a*, and by means of which the angular opening of rib 21 can be determined. The linear opening of ribs 21 can be done by means of activating pushing forces, directly by an operator's hand, in an opening direction, upon the main sliders 15. After obtaining sufficient opening, the base disc 18 is rotated into a state that prevents unwanted closing back.

An additional option for performing opening is by means the opening mechanism first type 60a. Downward force (in the orientation of the present illustration) on the opening mechanism ring 64 causes opening mechanism arms 63 to activate linear opening force upon the opening mechanism sliders 64, and when these are engaged with the main sliders 15, the main sliders 15 are subject to linear opening forces. After performance of the linear opening, the base disc 18 is rotated to a state that prevents closing back and the opening mechanism first type 60a is removed from the area in which the medical procedure is performed.

Following is a list of possible materials that can be used for various components of the surgical retractor 2 according to the embodiments of the present invention. This list is in no way limiting the present invention to the use of any specific materials.

The channeled disc 13 and the external disc 19 can be made of nylon 6/10 or polycarbonate.

The ribs 21 can be made of nylon 6/10+20%-30% carbon fiber or stainless steel such as stainless steel 316L.

The main slider 15 can be made from stainless steel such as stainless steel 316L or from brass.

The opening mechanism first type 60a can be made from stainless steel such as stainless steel 316L.

Figure 38:
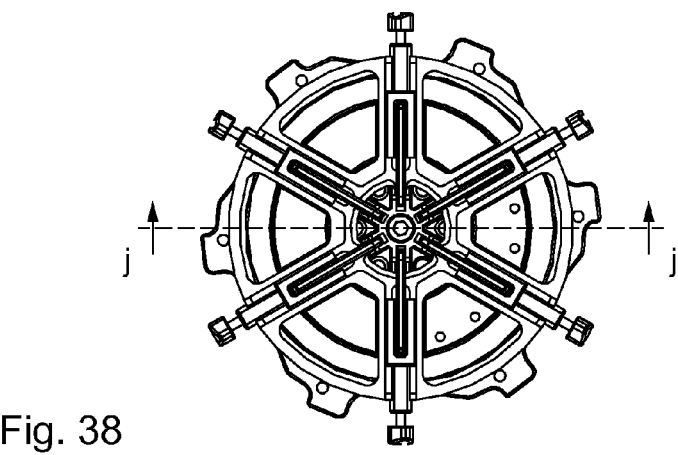
FIG. 38 is a top view schematic illustration of the surgical retractor of FIG. 36a, according to an embodiment of the present invention, upon which a section plane j-j is marked.

FIG. 38 is a top view schematic illustration of the surgical retractor 2 of FIG. 36a, according to an embodiment of the present invention, upon which a section plane j-j is marked.

Figure 39:
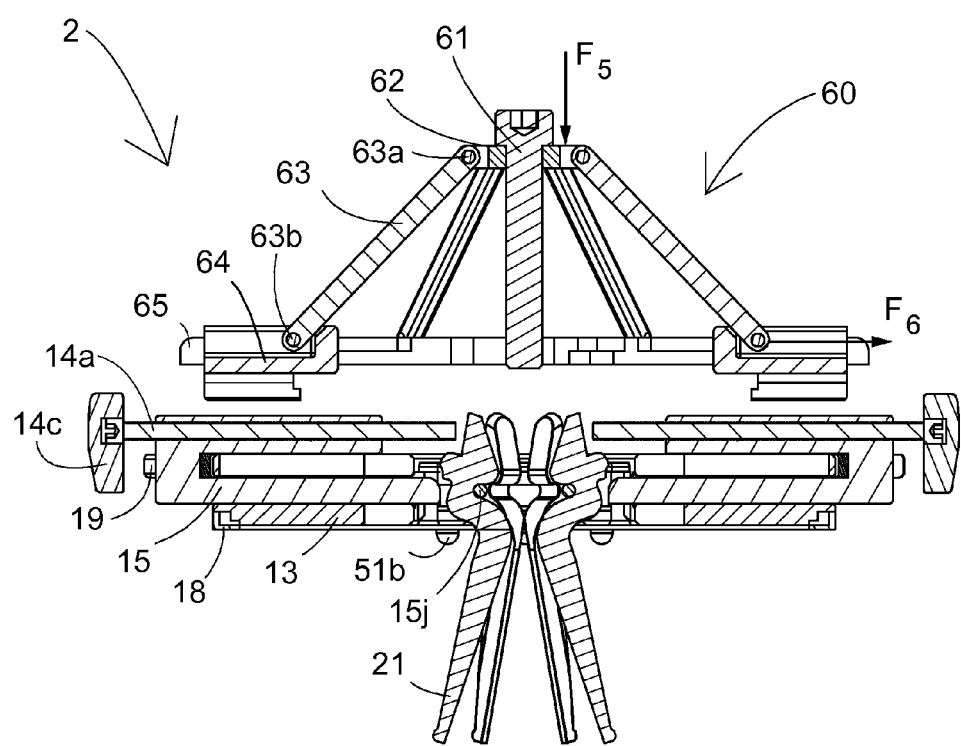
FIG. 39 is a cross sectional view j-j illustration of the surgical retractor of FIG. 36a, according to an embodiment of the present invention.

FIG. 39 is a cross sectional view j-j illustration of the surgical retractor 2 of FIG. 36a, according to an embodiment of the present invention.

Outward linear movement, in the present illustration leftwards, of the main slider 15, which is shown on the left in the present illustration, will result in linear opening motion of the left rib 21, as a result of force applied by the slider pivot 15j, which is connected to the main slider 15.

Rotation of the linear adjustment bolt head 14c assembled to the angular adjustment bolt 14a in a direction that will screw it inward, will result in applying torque to the upper part of rib 21, resulting in rotational opening.

The present illustration shows that the opening mechanism first type 60a includes an opening mechanism pole 61a, upon which is mounted an opening mechanism arms ring 62, which can move along its length.

The opening mechanism arms ring 62 is connected to opening mechanism arms 63 by means of opening mechanism arm upper pivots 63a. The other end of each opening mechanism arm upper pivot 63a is connected by means of an opening mechanism arm lower pivot 64b to an opening mechanism slider 64 which conforms to the opening mechanism base 65, so as to enable its linear radial movement.

When an axial force $F_5$ is applied to the opening mechanism arms ring 62, downward movement, in the view shown in the present illustration, of the opening mechanism arms ring 62 is achieved, which is transmitted into radial force $F_6$ activated upon opening mechanism slider 64. This force can serve to move the main slider 15 in linear outward movement.

Figure 40:
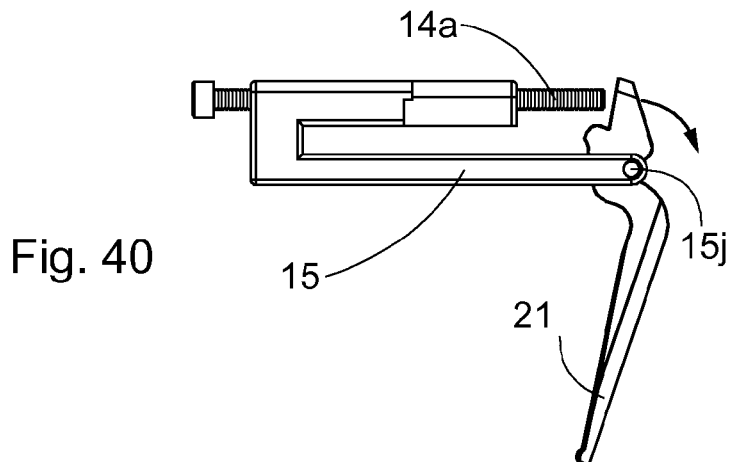
FIG. 40 is a side view schematic illustration of an angular adjustment bolt, a main slider, a slider pivot, and a rib of the surgical retractor of FIG. 36a, according to an embodiment of the present invention.

FIG. 40 is a side view schematic illustration of an angular adjustment bolt 14a, a main slider 15, a slider pivot 15j, and a rib 21, of the surgical retractor 2 of FIG. 36a, according to an embodiment of the present invention.

Screwing the angular adjustment bolt 14a into the first interior thread 15m of the main slider 15 causes the activation of moment upon the rib 21, resulting in rotational movement of rib 21 around the slider pivot 15j relative to the main slider 15.

The shapes and dimensions of the slider pivot hole 15e, the gap between the slider pivot and the slider among arms surface $d_6$, the slider among arms surface 15f, and the slider among arms surface radius $r_3$, as described in FIG. 10d also apply to the main slider 15 shown in the present illustration.

Figure 41:
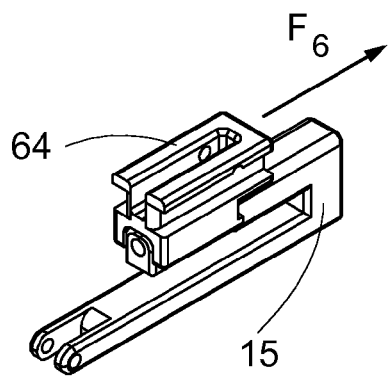
FIG. 41 is an isometric top view schematic illustration of a main slider, and an opening mechanism slider of the surgical retractor of FIG. 36a, according to an embodiment of the present invention.

FIG. 41 is an isometric top view schematic illustration of a main slider 15, and an opening mechanism slider 64 of the surgical retractor 2 of FIG. 36a, according to an embodiment of the present invention.

The opening mechanism slider 64, during the execution of linear opening, activates radial force $F_6$, upon the main slider 15, in the direction of the arrow shown in the present illustration.

Figure 42:
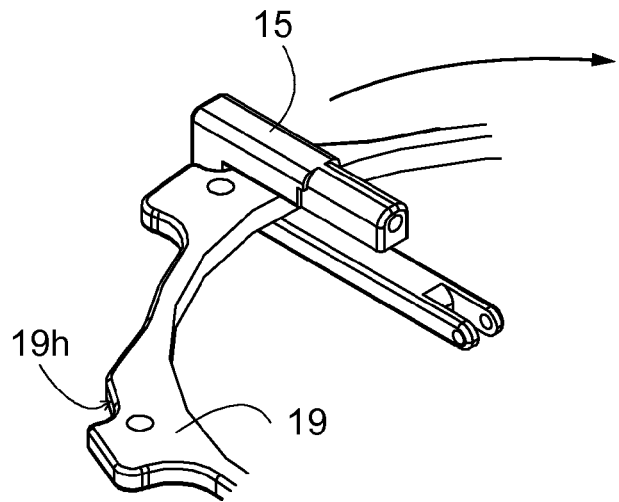
FIG. 42 is an isometric top view schematic illustration of a main slider, and a segment of an external disc of the surgical retractor of FIG. 36a, according to an embodiment of the present invention.

FIG. 42 is an isometric top view schematic illustration of a main slider 15, and a segment of the external disc 19 of the surgical retractor 2 of FIG. 36a, according to an embodiment of the present invention.

External disc 19 includes, for every main slider 15, an external disc stair 19h which after linear opening and after the rotation of the external disc 19 to the desired state prevents the main slider 15 from moving back in the direction of linear closing. The external disc 19, shown in the present illustration, includes for each main slider 15, one external disc stair 19h designated for it, however there is no prevention, according to the present invention, from including more than one external disc stair 19h for each main slider 15 in the external disc 19, so as to be suitable for various degrees of linear opening.

Upon completion of the surgical procedure, the external disc 19 can be rotated back so that the external disc stairs 19h do not prevent linear movement in a closing direction of the sliders 15. In this state, as a result of the pressure of the body tissue in the area of the procedure, and the pressure of the flexible sleeve 23, if it is assembled, the ribs 21 (not shown in the present illustration) close, namely they draw closer to each other, thus facilitating their removal from the patient's body.

Figure 43:
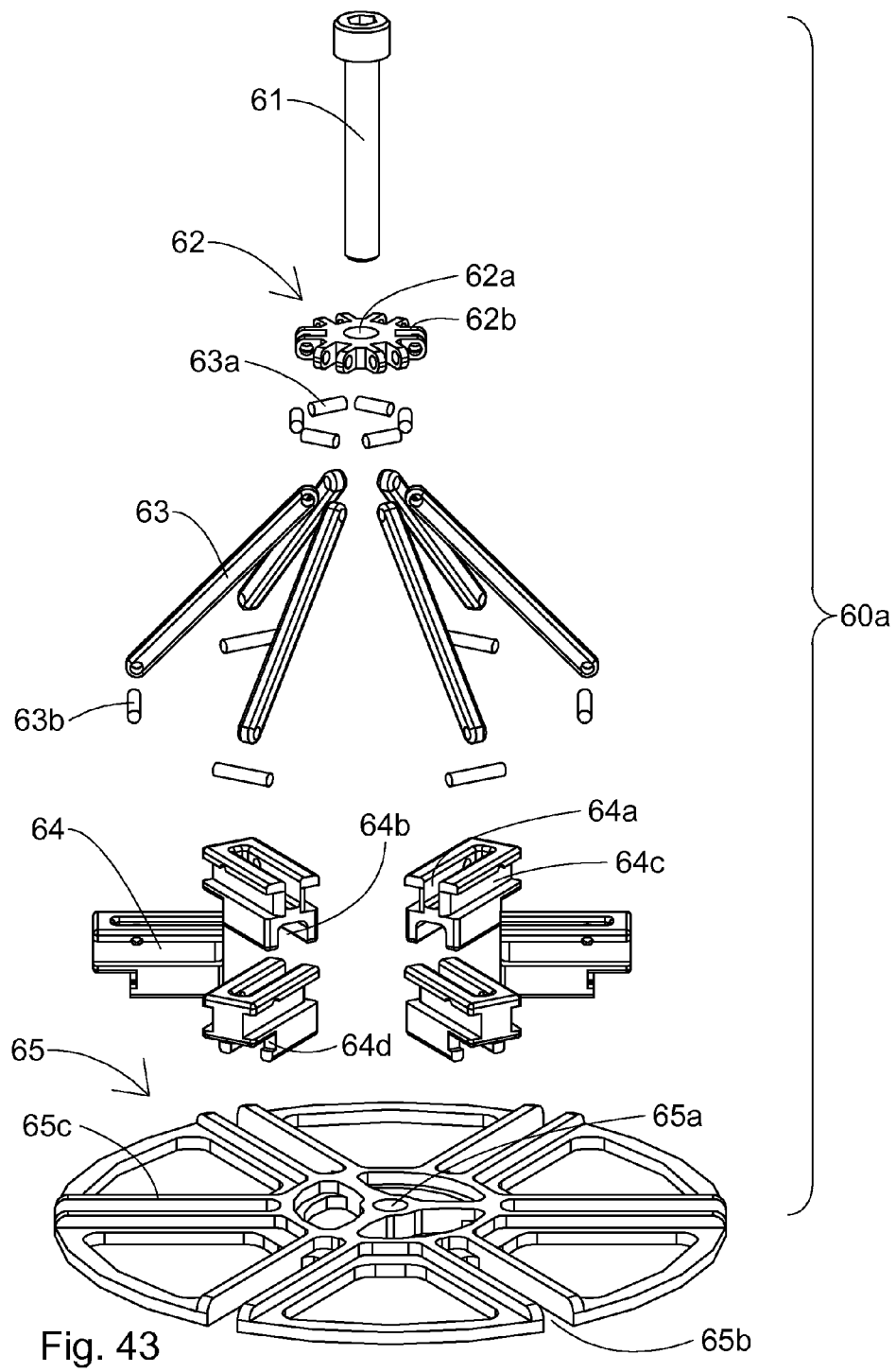
FIG. 43 is an exploded, isometric top view schematic illustration of the opening mechanism first type of the surgical retractor of FIG. 36a, according to an embodiment of the present invention.

FIG. 43 is an exploded, isometric top view schematic illustration of the opening mechanism first type 60a of the surgical retractor 2 of FIG. 36a, according to an embodiment of the present invention.

The opening mechanism arms ring 62 has an opening mechanism arms ring central hole 62a, which grants it the ability to move along the length of the opening mechanism pole 61a, when the opening mechanism pole 61a is engaged within the opening mechanism arms ring central hole 62a. Furthermore, the opening mechanism arms ring 62 is equipped with pairs of opening mechanism arms ring arms 62b, each pair being connected, by means of an opening mechanism arm upper pivot 62a, to an opening mechanism arm 63, near one of its ends. Near its other end, the opening mechanism arm 63 is connected, by means of an opening mechanism arm lower pivot 63b, to an opening mechanism slider 64.

The opening mechanism arm 63 has ability for rotational movement relative to opening mechanism arm upper pivot 62a and to an opening mechanism arm lower pivot 63b.

The opening mechanism base 65 has an opening mechanism base hole 65a, which serves for its connection to the opening mechanism pole 61a.

The opening mechanism base 65 includes opening mechanism base grooves 65b, each of which serves to enable and guide movement within and along opening mechanism slider 64.

Both sides of opening mechanism base groove 65b have two opening mechanism base tracks 65c.

The opening mechanism slider 64 has an external shape and dimensions that are suitable to receive force by means of an opening mechanism arm lower pivot 63*b* from an opening mechanism arm 63, in order to perform linear movement within an opening mechanism base groove 65*b* upon a pair of opening mechanism base tracks 65*c*, and in order to transmit force to a main slider 15, (not shown in the present illustration).

This external shape also includes an opening mechanism slider upper channel 64*a*, an opening mechanism slider bottom channel 64*b*, two opening mechanism slider side channels 64*c*, and an 64*d* opening mechanism slider pushing portion.

All of the features of the ribs 21, the flexible sleeve 23 and the central rod 30 as shown in FIGS. 2*a*-2*c*, 3*b*, 7*a*, 10*a*, 10*e*-10*h*, 11, 12*a*-12*c*, 13*a*-13*c*, 14*a*-14*h*, 18*a*-18*f*, 20-25, 27*a*-27*f*, and 28, and their accompanying descriptions, also apply to their use in the surgical retractors 2, of FIGS. 36*a* and 29*a*.

Figure 44A:
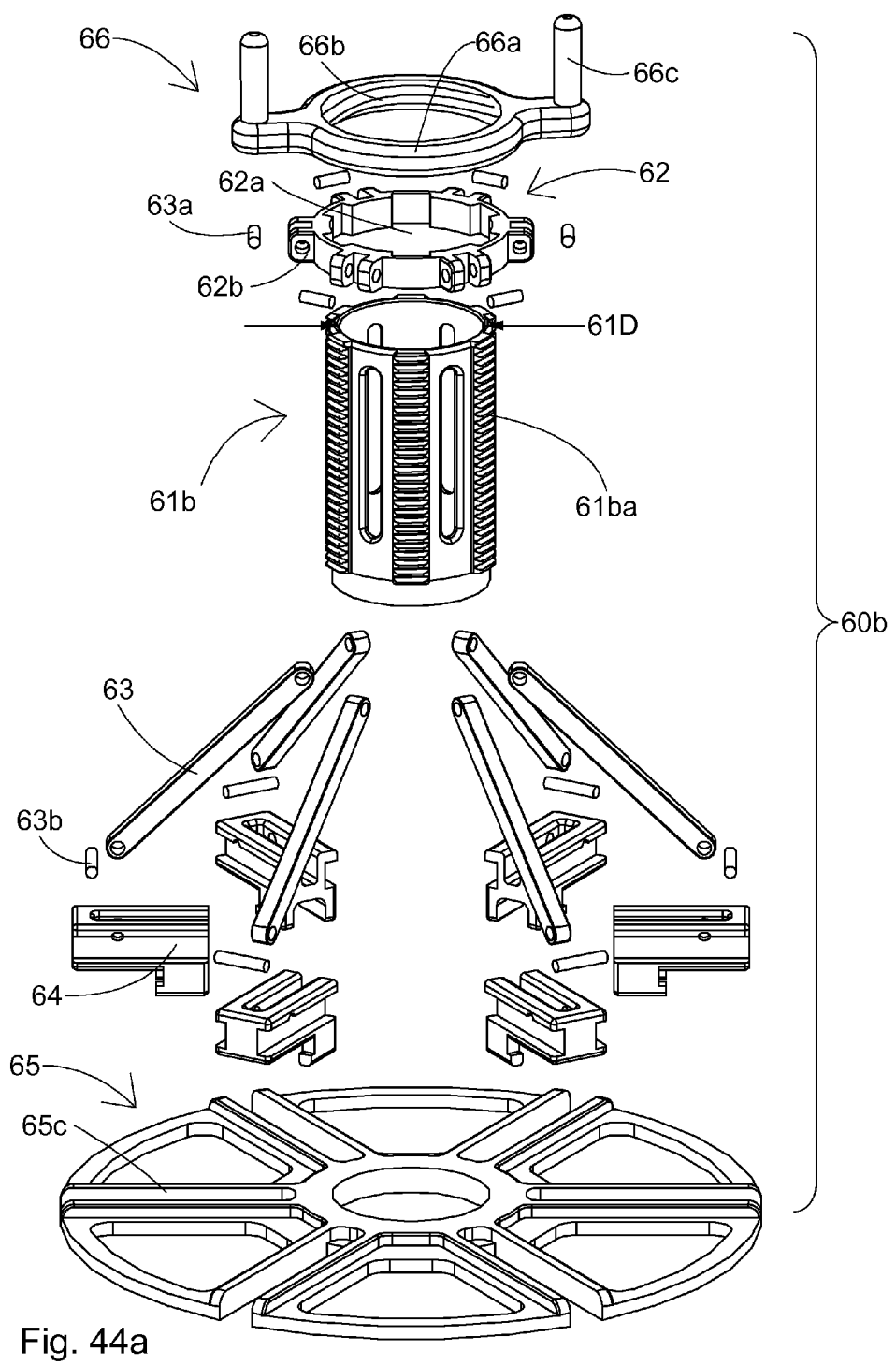
FIG. 44a is an exploded, isometric top view schematic illustration of the opening mechanism second type of the surgical retractor of FIG. 36a, according to an embodiment of the present invention.

FIG. 44*a* is an exploded, isometric top view schematic illustration of the opening mechanism second type 60*b* of the surgical retractor 2 of FIG. 36*a*, according to an embodiment of the present invention.

The opening mechanism second type 60*b* operates in a similar manner to that of the opening mechanism first type 60*a* (not shown in the present illustration), however it is constructed so as to enable the surgeon to view through its center when opening. For this purpose, an opening mechanism cylinder 61*b* replaces the opening mechanism pole 61*a*, (not shown in the present illustration).

The opening mechanism cylinder 61*b* has an opening mechanism cylinder internal diameter 61D of a predetermined minimum value which ensures a sufficiently large visual range. On the external side of the opening mechanism cylinder 61*b* there is an opening mechanism cylinder external thread 61*ba*. The opening force is transmitted manually or by means of an engine, (not shown in the present invention), to opening mechanism nut 66, which in turn presses on the opening mechanism arms ring 62.

The opening mechanism arms ring central hole 62*a* is large enough, and conforms to the external dimensions of the opening mechanism cylinder 61*b*.

The opening mechanism nut 66 includes an opening mechanism nut body 66*a* containing an opening mechanism nut internal thread 66*b*, which conforms to opening mechanism cylinder external thread 61*ba*.

Figure 44B:
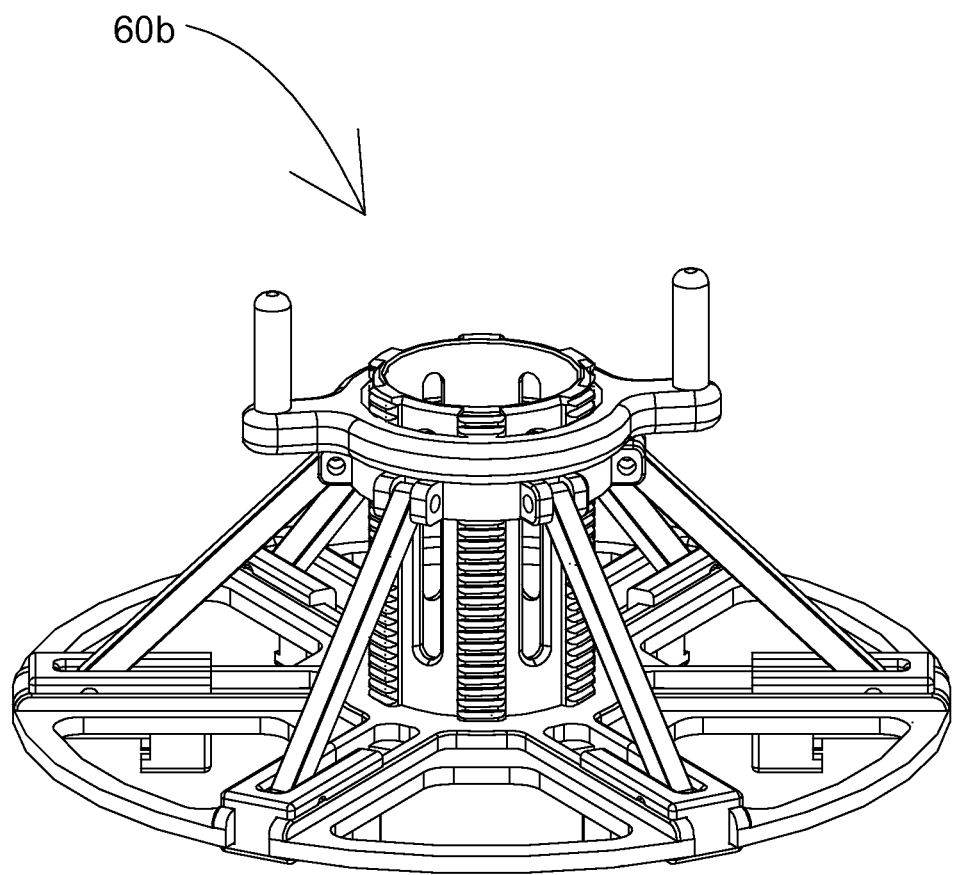
FIG. 44b is an isometric top view schematic illustration of the opening mechanism second type of the surgical retractor of FIG. 36a, according to an embodiment of the present invention.

FIG. 44*b* is an isometric top view schematic illustration of the opening mechanism second type 60*b* of the surgical retractor 2 of FIG. 36*a*, according to an embodiment of the present invention.

Both the opening mechanism first type and opening mechanism second type can also be composed of various materials, also including metals, plastics, and materials transparent to x-rays.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A surgical retractor, comprising: (a) a ribs assembly; (b) a mechanism for transferring of linear and rotational movement adapted to apply mechanical forces and moments to said ribs assembly; and (c) a channeled disc wherein said mechanism for transferring of linear and rotational movement and said ribs assembly are mounted on said channeled disc, wherein said mechanism for transferring of linear and rotational movement includes: (i) at least one main slider, wherein said main slider has a main slider upper portion having an upper portion length, a main slider mid portion, having a mid portion length wherein said main slider mid portion is disposed on said main slider upper portion, and a main slider lower portion, having a lower portion length, wherein said main slider lower portion is disposed on said main slider mid portion, wherein said upper portion length is larger than said mid portion length, wherein said lower portion length is larger than said upper portion length, and wherein said main slider lower portions is partially mounted inside one of said channels, wherein said main slider has a first interior thread located in said main slider upper portion; (ii) at least one angular adjustment bolt wherein said angular adjustment bolt is mounted inside said first interior thread and is adapted for transferring force to one of rib force arms, wherein said main slider has a second interior thread located in said main slider mid portion; and (ii) at least one linear adjustment bolt wherein said linear adjustment bolt is mounted inside said second interior thread.

2. The surgical retractor of claim 1, wherein said channeled disc is made of material selected from a group consisting of nylon and polycarbonate.

3. The surgical retractor of claim 2, wherein said ribs assembly includes:
   (i) at least two ribs, wherein each one of said ribs has a rib force arm and a rib working arm disposed on said rib force arm, wherein said rib has a rib back surface, a rib front surface, a rib top end, a rib bottom end, and a rib shoulder, wherein said rib shoulder is disposed on said force arm, wherein said rib force arm has a rib force arm length and a rib force arm width, wherein said rib force arm width tapers toward said rib top end, wherein said rib working arm has a rib working arm length and a rib working arm width, wherein said rib working arm width tapers toward said rib bottom end, and wherein said rib has a concave segment of a rib front surface said concave segment of a rib front surface having a concave segment of a rib front surface diameter.

4. The surgical retractor of claim 3, wherein said ribs are made of material containing nylon and carbon fibers.

5. The surgical retractor of claim 3, wherein said ribs are made of stainless steel.

6. The surgical retractor of claim 3, wherein at least one of said rib working arm lengths is larger than at least another one of said rib working arm length.

7. The surgical retractor of claim 3, wherein said channeled disc includes:
   (i) at least two channels.

8. The surgical retractor of claim 1 wherein each of said main sliders includes:
   a pair of slider arms disposed on said main slider lower portion; and
   a slider pivot disposed on said pair of slider arms, wherein said main slider lower portion has a slider among arms surface and wherein there is a gap between the slider pivot and the slider among arms surface having a predetermined dimension value, and wherein said slider pivot is adapted for transferring force to said concave segment of a rib front surface.

9. The surgical retractor of claim 1, further comprising:
   (d) a lighting assembly disposed on said channeled disc.

* * * * *